US010941447B2

(12) United States Patent
Dudley, Jr. et al.

(10) Patent No.: US 10,941,447 B2
(45) Date of Patent: Mar. 9, 2021

(54) DIAGNOSTICS FOR PULMONARY ARTERIAL HYPERTENSION AND SUDDEN CARDIAC DEATH

(71) Applicant: Rhode Island Hospital, Providence, RI (US)

(72) Inventors: Samuel C. Dudley, Jr., Providence, RI (US); Corey E. Ventetuolo, Bristol, RI (US)

(73) Assignee: Rhode Island Hospital, Providence, RI (US)

( * ) Notice: Subject to any disclaimer, the term of this patent is extended or adjusted under 35 U.S.C. 154(b) by 209 days.

(21) Appl. No.: 15/443,762

(22) Filed: Feb. 27, 2017

(65) Prior Publication Data

US 2018/0094317 A1 Apr. 5, 2018

Related U.S. Application Data

(60) Provisional application No. 62/301,517, filed on Feb. 29, 2016, provisional application No. 62/318,484, filed on Apr. 5, 2016.

(51) Int. Cl.

| | |
|---|---|
| ***C12Q 1/6883*** | (2018.01) |
| ***G01N 33/577*** | (2006.01) |
| ***C12Q 1/686*** | (2018.01) |
| ***C12Q 1/6804*** | (2018.01) |
| ***G01N 33/68*** | (2006.01) |

(52) U.S. Cl.

CPC ......... *C12Q 1/6883* (2013.01); *C12Q 1/6804* (2013.01); *C12Q 1/686* (2013.01); *G01N 33/577* (2013.01); *G01N 33/6893* (2013.01); *C12Q 2600/106* (2013.01); *C12Q 2600/118* (2013.01); *C12Q 2600/156* (2013.01); *C12Q 2600/158* (2013.01); *G01N 2800/321* (2013.01)

(58) Field of Classification Search

CPC .. C12Q 1/686; C12Q 1/6804; C12Q 2600/18; C12Q 2600/156; C12Q 2600/158; G01N 2800/321; G01N 33/577

USPC .... 435/6.1, 6.12, 91.1, 91.31, 455; 530/300, 530/350; 536/23.1, 24.5

See application file for complete search history.

(56) References Cited

U.S. PATENT DOCUMENTS

| | | | |
|---|---|---|---|
| 4,816,567 | A | 3/1989 | Cabilly et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 6,719,971 | B1 | 4/2004 | Carter et al. |
| 2007/0212723 | A1 | 9/2007 | Dudley et al. |
| 2009/0092998 | A1 | 4/2009 | Dudley |
| 2010/0233727 | A1 | 9/2010 | Dudley |
| 2012/0129179 | A1 | 5/2012 | Dudley |
| 2013/0189690 | A1 | 7/2013 | Dudley |

FOREIGN PATENT DOCUMENTS

| | | |
|---|---|---|
| WO | 2012/094651 A2 | 7/2012 |

OTHER PUBLICATIONS

Boyd et al. (Jan. 26, 2014) "*Homo sapiens* Small Nuclear Ribonucleoprotein Polypeptide E( SNRPE) mRNA", GenBank Accession No. NM_003094.2, 3 pages.

Burel et al. "*Homo sapiens* Sodium Voltage-Gated Channel Alpha Subunit 5( SCN5A), Transcript Variant 1, mRNA", GenBank Accession No. NM_198056.2, 11 pages.

Burel et al. "Sodium Channel Protein Type 5 Subunit Alpha Isoform a [*Homo sapiens*]", GenBank Accession No. NP_932173.1, 6 pages.

Carlson et al. "*Homo sapiens* RNA Binding Motif Protein 25 (RBM25), mRNA", GenBank Accession No. NM_021239.2, 6 pages.

Chacko et al. (2013) "Methods for Defining Distinct Bioenergetic Profiles in Platelets, Lymphocytes, Monocytes, and Neutrophils, and the Oxidative Burst from Human Blood", Laboratory Investigation, 93(6):690-700.

Chambers et al. (Jan. 5, 2016) "*Homo Sapiens* Eukaryotic Translation Initiation Factor 2A( EIF2A), mRNA", GenBank Accession No. NM_032025.3, 6 pages.

Chothia et al. (Aug. 20, 1987) "Canonical Structures for the Hypervariable Regions of Immunoglobulins", Journal of Molecular Biology, 196(4):901-917.

Chothia et al. (Dec. 28, 1989) "Conformations of Immunoglobulin Hypervariable Regions", Nature, 342:877-883.

Chung et al. (Nov. 28, 2013) "A Novel Channelopathy in Pulmonary Arterial Hypertension", The New England Journal of Medicine, 369(22):2161-2162.

Cole et al. (1985) "Monoclonal Antibodies and Cancer Therapy", Supplement: UCLA Symposia on Molecular & Cellular Biology, 29(9A):33-74.

Cosnefroy et al. (Feb. 19, 2014) "*Homo sapiens* Eukaryotic Translation Initiation Factor 2a Lpha Kinase 4 ( EIF2AK4), mRNA", GenBank Accession No. NM_001013703.2, 6 pages.

Davila et al. (Apr. 11, 2010) "*Homo sapiens* DnaJ (Hsp40) Homolog, Subfamily C, Member 3(DNAJC3), mRNA", GenBank Accession No. NM_006260.3, 5 pages.

Fang et al. (Jul. 2012) "Comparison of 18F-FDG Uptake by Right Ventricular Myocardium in Idiopathic Pulmonary Arterial Hypertension and Pulmonary Arterial Hypertension Associated with Congenital Heart Disease", Pulmonary circulation, 2(3)365-372.

Galie et al. (Dec. 24, 2013) "The Fifth World Symposium on Pulmonary Hypertension", Journal of the American College of Cardiology, 62(25):D1-D3.

Gao et al. (Jun. 3, 2014) "Enhanced Risk Profiling of Implanted Defibrillator Shocks With Circulating SCN5A mRNA Splicing Variants: A Pilot Trial", Journal of the American College of Cardiology, 63(21):2261-2269.

(Continued)

*Primary Examiner* — Jane J Zara

(74) *Attorney, Agent, or Firm* — Mintz Levin Cohn Ferris Glovsky and Popeo, P.C.; Ingrid A. Beattie

(57) ABSTRACT

This invention relates to a diagnostic test measuring circulating SCN5A proteins or gene transcripts in a test sample as a biomarker for pulmonary hypertension.

15 Claims, 11 Drawing Sheets

Specification includes a Sequence Listing.

(56) References Cited

OTHER PUBLICATIONS

Gao et al. (Sep. 6, 2011) "The Role of RBM25/LUC7L3 in Abnormal Cardiac Sodium Channel Splicing Regulation in Human Heart Failure", Circulation, 124(10):1124-1131.

Gao (Oct. 2013) "The Unfolded Protein Response Regulates Cardiac Sodium Current in Systolic Human Heart Failure", Circulation: Arrhythmia and Electrophysiology, 6(5):1018-1024.

Genbank Database (Dec. 15, 2017) "*Homo sapiens* Eukaryotic Translation Initiation Factor 2 Alpha Kinase (Eif2ak3), Refseqgene (Lrg_1024) on Chromosome 2", GenBank Accession No. NG_016424. 1, 18 pages.

Goding (1986) "Monoclonal Antibodies: Principles and Practice", Academic Press, 59-103.

Hatakeyama et al. (Sep. 30, 1994) "Vascular Aldosterone. Biosynthesis and a Link to Angiotensin Li-Induced Hypertrophy of Vascular Smooth Muscle Cells", Journal of Biological Chemistry, 269(39):24316-24320.

Hoeper et al. (Feb. 2002) "Outcome after Cardiopulmonary Resuscitation in Patients with Pulmonary Arterial Hypertension", American Journal of Respiratory and Critical Care Medicine, 165(3):341-344.

Hoogenboom et al. (Sep. 20, 1992) "By-Passing immunisation: Human Antibodies from Synthetic Repertoires of Germline VH Gene Segments Rearranged in Vitro", Journal of Molecular Biology, 227(2):381-388.

Hoppman et al. (Jul. 21, 2010) "*Homo sapiens* Fibroblast Growth Factor Binding Protein 1( FGFBP1), mRNA", GenBank Accession No. NM_005130.3, 3 pages.

Jeevaratnam et al. (2012) "Frequency Distribution Analysis of Activation Times and Regional Fibrosis in Murine Scn5a+/−Hearts: The Effects of Ageing and Sex", Mechanisms of Ageing and Development, 133:591-599.

Jones et al. (May 29, 1986) "Replacing the Complementarity-Determining Regions in a Human Antibody with those from a Mouse", Nature, 321(6069):522-525.

Köhler et al. (Aug. 7, 1975) "Continuous Cultures of Fused Cells Secreting Antibody of Predefined Specificity", Nature, 256(5517):495-497.

Kuriyama (Jan. 1992) "Clinical Aspects of Precapillary Pulmonary Hypertension", Nihon Kyobu Shikkan Gakkai Zasshi, 30(1):3-11.

Lakdawala et al. (Feb. 1, 2013) "Dilated Cardiomyopathy", Circulation: Arrhythmia and Electrophysiology, 6(1):228-237.

Lam et al. (Mar. 31, 2009) "Pulmonary Hypertension in Heart Failure with Preserved Ejection Fraction: A Community-Based Study", Journal of the American College of Cardiology, 53(13):1119-1126.

Lambiase et al. (Jul. 14, 2009) "High-Density Substrate Mapping in Brugada Syndrome: Combined Role of Conduction and Repolarization Heterogeneities in Arrhythmogenesis", Circulation, 120(2):106-117.

Liu et al. (Oct. 2014) "Cardiac Sodium Channel Mutations: Why so Many Phenotypes?", Nature Reviews Cardiology, 11(10):607-615.

Liu et al. (Jan. 16, 2016) "Cloning and Transcriptional Activity of the Mouse Omi/HtrA2 Gene Promoter", International Journal of Molecular Science, 17(1):12 pages.

Lonberg et al. (Apr. 28, 1994) "Antigen-Specific Human Antibodies from Mice Comprising Four Distinct Genetic Modifications", Nature, 368:856-859.

Lonberg et al. (Jul. 10, 2009) "Human Antibodies from Transgenic Mice", Journal International Reviews of Immunology, 13(1):65-93.

Lundgrin et al. (Feb. 2013) "Fasting 2-Deoxy-2-[18F]fluoro-D-glucose Positron Emission Tomography to Detect Metabolic Changes in Pulmonary Arterial Hypertension Hearts over 1 Year", Annals of the American Thoracic Society, 10(1):1-9.

Maarof et al. (May 2, 2010) "*Homo sapiens* Interleukin 24 (IL24), Transcript Variant 1, mRNA", GenBank Accession No. NM_006850. 2, 4 pages.

Maarof et al. (Jun. 6, 2010) "*Homo sapiens* Interleukin 24 (IL24), Transcript Variant 2, mRNA", GenBank Accession No. NM_181339. 1, 3 pages.

Marks et al. (Dec. 5, 1991) "By-Passing Immunization: Human Antibodies from V-Gene Libraries Displayed on Phage", Journal of Molecular Biology, 222(3):581-597.

Maron et al. (Jun. 2014) "The Role of the Renin-Angiotensin-Aldosterone System in the Pathobiology of Pulmonary Arterial Hypertension (2013 Grover Conference Series)", Pulmonary Circulation, 4(2):200-2010.

Marsboom et al. (May 25, 2012) "Dynamin-Related Protein 1-Mediated Mitochondrial Mitotic Fission Permits Hyperproliferation of Vascular Smooth Muscle Cells and Offers a Novel Therapeutic Target in Pulmonary Hypertension", Circulation Research, 110(11):1484-1497.

Mclaughin et al. (Apr. 28, 2009) "ACCF/AHA 2009 Expert Consensus Document on Pulmonary Hypertension", A Report of the American College of Cardiology Foundation Task Force on Expert Consensus Documents and the American Heart Association: with the American College of Chest Physicians, American Thoracic Society, Inc. and the Pulmonary Hypertension Association, 53(17):1573-1619.

Meregalli et al. (Aug. 15, 2005) "Pathophysiological Mechanisms of Brugada Syndrome: Depolarization Disorder, Repolarization Disorder, or more ?", Cardiovascular Research, 67(3):367-378.

Mesicek et al. (Sep. 25, 2011) "*Homo sapiens* Ceramide Synthase 6(CERS6), mRNA", GenBank Accession No. NM_203463.1, 5 pages.

Morrell et al. (1997) "Right Ventricular Angiotensin Converting Enzyme Activity and Expression Is Increased During Hypoxic Pulmonary Hypertension", Cardiovascular Research, 34(2):393-403.

Morrison (Apr. 28, 1994) "Success in Specification", Nature, 368:812-813.

Oikawa et al. (Jun. 7, 2005) "Increased [18F]Fluorodeoxyglucose Accumulation in Right Ventricular Free Wall in Patients With Pulmonary Hypertension and the Effect of Epoprostenol", Journal of the American College of Cardiology, 15(11):1849-1855.

Rainbolt et al. (Oct. 2014) "Stress-Responsive Regulation of Mitochondria through the ER Unfolded Protein Response", Trends in Endocrinology & Metabolism, 25(10):528-537.

Ranza, et al., "*Homo sapiens* Serpin Family I Member 1( SERPINI1), Transcript Tariant 1, mRNA", GenBank 4ccession No. NM_005025. 4, 4 pages.

Ranza et al. "*Homos sapiens* Serpin Family I Member 1( SERPINI1), Transcript Variant 2, mRNA", GenBank Accession No. NM_001122752. 1, 4 pages.

Rashid et al. "*Homo Sapiens* Endoplasmic Reticulum to Nucleus Signaling 2( ERN2), Transcript Variant 1, mRNA", GenBank Accession No. NM_033266.3, 5 pages.

Rich et al. (Aug. 10, 2013) "QTc Prolongation is Associated with Impaired Right Ventricular Function and Predicts Mortality in Pulmonary Hypertension", International Journal of Cardiology, 167(3):669-676.

Riechmann et al. (Apr. 1988) "Reshaping Human Antibodies for Therapy", Nature, 332:323-327.

Rutledge et al. (Jul. 2013) "Mitochondria and Arrhythmias", Expert Review of Cardiovascular Therapy, 11(7):799-801.

Salanova et al. (Jun. 27, 2010) "*Homo sapiens* ATPase, C a++ Transporting, Cardiac Muscle, Fast Twitch 1 ( ATP2A1), Transcript Variant a, mRNA", GenBank Accession No. NM_173201.2, 5 pages.

Salanova et al. (Jun. 20, 2010) "Homosapiens ATPase, C a++ Transporting, Cardiac Muscle, Fast Twitch 1 ( ATP2A1), Transcript Variant b, mRNA", GenBank Accession No. NM_004320.3, 5 pages.

Shang et al. (Nov. 2007) "Human Heart Failure Is Associated With Abnormal C-Terminal Splicing Variants in be Cardiac Sodium Channel", Circulation Research, 101(11):1146-1154.

Simonneau et al. (Dec. 24, 2013) "Updated Clinical Classification of Pulmonary Hypertension", Journal of the American College of Cardiology, 62(25):D34-D41.

(56) References Cited

OTHER PUBLICATIONS

Simonneau et al. (Jun. 30, 2009) "Updated Clinical Classification of Pulmonary Hypertension", Journal of the American College of Cardiology, 54:D43-D54.
Strausberg et al. (Oct. 23, 2006) "*Homo sapiens* Eukaryotic Translation Initiation Factor 2-Alpha Kinase 3, Mrna (Cdna Clone Mgc:161632 Image:8992070), Complete Cds", GenBank: BC126354.1, 3 pages.
Strausberg et al. (Oct. 23, 2006) "*Homo sapiens* Eukaryotic Translation Initiation Factor 2-Alpha Kinase 3, Mrna (Cdna Clone Mgc:161634 Image:8992072), Complete Cds", GenBank: BC126356_1, 3 pages.
Szlavicz et al. "*Homo sapiens* LUC7 like 3 pre-mRNA Splicing Factor (LUC7L3), Transcript Variant 1, mRNA", GenBank Accession No. NM_016424.4, 5 pages.
Szlavicz et al. "*Homo sapiens* LUC7 like 3 pre-mRNA Splicing Factor (LUC7L3), Transcript Variant 2, mRNA", GenBank Accession No. NM_006107.3, 5 pages.
Tanaka et al. "Right Ventricular Electrical Remodeling and Arrhythmogenic Substrate in Rat Pulmonary Hypertension", American Journal of Respiratory Cell and Molecular Biology, 49(3):426-436.
Thenappan et al. (May 2010) "Survival in Pulmonary Arterial Hypertension: A Reappraisal of the NIH Risk Stratification Equation", European Respiratory Journal, 35(5):1079-1087.
Tonelli et al. (Aug. 2013) "Causes and Circumstances of Death in Pulmonary Arterial Hypertension", American Journal of Respiratory and Critical Care Medicine, 188(3):365-369.
Tuder, et al., "Pathology of Pulmonary Hypertension", Clinics in Chest Medicine, vol. 34, No. 4, Dec. 2013, pp. 539-650.
Vannuvel et al. (2016) "Effects of a Sublethal and Transient Stress of the Endoplasmic Reticulum on the Mitochondrial Population", Journal of Cellular Physiology, 231:1913-1931.
Verhoeyen et al. (Mar. 25, 1988) "Reshaping Human Antibodies: Grafting an Antilysozyme Activity", Science, 239 (4847):1534-1536.
Wang et al. (Mar. 15, 2015) "*Homo sapiens* Eukaryotic Translation Initiation Factor 2-alpha kinase 3( EIF2AK3), mRNA", GenBank Accession No. NM_004836.5, 5 pages.
Weinberg et al. (May 2010) "Mitochondri Metabolism and ROS Generation are Essential for Kras-Mediated Tumorigenicity", Proceedings of the National Academy of Sciences of U.S.A, 107(19):8788-8793.
World et al. (Sep. 25, 2011) "*Homo sapiens* Thioredoxin (TXN), mRNA", GenBank Accession No. NM_003329.2, 4 pages.
Zhang et al. (Aug. 2014) "Arrhythmic Substrate, Slowed Propagation and Increased Dispersion in Conduction—Direction in the Right Ventricular Outflow Tract of Murine Scn5a+/? Hearts", Acta Physiologica Oxford, 211(4):559-573.
Zhang et al. (Oct. 2009) "Role of HIF-1 in the Regulation ACE and ACE2 Expression in Hypoxic Human Pulmonary Artery Smooth Muscle Cells", American Journal of Physiology-Lung Cellular and Molecular Physiology, 297 (4):L631-640.
Zhou et al. (Oct. 2008) "Novel Splicing Factor RBM25 Modulates Bcl-x Pre-mRNA 5' Splice Site Selection", Molecular and Cellular Biology, 28(19):5924-5936.
Ahmadi et al. (Jan. 2015) "FDG PET Imaging for Identifying Pulmonary Hypertension and Right Heart Failure", Current Cardiology Reports, 17(1):555.
James (Feb. 1, 1962) "On the Cause of Syncope and Sudden Death in Primary Pulmonary Hypertension", Annals of Internal Medicine, 56(2):252-264.
Jeevaratnam et al. (Feb. 2016) "Sodium Channel Haploinsufficiency and Structural Change in Ventricular Arrhythmogenesis", Acta physiologica (Oxford), 216(2):186-202.
Morrell et al. (Oct. 1995) "Role of Angiotensin-Converting Enzyme and Angiotensin II in Development of Hypoxic Pulmonary Hypertension", American Journal of Physiology, 269(4 Pt 2):H1186-H1194.
Wang et al. (Apr. 2013) "Evaluation of Right Ventricular Volume and Ejection Fraction by Gated 18F-FDG PET in Patients with Pulmonary Hypertension: Comparison with Cardiac MRI and CT", Journal of Nuclear Cardiology, 20(2):242-252.

DIAGNOSTICS FOR PULMONARY ARTERIAL HYPERTENSION AND SUDDEN CARDIAC DEATH

CROSS-REFERENCE TO RELATED APPLICATIONS

This application claims benefit of priority to U.S. Provisional Application No. 62/318,484, filed Apr. 5, 2016, and U.S. Provisional Application No. 62/301,517, filed Feb. 29, 2016, the entire contents of each of which are incorporated herein by reference.

STATEMENT AS TO FEDERALLY SPONSORED RESEARCH

This invention was made with government support under grant number NIH P20GM103652 awarded by the National Institutes of Health. The Government has certain rights in the invention.

FIELD OF THE INVENTION

The present invention relates to heart disease.

REFERENCE TO THE SEQUENCE LISTING

The content of the text file named "21486-626001US_Sequence_Listing.txt" which was created on Feb. 27, 2017 and is 101 kilobytes in size is hereby incorporated by reference in its entirety.

BACKGROUND

Pulmonary arterial hypertension (PAH) is an isolated pulmonary vasculopathy associated with a limited life expectancy (Thenappan et al., Eur Respir J. 2010; 35(5): 1079-87). While right ventricular (RV) failure is the proximate cause of death in PAH, predictors of RV phenotype and death are not well understood. As many as 26% of PAH patients suffer sudden cardiac death (SCD) (Tonelli et al., Am J Respir Crit Care Med. 2013; 188(3):365-9; Kuriyama, Nihon Kyobu Shikkan Gakkai Zasshi. 1992; 30(1):3-11). Common disease correlates such as functional class are not uniformly compromised prior to death suggesting an alternative mechanism to heart failure may be contributing (Tonelli et al., Am J Respir Crit Care Med. 2013).

There is a need for a reliable and cost-efficient means for diagnosing pulmonary hypertension (PH) and assessing the risk of sudden cardiac death (SCD) in subjects afflicted with PH.

SUMMARY OF THE INVENTION

The present subject matter features diagnostic/prognostic tests for identifying subjects at risk of developing PH, diagnosing subjects afflicted with PH, evaluating PH severity in subjects diagnosed with PH, and assessing the risk of SCD in subjects afflicted with PH. Methods for monitoring and treating PH, as well as for reducing the risks of becoming afflicted with PH or SCD are also provided.

The methods described herein represent a non-invasive (or minimally invasive) test assay. For example, the test sample such as blood is obtained by venipuncture, and the sample comprises circulating cells such as white cells, monocytes, T-cells or a bodily fluid such as blood, serum, or plasma. The test sample is then provided to an operator or assay device for assessment of the level of a SCN5A peptide, protein or nucleic acid defining or encoding the peptide or protein. In another example, the test sample comprises saliva. In another example, the test sample comprises a buffy coat fraction of blood. The buffy coat is a standard fraction of an anti-coagulated blood sample that contains a plurality of the white blood cells (WBCs) and platelets following density gradient centrifugation of the blood.

In various implementations of the present subject matter, the subject is a human being characterized as comprising a risk of heart disease, e.g., a previous cardiac event, a family history of heart disease, or other risk factor such as obesity or diabetes. In various embodiments, diagnostic or prognostic level of a full-length Sodium Channel, Voltage Gated, Type V alpha Protein Subunit (SCN5A) protein or a full-length SCN5A nucleic acid is a level that is decreased by at least about 10% (e.g., at least about 15%, 20%, 25%, 30%, 35%, 40%, 45%, 50% or more) compared to a normal control.

In various embodiments, and in the context of protein or mRNA levels, a "normal" amount refers to a normal amount of a protein or mRNA in an individual or a population/cohort of individuals known not to be diagnosed with PH. The amount of a protein or mRNA can be measured in a test sample and compared to a "normal control" level, utilizing techniques such as reference limits, discrimination limits, or risk defining thresholds to define cutoff points and abnormal values (e.g., for PH or SCD). Depending on the context, the normal control level means the level of a protein or mRNA typically found in a subject known to not be afflicted with PH. In some instances, the normal control level may be obtained by calculating the average of the levels of a protein or mRNA in subjects not afflicted with PH. For example, the level of a protein or mRNA in a normal control level may be the level in an individual or individuals having a mean pulmonary arterial pressure (mPAP) of about 13, 14, 15, 16 or 14-16, and/or a pulmonary capillary wedge pressure (PCWP) or left ventricular end-diastolic pressure of about 3, 4, 5, 6, 7, 8, 9, 0, 11, 12, or 3-12 mmHg, and/or a PVR of about 0.25, 0.5, 1.0, 1.5, 1.6 or 0.25-1.6 Wood units. Such normal control levels and cutoff points may vary based on whether a protein or mRNA is used alone or in a formula combining with other proteins or mRNA into an index.

The level that is determined may be the same as a control level or a cut off level or a threshold level, or may be increased or decreased relative to a control level or a cut off level or a threshold level. In some aspects, the control subject (or subjects, e.g., in the case of an averaged normal control level) is a matched control of the same species, gender, ethnicity, age group, smoking status, body mass index (BMI), current therapeutic regimen status, medical history, or a combination thereof, but differs from the subject being diagnosed in that the control does not suffer from the disease in question (such a PH) or is not at risk for the disease or occurrence (such as PH or SCD).

In some embodiments, a control level for SCD can be within or calculated using a database of protein/mRNA patterns from previously tested subjects who did not suffer from SCD over a clinically relevant time horizon.

Reduced SCN5A contributes to SCD in subjects afflicted with PH. As used herein, a subject "afflicted with PH" is a subject who has been diagnosed as having PH.

The reduction in cardiac SCN5A mRNA abundance is reflected in circulating white cells that also express SCN5A. A diagnostic or prognostic level of a short variant form of SCN5A (e.g., a splice variant) is a level that is increased by at least about 5% (e.g., at least about 10%, 15%, 20%, 25%, 30%, 35%, 40%, 45%, 50% or more) compared to a normal control. In various embodiments, the presence of the variants coincides with the reduced abundance of the full-length SCN5A mRNA. The splice variant of the SCN5A gene may be a splice variant produced from alternative splicing within Exon 28 of the SCN5A gene. In some aspects, the splice variant is a SCN5A Exon 28 B splice variant (a.k.a., E28B; Exon 28 shown as SEQ ID NO: 3), a SCN5A Exon 28 C splice variant (a.k.a., E28C; Exon 28 shown as SEQ ID NO: 4), or a SCN5A Exon 28 D splice variant (a.k.a., E28D; Exon 28 shown as SEQ ID NO: 5). For example, the presence of one or more SCN5A splice variants E28B, E28C and/or E28D in the test sample identifies the subject as being at risk for developing PH, suffering from PH, or at risk of experiencing SCD. The level of one or more SCN5A splice variants E28B, E28C and/or E28D in the test sample may also reveal the severity of PH. Methods and compositions for assessing the levels of SCN5A splice variants, as well as sequences for E28B, E28C, and E28D, are described in U.S. Application Publication No. 2012/0129179, published May 24, 2012; U.S. Application Publication No. 2007/0212723, published Sep. 13, 2007; PCT International Application No. PCT/US2012/20564, published Jul. 12, 2012; and Shang et al. "Human Heart Failure Is Associated With Abnormal C-Terminal Splicing Variants in the Cardiac Sodium Channel" Circulation Research, 2007; 101:1146-1154, the entire contents of each of which are incorporated herein by reference in their entireties.

The methods described herein may also include computing a level of SCN5A, a SCN5A variant, hypoxia-inducible factor 1a (HIF-1a), angiotensin II (Ang II), Luc7-like protein 3 (LUC7L3), RNA Binding Motif Protein 25 (RBM25), and/or protein kinase R-like ER kinase (PERK), or any combination thereof with an assay comprising a binding agent. Exemplary examples of a binding agent comprise an antibody (or fragment thereof), a detectable protein (or fragment thereof), a nucleic acid molecule (such as with a sequence that is complementary to patient mRNA or a cDNA produced from patient mRNA), or any combination thereof. The antibody may be labeled with a detectable moiety, e.g., a fluorescent compound or a radioactive agent (e.g., $^{125}$I). For example, the antibody may be part of a fusion protein that comprises the antibody and a detectable moiety. In some embodiments, the antibody is covalently conjugated to a detectable moiety. Non-limiting examples of covalent bonds that may be used to conjugate an antibody to a detectable marker include disulfide bonds, sulfur-selenium bonds, and bonds resulting from click reactions. When the fluorescently labeled antibody is exposed to light of the proper wave length, its presence can then be detected due to fluorescence. Commonly used fluorescent labeling compounds include fluorescein isothiocyanate, rhodamine, phycoerythrin, phycocyanin, allophycocyanin, p-phthaldehyde and fluorescamine. These examples are not limiting. The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). The antibody also can be detectably labeled by coupling it to a chemiluminescent compound. The presence of the chemiluminescent-tagged antibody is then determined by detecting the presence of luminescence that arises during the course of chemical reaction. Examples of particularly useful chemiluminescent labeling compounds are luminol, isoluminol, theromatic acridinium ester, imidazole, acridinium salt and oxalate ester.

According to the invention, a specific binding agent describes agents having greater than 10-fold, preferably greater than 100-fold, and most preferably, greater than 1000-fold affinity for the target molecule as compared to another molecule. The skilled artisan will appreciate the term "specific" is used to indicate that other biomolecules present in the sample do not significantly bind to the binding agent "specific" for the target molecule. Preferably, the level of binding to a biomolecule other than the target molecule results in a binding affinity which is at most only 10% or less, only 5% or less only 2% or less or only 1% or less of the affinity to the target molecule, respectively. A preferred specific binding agent will fulfill both the above minimum criteria for affinity as well as for specificity. For example, an antibody has a binding affinity in the low micromolar ($10^{-6}$), nanomolar ($10^{-7}$ to $10^{-9}$), with high affinity antibodies in the low nanomolar ($10^{-9}$) or pico molar ($10^{-12}$) range for its specific target ligand.

In some aspects, the present subject matter provides a composition utilizing a binding agent, wherein the binding agent is attached to a solid support, (e.g., a strip, a polymer, a bead, a nanoparticle, a plate such as a multiwell plate, or an array such as a microarray). In embodiments relating to the use of a nucleic acid probe attached to a solid support (such as a microarray), nucleic acid in a test sample may be amplified (e.g., using PCR) before or after the nucleic acid to be measured is hybridized with the probe. Various embodiments comprise reverse transcription polymerase chain reaction (RT-PCR) to detect mRNA levels. In some embodiments involving a probe on a solid support, the mRNA (or a portion thereof) in a test sample is converted to cDNA or partial cDNA and then the cDNA or partial cDNA is hybridized to a probe (e.g., on a microarray), hybridized to a probe and then amplified, or amplified and then hybridized to a probe. In some example, a strip may be a nucleic acid-probe coated porous or non-porous solid support strip comprising linking a nucleic acid probe to a carrier to prepare a conjugate and immobilizing the conjugate on a porous solid support. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present subject matter. The support material may have any structural configuration so long as the coupled molecule is capable of binding to a SCN5A or nucleic acid-specific binding agent (e.g., an antibody). Thus, the support configuration may be spherical, as in a bead, or cylindrical, as in the inside surface of a test tube, or the external surface of a rod. Alternatively, the surface may be flat such as a plate (or a well within a multiwell plate), sheet, or test strip, etc. Preferred supports include polystyrene beads. Those skilled in the art will know many other suitable carriers for binding antibody or antigen, or will be able to ascertain the same by use of routine experimentation.

In certain embodiments, the solid support comprises a polymer, to which an agent is chemically bound, immobilized, dispersed, or associated. A polymer support may be, e.g., a network of polymers, and may be prepared in bead form (e.g., by suspension polymerization). The location of active sites introduced into a polymer support depends on the type of polymer support. For example, in a swollen-gel-bead polymer support the active sites are distributed uniformly throughout the beads, whereas in a macroporous-bead polymer support they are predominantly on the internal surfaces of the macropores. The solid support, e.g., a device may contain an SCN5A and/or a SCN5A variant (such as a splice variant) binding agent or agents alone or together with one or more binding agents for at least one, two, three or more other molecules, e.g., HIF-1α, AngII, LUC7L3, RBM25 and/or PERK.

The present subject matter provides diagnostic tests carried out using a bodily fluid or circulating cells such as nucleated blood cells. In some cases, the cells, e.g., white blood cells, are lysed to yield a cell lysate prior to contacting the test sample (cell or cell lysate) with a SCN5A and/or SCN5A splice variant binding agent. In some embodiments, detection is accomplished using an enzyme-linked immunosorbent assay (ELISA) or Western blot format. In other examples, the binding agent binds an SCN5A and/or SCN5A splice variant nucleic acid (e.g., one or more primers or probes that are complementary for SCN5A and/or SCN5A variant mRNA or cDNA), and the detecting step is accomplished using a polymerase chain reaction (PCR) or Northern blot format, or other means of detection. In various embodiments, a probe or primer is about 10-20, 15-25, 15-35, 15-25, 20-80, 50-100, or 10-100 nucleotides in length, e.g., about 10, 12, 15, 20, 25, 30, 35, 40, 45, 50, 55, 60, 70, 80, 90, or 100 nucleotides in length or less than about 30, 35, 40, 45, 50, 55, 60, 70, 80, 90, or 100 nucleotides in length.

In certain embodiments, a cell is lysed to release a protein or nucleic acid. Numerous methods for lysing cells and assessing protein and nucleic acid levels are known in the art. Various implementations comprise physically lysing cells, such as by mechanical disruption, liquid homogenization, high frequency sound waves, freeze/thaw cycles and manual grinding. In some embodiments, a detergent is used to lyse cells. Non-limiting examples of detergents include Tween 20, Triton X-100, and Sodium Dodecyl Sulfate (SDS). Non-limiting examples of assays for determining the level of a protein include Western blot, ELISA, and protein gel electrophoresis. Non-limiting examples of assays for determining the level of an mRNA include Northern blotting, reverse transcription is followed by quantitative polymerase chain reaction (RT-PCR), and reverse transcription followed by quantitative PCR (RT-qPCR).

The term "test sample" as used herein refers to a bodily tissue, cell or fluid obtained for the purpose of evaluation using an in vitro assay. With regard to various methods disclosed herein, the sample may comprise any body fluid. In some embodiments, the bodily fluid includes, but is not limited to, blood, plasma, serum, lymph, breast milk, saliva, mucous, semen, vaginal secretions, cellular extracts, inflammatory fluids, cerebrospinal fluid, feces, vitreous humor, or urine obtained from the subject. In some aspects, the sample is a composite panel of at least two of a blood sample, a plasma sample, a serum sample, and a urine sample. In exemplary aspects, the sample comprises blood or a fraction thereof (e.g., plasma, serum, fraction obtained via leukopheresis). In exemplary aspects, the sample comprises white blood cells obtained from the subject. In exemplary aspects, the sample comprises a purified or enriched population of white blood cells. In exemplary aspects, the sample is cardiac tissue (e.g., cardiac muscle tissue). Preferred samples are whole blood, serum, plasma, or urine.

Optionally, the method further comprises repeating the providing, contacting, detecting, and computing steps over time. In various embodiments, a progressive decrease over time in the level of an SCN5A protein or SCN5A nucleic acid indicates a progressive worsening of PH, and/or increased risk of sudden cardiac death. In certain embodiments, a progressive increase over time in the level of an SCN5A variant protein or SCN5A variant nucleic acid indicates a progressive worsening of PH, or increased risk of SCD. Optionally, the method may also include the step of treatment following risk stratification as described herein.

"Risk" in the context of the present invention, relates to the probability that an event will occur, and can mean a subject's "absolute" risk or "relative" risk. In various embodiments, absolute risk is expressed as the risk of experiencing an event over a given time period or over the remainder of a subject's lifetime. In some non-limiting embodiments, a subject's absolute risk of SCD is expressed as a percentage value (e.g., a value from about 0-100%) that a subject will suffer from cardiac death within a certain amount of time (e.g., within about 1, 2, 3, 4, 5, or 0-5 years). In some embodiments, a database and/or index value is be used to calculate absolute or relative risk. In certain embodiments, relative risk is used to compare the risk between two different groups of people. For example, a subject's relative risk of SCD may be an increased likelihood that the subject will suffer from SCD compared to a subject who is not afflicted with PH, compared to the same subject at an earlier point in time, or compared to subjects afflicted with a different form of or less severe PH. A high-risk subject may comprise a subject at risk of suffering from SCD within 1 year.

In some embodiments, absolute risk is measured with reference to either actual observation post-measurement for the relevant time cohort, or with reference to index values developed from statistically valid historical cohorts that have been followed for the relevant time period. In certain embodiments, relative risk is the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1-p) where p is the probability of event and (1-p) is the probability of no event) to no-conversion.

The severity of a disease (e.g., PH) may be expressed in terms of severity of symptoms that may be mild, severe or life-threatening. Common symptoms of PH include shortness of breath (dyspnea), initially while exercising and eventually while at rest; fatigue; dizziness and/or fainting spells (syncope); chest pressure or pain; swelling (edema) of ankles and/or legs, and eventually the abdomen (ascites); a bluish color to the lips and/or skin (cyanosis); a racing pulse; and heart palpitations.

In various embodiments, the severity PH is determined without considering the magnitude of symptoms a subject can feel. In certain embodiments, the severity of PH is determined based entirely on the level of SCN5A or a variant thereof in a subject. In some embodiments, the level of SCN5A or a variant thereof in a subject is considered as part of an array of testing for PH.

Aspects of the present subject matter also provide a kit comprising an SCN5A- or SCN5A splice variant-binding agent and instructions for using the agent for diagnosing PH, assessing whether a subject's PH is worsening, and/or evaluating SCD risk. In some embodiments, the agent is attached to a solid support such a plate (such as one or more wells of a multiwell plate), a test strip, or a microarray. In some embodiments a binding agent is attached to a solid support via a covalent bond. In various embodiments, a binding agent is attached to a solid support via a high affinity interaction with a compound that is coated onto the solid support. For example, for antibodies and proteins may be coated onto a solid support by passive adsorption. In some embodiments, antibodies are attached to a solid support through the Fc region using a Protein A, G, or A/G coated solid support, which orients the antibodies properly and preserves their antigen binding capability. In various embodiments, fusion proteins are attached to a solid support in the proper orientation using glutathione, metal-chelate, or capture-antibody coated solid supports. In certain embodiments, peptides and other small molecules are biotinylated and attached with high efficiency to a streptavidin or NeutrAvidin Protein coated solid support. In various embodiments, biotinylated antibodies are immobilized on solid supports precoated with biotin-binding proteins.

The kit optionally contains buffers, enzymes, salts, stabilizing agents, preservatives, and a container for receiving a patient test sample of bodily fluid or cell. In some cases such a container contains an anti-coagulant, cell separation agent (e.g., to separate white cells from red blood cells), or a cell lysis agent, e.g., to liberate an SCN5A/SCN5A splice variant protein or an SCN5A/SCN5A splice variant nucleic acid such as mRNA from the cell to permit measurement of the protein or gene transcript). In various embodiments, the agent may be attached to a solid support (e.g., a test strip). A complex intermediate of SCN5A/SCN5A splice variant mRNA and test agent may be formed to detect such liberated SCN5A/SCN5A splice variant nucleic acid. Still another embodiment of the present subject matter is a kit comprising agents for measuring a group of markers, wherein the group of markers are defined as described in any of the paragraphs, or panels containing figures, or other descriptions of preferred sets or panels of markers found herein. In some variations, such agents are packaged together. In some variations, the kit further includes an analysis tool for evaluating risk of an individual suffering from SCD from measurements of the group of markers from at least one test sample from the subject.

The diagnostic or prognostic assay is optionally formulated in a two-antibody binding format in which one SCN5A/SCN5A splice variant protein-specific antibody captures an SCN5A/SCN5A splice variant protein, in a patient sample and another specific antibody is used to detect captured protein. For example, the capture antibody is immobilized on a solid phase, e.g., an assay plate, an assay well, a nitrocellulose membrane, a bead, a dipstick, or a component of an elution column. The second antibody, i.e., the detection antibody, is typically tagged with a detectable label such as a colorimetric agent or radioisotope.

The present disclosure also provides a diagnostic test system that obtains test results data representing levels of a marker in at least one test sample. The results are collected and tracked and a means for computing an index value from said marker, wherein the index value comprises a PH diagnosis score, a PH severity score, and/or a heart failure risk score, and a means of reporting the index value. In some embodiments the diagnostic test system produces a written report that indicates a PH risk score, PH diagnosis or diagnosis score, PH severity score, and/or SCD risk. In various embodiments, the written report is electronic. Alternatively or in addition, the written report is a printed paper report.

In some embodiments, the diagnostic test system comprises instructions for use. In some aspects, the instructions are provided as a paper copy of instructions, an electronic copy of instructions, e.g., a compact disc, a flash drive, or other electronic medium. In some aspects, the instructions are provided by way of providing directions to an internet site at which the instructions may be accessed by the user. In exemplary aspects, the instructions comprise instructions for determining an expression level of SCN5A or a variant thereof in a test sample. In various embodiments, the instructions comprise a step in which the user compares data relating to a marker to a database containing correlation data. In some aspects, the system comprises an electronic copy of a computer software program which allows the user to compare the determined level of the marker with that of a control subject or with an earlier value obtained for the subject.

The present subject matter provides a diagnostic test systems that obtain test results data representing levels of multiple markers in at least one test sample; collect and track test results data for one or more individual test samples; compute an index value from marker measurement data, wherein said biomarker measurement data is representative of measured levels of markers, wherein said measured levels of markers comprise the levels of a set or panel of markers; and report values for disease diagnosis, severity, and risk (e.g., using an index value). In some variations of the diagnostic test system, the index value is a PH severity score or a SCD risk score. In non-limiting examples, the PH severity score or SCD risk score is computed according to the methods described herein for computing such scores. In some variations, test results data from one or more individuals is collected, tracked, and/or compared using a data structure or database. In some variations, the means for computing a PH severity score or SCD risk score comprises a computer or microprocessor, such as a computer comprising a visible display, and a link to a data structure or database, and/or a printer.

Various implementations of the present subject matter relate to a collection or compilation of test results data. In certain embodiments, the collection or compilation comprises a database of test results data. In some embodiments, the data is contributed and/or collected from hospitals, clinics, and/or clinicians. For example, the data may include patient symptoms and outcomes, timelines of symptoms and outcomes, patient demographic information, and/or the level of one or more markers assayed for a subject (e.g., the level of a full-length SCN5A protein or mRNA and/or a SCN5A splice variant protein or mRNA). In various embodiments, risk and diagnostic information is continuously updated based on data collected or compiled into the database. For example, the updated risk and/or diagnostic information may be made available (e.g. using a publication such as a website) or reported (in paper copy or electronically) to hospitals, clinics, and/or clinicians. In certain embodiments, patient information is provided with a test sample and the patient information as well as the results from assaying the test sample are entered into a database.

The present subject matter provides improvements over existing methodologies for, e.g., assessing PH risk, diagnosing PH, assessing PH severity, and determining SCD risk in a subject. In an embodiment, the present subject matter provides a method comprising: obtaining marker measurement data that is representative of measurements of at two or more markers in a sample from the subject, and evaluating the presence of PH, PH severity, and/or the risk of SCD in the subject based on an output from a model, wherein the model is executed based on an input of the biomarker measurement data.

In some implementations of the present subject matter, evaluating the presence of PH, PH severity, and/or the risk of SCD is performed alone or together with the consideration of other variables, (e.g., as part of an array of testing), to establish or confirm the absence or presence of PH, or aid the physician in the prognosis, and or the monitoring of treatment. The skilled artisan will appreciate that any such evaluation or assessment made based on the level of SCN5A or a variant thereof is made using an in vitro assay. In various embodiments, the patient sample is solely used for the in vitro diagnostic method of the invention and the material of the patient sample is not transferred back into the patient's body. In certain embodiments, the sample is a liquid sample, e.g., whole blood, serum or plasma.

Certain embodiments relate to the use of a method disclosed herein as part of an array of testing. For example, an array of testing for PH may include the combination of one or more methods disclosed herein with or without one or more methods known in the art for determining or evaluating PH such as a pulmonary function test; an electrocardiography (ECG); arterial blood gas measurements; X-rays of the chest; an echocardiography; altered heart sounds (such as a second heart sound, a loud $P_2$ or pulmonic valve closure sound (part of the second heart sound), and pulmonary regurgitation); pressure measurements with a Swan-Ganz catheter through the right side of the heart; ventilation-perfusion or ventilation-perfusion (V/Q) scanning to exclude chronic thromboembolic pulmonary hypertension; and/or evaluation of peripheral edema (swelling of the ankles and feet), ascites (abdominal swelling due to the accumulation of fluid), hepatojugular reflux, and clubbing.

Aspects of the present subject matter provide methods of treating a subject. In some embodiments, the subject has been diagnosed with PH according to a method disclosed herein. In some embodiments, the subject is determined to be at risk of suffering from SCD. Methods of monitoring treatment and assessing treatment efficacy are also provided. Methods for reducing a subject's risk of suffering from PH and/or SCD are also disclosed herein.

Embodiments of the present subject matter are useful for monitoring and evaluating the effectiveness of any treatment or candidate treatment for PH. For example, methods disclosed herein may be used in a clinical setting to evaluate treatment progression or efficacy, and/or during a clinical trial to evaluate the effectiveness of a new therapy. Therapies that improve the condition of the patient identified using the risk stratification methods described herein include administration of a drug or implantation of a cardioverter-defibrillator (ICD).

Therapies for PH and/or reducing the risk of SCD include administration of one or more antiarrhythmic drugsdiuretics, digoxins, blood vessel dilators, blood thinners, calcium channel blockers, and/or vasoactive agents. Non-limiting examples of vasoactive agents include prostanoids (e.g., prostaglandins, prostacyclin, and derivatives thereof), phosphodiesterase inhibitors (e.g., phosphodiesterase type 5 (PDE-5) inhibitors), activators of soluble guanylate cyclase, prostacyclin receptor (PGI2) receptor agonist (e.g, selexipag) and endothelin antagonists (e.g., endothelin receptor antagonists). Non-limiting examples of prostanoids include prostacyclin (prostaglandin $I_2$), epoprostenol, treprostinil, remodulin, and iloprost. Non-limiting examples of endothelin receptor antagonists include bosentan, ambrisentan, and macitentan. Non-limiting examples of phosphodiesterase type 5 inhibitors include sildenafil and tadalafil. Non-limiting examples of activators of soluble guanylate cyclase include riociguat. Examples of therapies also include surgery to repair congenital heart defects. Non-limiting examples of surgical procedures include atrial septostomy, lung transplantation, shunt procedures, and pulmonary thromboendarterectomy (PTE).

In various embodiments, a subject identified to suffer from PAH or increasingly severe PAH or to have a risk or increased risk of SCD is administered an antiarrhythmic agent. Non-limiting examples of an antiarrhythmic agent include any one of a group of pharmaceuticals that are used to suppress abnormal rhythms of the heart (cardiac arrhythmias), such as atrial fibrillation, atrial flutter, ventricular tachycardia, and ventricular fibrillation. In exemplary aspects, the anti-arrhythmic agent is a Singh Vaughan Williams (SVW) Class I, II, III, IV, or V anti-arrhythmic agent. In exemplary aspects, the antiarrhythmic agent is a SVW Class IA, IB, IC, or III anti-arrhythmic agent. The antiarrhythmic agent may be a fast-channel blocker, a beta blocker, a slow channel blocker, a sodium channel blocking agent, a potassium channel blocking agent, or a calcium channel blocking agent. The anti-arrhythmic agent in some aspects is one of Quinidine, Procainamide, Disopyramide, Lidocaine, Phenytoin, Mexiletine, Tocainide, Flecainide, Propafenone, Moricizine, Propranolol, Esmolol, Timolol, Metoprolol, Atenolol, Bisoprolol, Amiodarone, Sotalol, Ibutilide, Dofetilide, Dronedarone, E-4031, Verapamil, Diltiazem, Adenosine, Digoxin, Ajmaline, Pilsicainide, or Magnesium Sulfate. In some aspects, the SVW Class IA is Quinidine, Procainamide, or Disopyramide. In some aspects, the SVW Class IB antiarrhythmic agent is Lidocaine, Phenytoin, Mexiletine, or Tocainide. In some aspects, the SVW Class IC anti-arrhythmic agent is Flecainide, Propafenone, Moricizine, or Encainide. In some aspects, the SVW Class III anti-arrhythmic agent is Dronedarone, Amiodarone, or Ibutilide. In some aspects, the anti-arrhythmic agent is NAD+ or mitoTEMPO.

Various implementations of the present subject matter relate to a method of monitoring treatment of a patient with PH by observing a change in level of an SCN5A and/or SCN5A variant protein and/or an SCN5A and/or SCN5A variant nucleic acid. Upon observation of a decreased SCN5A protein or nucleic acid level, or increased SCN5A variant protein or nucleic acid level, treatment for PH is administered.

Since accurate diagnosis of a subject leads to determining the appropriate therapy for treating the diagnosed medical condition, disease, or syndrome, the present disclosure also provides related methods of determining need for therapy or prophylaxis of a subject. For example, the present subject matter provides methods of determining need for therapy or prophylaxis for PH or SCD for a subject identified as having a risk (e.g., an increased risk compared to a normal control or other patients afflicted with PH) for PH or SCD. In various embodiments, the method comprises the step of determining a level of an abnormal splice variant or SCN5A in a test sample from the subject, wherein an increased level indicates the need for a therapy or prophylaxis for PH or sudden cardiac death. In certain embodiments, the method comprises the step of determining a level of full-length SCN5A in a test sample from the subject, wherein a decreased level indicates the need for a therapy or prophylaxis for PH or sudden cardiac death.

Intervention via active therapy or active prophylaxis may decrease the risk for developing the medical condition, disease, or syndrome. Aspects of the present subject matter provide methods of decreasing the severity of PH in a subject. The methods may comprise (i) determining a level of an abnormal SCN5A splice variant in a test sample from a subject, and (ii) administering to the subject a therapeutic or prophylactic agent, if the level determined in (i) is increased. Alternatively or in addition, the method comprises the steps of (i) determining a level of full-length SCN5A in a test sample from a subject, and (ii) administering to the subject a therapeutic or prophylactic agent, if the level determined in (i) is decreased. Aspects of the present subject matter also provide methods of decreasing the risk of SCD in a subject. The method comprises the steps of (i) determining a level of an abnormal SCN5A splice variant in a test sample from the subject, and (ii) administering to the subject a therapeutic or prophylactic agent, if the level determined in (i) is increased. Alternatively or in addition, the method comprises the steps of (i) determining a level of full-length SCN5A in a test sample from a subject, and (ii) administering to the subject a therapeutic or prophylactic agent, if the level determined in (i) is decreased.

In some embodiments, a method to monitor the efficacy of treatment is provided. In such embodiments, the method comprises determining a level of SCN5A or a SCN5A splice variant in a test sample of a subject before and after treatment. In such a method, a change in the level of SCN5A and/or the SCN5A splice variant in the sample taken after treatment compared to the level of SCN5A and/or the SCN5A splice variant before treatment indicates efficacy of the treatment. In some embodiments, a first test sample is obtained from the subject to be treated prior to initiation of therapy or part way through a therapy regime. In various embodiments, a test sample is provided to a person performing the assay. Alternatively, in some embodiments, a first test sample is obtained or provided from a subject known not to suffer from a condition being treated. In some embodiments, the second test sample is obtained or provided in a similar manner, but at a time following onset of therapy. The second test sample, in some embodiments, is obtained or provided at the completion of, or part way through therapy, provided that at least a portion of therapy takes place between the isolation of the first and second test samples. An increase in the level of full-length SCN5A in the second test sample (e.g., post-treatment) compared to the level of full-length SCN5A in the first test sample (e.g., prior to treatment or from a subject known not to suffer from the condition being treated) indicates a degree of effective therapy. A decrease in the level of SCN5A splice variant in the second test sample (e.g., post-treatment) compared to the level of SCN5A splice variant in the first test sample (e.g., prior to treatment or from a subject known not to suffer from the condition being treated) indicates a degree of effective therapy.

Aspects of the present subject matter provide a method for treating a subject afflicted with PH, or who is at risk of developing PH or dying from sudden cardiac death, comprising inhibiting the downregulation (e.g., by abnormal splicing) of the SCN5A gene in the subject or in a cell of the subject. Splicing factors LUC7L3 and RBM25 play a role in the abnormal splicing of SCN5A. See, e.g., U.S. Patent Application Publication No. 2012/0129179, published May 24, 2012, the entire content of which is incorporated herein by reference. In some embodiments, treating the subject comprises administering to the subject a compound that inhibits activity of splicing factor LUC7L3, splicing factor RBM25 and/or PERK in an amount effective to inhibit downregulation of the SCN5A gene. In various embodiments, downregulation of splicing factor LUC7L3 or splicing factor RBM25 downregulates expression of abnormal SCN5A splice variants. In certain embodiments, the abnormal SCNA splice variant is selected from the group consisting of E28B, E28C and E28D. In an embodiment, downregulation of PERK upregulates expression of full-length SCN5A.

It has been shown that RBM25 is a splicing factor that binds tightly to the canonical RNA sequence CGGGC(A) (Zhou et al., Mol. Cell. Biol., 28:5924-5936, 2008). Therefore, in some embodiments, the compound that inhibits activity of splicing factor RBM25 reduces splicing factor interaction with the canonical sequence CGGGCA in a genomic polynucleotide encoding SCN5A.

Any compound that inhibits the activity of LUC7L3, RBM25 and/or PERK is contemplated for use in the methods described herein. In one embodiment, the compound includes inhibitor oligonucleotides or polynucleotides, including pharmaceutically acceptable salts thereof, e.g., sodium salts. Non-limiting examples include antisense oligonucleotides, triplex oligonucleotides, ribozymes/deoxyribozymes (DNAzymes), small-interfering RNAs/RNAi, aptamers, and decoy oligonucleotides. In some embodiments involving antisense oligonucleotides (e.g., antisense oligodeoxynucleotides or RNAi), and depending on the length of the complementary region, one, two or more mismatches are tolerated without affecting inhibitory function. In certain embodiments, the inhibitory oligonucleotide is an antisense oligonucleotide, an inhibitory RNA (including siRNA or RNAi, miRNA, or shRNA), a DNA enzyme, a ribozyme (optionally a hammerhead ribozyme), an aptamer, or pharmaceutically acceptable salts thereof. In one embodiment, the oligonucleotide is complementary to at least about 10, 11, 12, 13, 14, 15, 16, 17, 18, 19, 20, 21, 22, 23, 24, or 25 bases or about 10, 11, 12, 13, 14, 15, 16, 17, 18, 19, 20, 21, 22, 23, 24, or 25 bases of the LUC7L3 mRNA sequence (Genbank Accession Nos. NM_006107.3 and NM_016424.4), the RBM25 mRNA sequence (Genbank Accession No.: NM_021239.2) or a PERK mRNA sequence (including, but not limited to, Genbank Accession Nos: NM_003094.2, NM_004320.3, NM_0173201.2, NM_203463.1, NM_006850.2, NM_003329.2, NM_181339.1, NM_006260.3, NG_016424.1, NM_004836.5, NM_001122752.1, NM_005025.4, NM_033266.3, NM_032025.3, NM_005130.3, NM_001013703.2, BC126356.1 and BC126354.1).

Various cDNA sequences are disclosed herein. In an mRNA sequence that corresponds to a cDNA sequence, each "T" of the cDNA sequence will be a "U".

An exemplary sequence encoding human RBM25 is as follows (the start and stop codons of the coding sequence are bold and underlined):

(SEQ ID NO: 1)

AGTGCACGCCGGGCAAGAGGAAGACCTCCATCAGCTCGCCGCGCAGCGC

GGCTGTATTTGCGGCCTGTGCGAGTAGGCGCTTGGGCACTCAGTCTCCC

TGGCGAGCGACGGGCAGAAATCTCGAACCAGTGGAGCGCACTCGTAACC

TGGATCCCAGAAGGTCGCGAAGGCAGTACCGTTTCCTCAGCGGCGGACT

GCTGCAGTAAGA<u>ATG</u>TCTTTTCCACCTCATTTGAATCGCCCTCCCATGG

GAATCCCAGCACTCCCACCAGGGATCCCACCCCCGCAGTTTCCAGGATT

TCCTCCACCTGTACCTCCAGGGACCCCAATGATTCCTGTACCAATGAGC

ATTATGGCTCCTGCTCCAACTGTCTTAGTACCCACTGTGTCTATGGTTG

GAAAGCATTTGGGCGCAAGAAAGGATCATCCAGGCTTAAAGGCTAAAGA

AAATGATGAAAATTGTGGTCCTACTACCACTGTTTTTGTTGGCAACATT

TCCGAGAAAGCTTCAGACATGCTTATAAGACAACTCTTAGCTAAATGTG

GTTTGGTTTTGAGCTGGAAGAGAGTACAAGGTGCTTCCGGAAAGCTTCA

AGCCTTCGGATTCTGTGAGTACAAGGAGCCAGAATCTACCCTCCGTGCA

CTCAGATTATTACATGACCTGCAAATTGGAGAGAAAAAGCTACTCGTTA

AAGTTGATGCAAAGACAAAGGCACAGCTGGATGAATGGAAAGCAAAGAA

-continued

GAAAGCTTCTAATGGGAATGCAAGGCCAGAAACTGTCACTAATGACGAT

GAAGAAGCCTTGGATGAAGAAACAAAGAGGAGAGATCAGATGATTAAAG

GGGCTATTGAAGTTTTAATTCGTGAATACTCCAGTGAGCTAAATGCCCC

CTCACAGGAATCTGATTCTCACCCCAGGAAGAAGAAGAAGGAAAAGAAG

GAGGACATTTTCCGCAGATTTCCAGTGGCCCCACTGATCCCTTATCCAC

TCATCACTAAGGAGGATATAAATGCTATAGAAATGGAAGAAGACAAAAG

AGACCTGATATCTCGAGAGATCAGCAAATTCAGAGACACACATAAGAAA

CTGGAAGAAGAGAAAGGCAAAAAGGAAAAAGAAAGACAGGAAATTGAGA

AAGAACGGAGAGAAAGAGAGAGGGAGCGTGAAAGGGAACGAGAAAGGCG

AGAACGGGAACGAGAAAGGGAAAGAGAACGTGAACGAGAAAAGGAGAAA

GAACGGGAGCGGGAACGAGAACGGGATAGGGACCGTGACCGGACAAAAG

AGAGAGACCGAGATCGGGATCGAGAGAGAGATCGTGACCGGGATAGAGA

AAGGAGCTCAGATCGTAATAAGGATCGCAGTCGATCAAGAGAAAAAAGC

AGAGATCGTGAAAGGGAACGAGAGCGGGAAAGAGAGAGAGAGAGAGAAC

GAGAGCGAGAACGAGAACGGGAGCGAGAGAGAGAGCGAGAGAGGGAACG

GGAGCGAGAAAGAGAAAAAGACAAAAAACGGGACCGAGAAGAAGATGAA

GAAGATGCATACGAACGAAGAAAACTTGAAAGAAAACTCCGAGAGAAAG

AAGCTGCTTATCAAGAGCGCCTTAAGAATTGGGAAATCAGAGAACGAAA

GAAAACCCGGGAATATGAGAAAGAAGCTGAAAGAGAAGAAGAAAGAAGA

AGAGAAATGGCCAAAGAAGCTAAACGACTAAAAGAATTCTTAGAAGACT

ATGATGATGATAGAGATGACCCCAAATATTACAGAGGAAGTGCTCTTCA

GAAAAGGTTGCGTGATAGAGAAAAGGAAATGGAAGCAGATGAACGAGAT

AGGAAGAGAGAGAGAAGGAGGAGCTTGAGGAAATCAGGCAGCGCCTTCTGG

CAGAAGGGCATCCAGATCCAGATGCAGAGCTCCAGAGGATGGAACAAGA

GGCTGAGAGGCGCAGGCAGCCACAAATAAAGCAAGAGCCAGAATCAGAA

GAGGAGGAAGAAGAAAAGCAAGAAAAAGAAGAAAAACGAGAAGAACCCA

TGGAAGAGGAAGAGGAGCCAGAGCAAAAGCCTTGTCTGAAACCTACTCT

GAGGCCCATCAGCTCTGCTCCATCTGTTTCCTCTGCCAGTGGCAATGCA

ACACCTAACACTCCTGGGGATGAGTCTCCCTGTGGTATTATTATTCCTC

ATGAAAACTCACCAGATCAACAGCAACCTGAGGAGCATAGGCCAAAAAT

AGGACTAAGTCTTAAACTGGGTGCTTCCAATAGTCCTGGTCAGCCTAAT

TCTGTGAAGAGAAAGAAACTACCTGTAGATAGTGTCTTTAACAAATTTG

AGGATGAAGACAGTGATGACGTACCCCGAAAAAGGAAACTGGTTCCCTT

GGATTATGGTGAAGATGATAAAAATGCAACCAAAGGCACTGTAAACACT

GAAGAAAAGCGTAAACACATTAAGAGTCTCATTGAGAAAATCCCTACAG

CCAAACCTGAGCTCTTCGCTTATCCCCTGGATTGGTCTATTGTGGATTC

TATACTGATGGAACGTCGAATTAGACCATGGATTAATAAGAAAATCATA

GAATATATAGGTGAAGAAGAAGCTACATTAGTTGATTTTGTTTGTTCTA

AGGTTATGGCTCATAGTTCACCCCAGAGCATTTTAGATGATGTTGCCAT

GGTACTTGATGAAGAAGCAGAAGTTTTTATAGTCAAAATGTGGAGATTA

-continued

TTGATATATGAAACAGAAGCCAAGAAAATTGGTCTTGTGAAGTAAAACT

TTTTATATTTAGAGTTCCATTTCAGATTTCTTCTTTGCCACCCTTTTAA

GGACTTTGAATTTTTCTTTGTCTTTGAAGACATTGTGAGATCTGTAATT

TTTTTTTTTGTAGAAAATGTGAATTTTTTGGTCCTCTAATTTGTTGTT

GCCCTGTGTACTCCCTTGGTTGTAAAGTCATCTGAATCCTTGGTTCTCT

TTATACTCACCAGGTACAAATTACTGGTATGTTTTATAAGCCGCAGCTA

CTGTACACAGCCTATCTGATATAATCTTGTTCTGCTGATTTGTTTCTTG

TAAATATTAAAACGACTCCCCAATTATTTTGCAGAATTGCACTTAATAT

TGAAATGTACTGTATAGGAACCAACATGAACAATTTTAATTGAAAACAC

CAGTCATAAACTATTACCACCCCCACTCTCTTTTGATCAGAAATGGCAA

GCCCTTGTGAAGGCATGGAGTTTAAAATTGGAATGCAAAAATTAGCAGA

CAATCCATTCCTACTGTATTTCTGTATGAATGTGTTTGTGAATGTATGT

GTAAAAGTCTTTCTTTTCCCTAATTTGCTTTGGTGGGGTCCTTAAAACA

TTTCCCAACTAAAGAATAGAATTGTAAAGGAAAAGTGGTACTGTTCCAA

CCTGAAATGTCTGTTATAATTAGGTTATTAGTTTCCCAGAGCATGGTGT

TCTCGTGTCGTGAGCAATGTGGTTTGCTAACTGGATGGGGTTTTCTTAT

TAATAAGATGGCTGCTTCAGCTTCTCTTTTAAAGGAATGTGGATCATAG

TGATTTTTCCTTTTAATTTTATTGCTCAGAAATGAGGCATATCCTAAAA

ATCCTGGAGAGCTGTATTTAATGCATTTTTGCACTAATTGGTCCTTAGT

TTAATTCTATTGTATCTGTTTATTTAACAAAAAATTCATCATACCAAAA

AGTGTAAGTGAAAACCCCCTTTAAAACAAAACAAAAAAATGAAATAAAA

TTAGGCAAATTGACAGACAGTGAGAGTTTTACAAACATGATAGGTATTC

TGCTCGGCAATTTGTAAGTTTACATGTTATTTAAGGATAAAGGTAAATC

ATTCAAGGCAGTTACCAACCACTAACTATTTGTTTTCATTTTTGTCTTG

TAGAAGGTTTATATCTTGTTTTACCTTGGCTCATTAGTGTTTAAAAATG

TACTGATGATGTGCTTAGAGAAATTCCTGGGGCTTTCTTCGTTGTAGAT

CAGAATTTCACCAGGGAGTAAAATTACCTGAAAACGTAAGAAGTTTTAA

ACAGCTTTTCACACAAATTAGATGCAACTGTTCCCATGTCTGAGTACTT

ATTTAAAAGAAAGGTAAAGATTGGCCTGTTAGAAAAAGCATAATGTGAG

CTTTGGATTACTGGATTTTTTTTTTTTTTTAAACACACCTGGAGAGGACA

TTTGAAAACACTGTTCTTACCCTCGAACCCTGATGTGGTTCCATTATGT

AAATATTTCAAATATTAAAAATGTATATATTTGATCCTGGGGACTCATA

TTCTTTCAGAATCATGTAAATAAATGGCATCATGTTGTAA

An exemplary sequence encoding for human LUC7L3 is as follows:

(SEQ ID NO: 2)

ACGGCATGCTGGGAAGGCGTCCGCGCGGCGGCCATTTTGTCTTGTCGGC

TCCTGTGTGTAGGAGGGATTTCGGCCTGAGAGCGGGCCGAGGAGATTGG

CGACGGTGTCGCCCGTGTTTTCGTTGGCGGGTGCCTGGGCTGGTGGGAA

CAGCCGCCCGAAGGAAGCACCATGATTTCGGCCGCGCAGTTGTTGGATG

AGTTAATGGGCCGGGACCGAAACCTAGCCCCGGACGAGAAGCGCAGCAA

-continued

CGTGCGGTGGGACCACGAGAGCGTTTGTAAATATTATCTCTGTGGTTTT
TGTCCTGCGGAATTGTTCACAAATACACGTTCTGATCTTGGTCCGTGTG
AAAAAATTCATGATGAAAATCTACGAAAACAGTATGAGAAGAGCTCTCG
TTTCATGAAAGTTGGCTATGAGAGAGATTTTTTGCGATACTTACAGAGC
TTACTTGCAGAAGTAGAACGTAGGATCAGACGAGGCCATGCTCGTTTGG
CATTATCTCAAAACCAGCAGTCTTCTGGGGCCGCTGGCCCAACAGGCAA
AAATGAAGAAAAAATTCAGGTTCTAACAGACAAAATTGATGTACTTCTG
CAACAGATTGAAGAATTAGGGTCTGAAGGAAAAGTAGAAGAAGCCCAGG
GGATGATGAAATTAGTTGAGCAATTAAAAGAAGAGAGAGAACTGCTAAG
GTCCACAACGTCGACAATTGAAAGCTTTGCTGCACAAGAAAAACAAATG
GAAGTTTGTGAAGTATGTGGAGCCTTTTTAATAGTAGGAGATGCCCAGT
CCCGGGTAGATGACCATTTGATGGGAAAACAACACATGGGCTATGCCAA
AATTAAAGCTACTGTAGAAGAATTAAAAGAAAAGTTAAGGAAAAGAACC
GAAGAACCTGATCGTGATGAGCGTCTAAAAAAGGAGAAGCAAGAAAGAG
AAGAAAGAGAAAAAGAACGGGAGAGAGAAAGGGAAGAAAGAGAAAGGAA
AAGACGAAGGGAAGAGGAAGAAAGAGAAAAAGAAAGGGCTCGTGACAGA
GAAAGAAGAAAGAGAAGTCGTTCACGAAGTAGACACTCAAGCCGAACAT
CAGACAGAAGATGCAGCAGGTCTCGGGACCACAAAAGGTCACGAAGTAG
AGAAAGAAGGCGGAGCAGAAGTAGAGATCGACGAAGAAGCAGAAGCCAT
GATCGATCAGAAAGAAAACACAGATCTCGAAGTCGGGATCGAAGAAGAT
CAAAAAGCCGGGATCGAAAGTCATATAAGCACAGGAGCAAAAGTCGGGA
CAGAGAACAAGATAGAAAATCCAAGGAGAAAGAAAAGAGGGGATCTGAT
GATAAAAAAAGTAGTGTGAAGTCCGGTAGTCGAGAAAAGCAGAGTGAAG
ACACAAACACTGAATCGAAGGAAAGTGATACTAAGAATGAGGTCAATGG
GACCAGTGAAGACATTAAATCTGAAGGTGACACTCAGTCCAATTAAAAC
TGATCTGATAAGACCTCAGATCAGACAGAGGTAAGTGTATTGTTTCTCA
CTTTGATTAGGGCTTTTTGTTACTGTTTGACAGTGCAGCGTAAGTATGC
ACAGATGAAGATGGAACTAAGCCGAGTAAGAAGACATACAAAAGCCTCT
TCTGAAGGAAAAGACAGTGTAGTCCTGCAAAACATTTTGAGGTACATTG
TTTTGTCTCAGCTATTTTGTAGCAGACTCGTGCCCCCATTAGTGTGCCT
CTTTGGAAATTATCGCCCACATTTGTAATATAGTCGCCATTGAAAAGTT
AATTATCCTTTTTTTAGGGATTTTGATGTCATTTCTTTTTTTTTTTTAA
TAAAAAGGTTGAACTGTTTTTTTTTTTCTTTTTGGTATTAAGTCCATCT
TGTGTTGGTACATTGGCAGAGACATATGCTTTAAAAACTTAAATATTTC
GGAGGCACATGTTGGACTACTTTGTTTTAATTAAACTGCTAGTATTTCT
TTGTCAAGGATGTTTCTAGTTTTTTGCTTTATTGCCTTGCATTCTAATG
CAGTTTGTTCTGTAACTCGAGAGCCAGTAGCATTGGATTGATGGAAGTG
TAGGGTTTATGAATTATTGCAGCTGACTACCATACCTCACACAGCGTTG
GTGTTGTGAGCGGCCCATGAAAAGCCAAATTAAAAATCAAGGATTCAGT
CAAACTAAGCAGGTACTCATGCCAGGTACTCCTTTCTCTACCCACATCC

-continued

ATGTTTGAATGCTATTGCCTGTGATCTTTACGCTTAACTGTTGTGTATC
TTTTTTGTTCTTTACAAGAAGTGCAGAGGGGTTTTTTGTGTATTGCGTG
AAAACTTATAAAACAAATGTTAACAGAATGGAATTTTTTTCAACTGTA
TGTAGGGCTGCAGTGGTGGCCAGAATTAGATATCTTTAAAGAATTTTAA
ATACAATAAACACTTCATATTATTCGCCTTGTTACACTCAATGCAATTC
TCAAGTCTATAAGAGGTATGTGCTTAATATTTCCTACTGTGTAGGAGAA
TTTGCAGTCAGCCATAGGTATGTAGGAATAGTCACTCACTGGCTGATAC
ATTTAAAGCAGCAGTGTGAATAGCAAGGACAGACACCTTCAATTTGTGA
AATCAAAGAACTGATGCACTATATAGAACGAATTTGGGTTTTTAAAGAA
ATATTAAAAGTTAGGTACTGTAAGTGTTCTTAAAACCTGTAAACTTCAT
TCTGTGGGCTAGTGGTGTGGGACAAAATATTCCTAATGAAAGGAAGTAC
CAATTAGTTGATTTGTTGGTGGCATTCCCCTTTTGGGAAAGCAATGTAA
GGTTATGTCTGTGTATGTCATTCACACTTAGGCAAGCATACACAGGCAC
ATGGCTTTAAGAACCACACTGATGCCTTGATAATTAAAAAGAATACAAG
CATTCCATGTACACATGTTAATTAGCAGTTAGTGACTGGGCCAACACTT
TCTCATAAAAATTGGCCTTTTACATGTTGTCTAATTATCATTTTTCCCC
AAATTTTGCGTTGTAGGACTACTGTTCGAAGATTTTTGGAAGAATACTG
AGAACGGCATAAAGTGAAGATCGACATTTAAAAAATGAGGTGAAAGAAA
GCTATAGTGGCATAGAAAAAGTATAAAGCTCAGTTAGTTTTTTTATTAT
TATTATTATTAAAAGTTAATTCAGGACTGATGTGACCTACCAGATTTCA
GAACATGTGTTAATAGTATATATGCCACTGAAAACTTAGGTCCTGTATC
ATACTTTTTTCTTTAAGACTTTTTAAGAAATATTACTTAAACATGTGGC
TTGCTCAGTGTTTAATTGCAAGTTTTCAATCTTGGACTTTGAAAACAGG
ATTAAACGTTAGTATTCGTGTGAATCAGACTAAGTGGGATTTCATTTTT
ACAACTCTGCTCTACTTAGCCTTTGGATTTAGAAGTAAAAATAAAGTAT
CTCTGACTTTCTGTTACAAAGTTGATTGTCTCTGTCATTGAAAAGTTTT
AGTATTAATCTTTTTCTAATAAAGTTATTGACTCTGAAAAAAAAAA

In some embodiments, a prophylactic method of treating PH or PH-associated SCD in a subject is provided, the method comprising identifying the subject as being at risk for developing PH or dying from sudden cardiac death, and administering to the subject a compound that inhibits the activity of LUC7L3, RBM25, and/or PERK in an amount effective to prevent PH or SCD. In some embodiments, the method alternatively comprises the step of identifying an individual at risk of PH or SCD. In some embodiments, the method comprises identifying a subject at risk for developing PH or SCD. In such embodiments, the identifying comprises screening for the presence of an abnormal SCN5A splice variant in a test sample of the subject, wherein the presence of the abnormal splice variant identifies the subject as being at risk for developing PH, afflicted with PH, or suffering from SCD. For example, the presence of one or more of the SCN5A splice variants E28B (SEQ ID Nos: 6 and 7; Exon 28 shown as SEQ ID NO: 3), E28C (SEQ ID Nos: 8 and 9; Exon 28 shown as SEQ ID NO: 4) and/or E28D (SEQ ID Nos: 10 and 11; Exon 28 shown as SEQ ID NO: 5) in the test sample identifies the subject as being at risk for developing PH or suffering from SCD. The screening step, in some embodiments, comprises obtaining a test sample from the subject and analyzing nucleic acid from the sample for the presence of an abnormal splice variant.

The level of abnormal SCN5A splice variants in a test sample, in some embodiments, is analyzed to monitor efficacy of treatment, with a decrease in the level of abnormal SCN5A splice variants in the sample indicating effective therapy.

In some embodiments, the method to monitor efficacy of treatment comprises determining a level of abnormal SCN5A splice variants in a test sample of a subject before and after treatment with a compound that inhibits activity of LUC7L3, RBM25, and/or PERK. In such a method, a change in the level of abnormal SCN5A splice variants in the sample taken after treatment compared to the level of abnormal SCN5A splice variant in the sample before treatment indicates efficacy of treatment. A decrease in the level of abnormal SCN5A splice variants in the second test sample (e.g., post-treatment) compared to the level of abnormal SCN5A splice variants in the first test sample (e.g., prior to treatment or from an individual known not to suffer from the condition being treated) indicates a degree of effective therapy.

Alternatively, the level of full-length SCN5A in a test sample post-treatment is analyzed to monitor efficacy of treatment, with an increase in the level of full-length SCN5A in the sample indicates effective therapy.

In some embodiments, the method to monitor efficacy of treatment comprises determining a level of full-length SCN5A in a test sample of a subject before and after treatment with a compound that inhibits activity of LUC7L3, RBM25, and/or PERK. In such a method, a change in the level of full-length SCN5A in the sample taken after treatment compared to the level of full-length SCN5A in the sample before treatment indicates efficacy of treatment. An increase in the level of full-length SCN5A in the second test sample (e.g., post-treatment) compared to the level of full-length SCN5A in the first test sample (e.g., prior to treatment or from an individual known not to suffer from the condition being treated) indicates a degree of effective therapy.

Aspects of the present subject matter provide a method for diagnosing pulmonary hypertension (PH) in a subject in need thereof comprising (a) providing a test sample from said subject, wherein said test sample comprises a circulating cell or a bodily fluid;

(b) assaying the level of a full-length SCN5A protein, a full-length SCN5A protein-encoding mRNA, a SCN5A splice variant protein, or a SCN5A splice variant protein-encoding mRNA in the test sample; and (c) diagnosing the subject with PH if (i) the level of the full-length SCN5A protein or full-length SCN5A protein-encoding mRNA is reduced in the subject compared to a normal control, or (ii) the level of the SCN5A splice variant protein or mRNA encoding the SCN5A splice variant is increased compared to a normal control.

In some embodiments, (i) the level of the full-length SCN5A protein or full-length SCN5A protein-encoding mRNA is reduced in the subject compared to a normal control, or (ii) the level of the SCN5A splice variant protein or mRNA encoding the SCN5A splice variant is increased compared to a normal control indicates a diagnosis of PH.

In some embodiments, the subject is diagnosed with PH if (i) the level of the full-length SCN5A protein or full-length SCN5A protein-encoding mRNA is at least about 5%, 10%, 15%, 20%, 25%, 30%, 35%, 40%, 45%, 50%, 5-50%, 1-fold, 2-fold, 3-fold, or 4-fold lower in the subject compared to a normal control, or (ii) the level of the SCN5A splice variant protein or mRNA encoding the SCN5A splice variant is at least about 5%, 10%, 15%, 20%, 25%, 30%, 35%, 40%, 45%, 50%, 5-50%, 1-fold, 2-fold, 3-fold, or 4-fold greater in the subject compared to a normal control.

Aspect of the present subject matter provide a method for identifying whether a subject is at risk of developing PH, comprising (a) providing a test sample from said subject, wherein said test sample comprises a circulating cell or a bodily fluid;

(b) assaying the level of a full-length SCN5A protein, a full-length SCN5A protein-encoding mRNA, a SCN5A splice variant protein, or a SCN5A splice variant protein-encoding mRNA in the test sample;

(c) identifying the subject as at risk of developing PH if (i) the level of the full-length SCN5A protein or full-length SCN5A protein-encoding mRNA is reduced in the subject compared to a normal control, or (ii) the level of the SCN5A splice variant protein or mRNA encoding the SCN5A splice variant is increased compared to a normal control.

In some embodiments, the subject has a mean pulmonary arterial pressure (mPAP) less than about 17, 18, 19, 20, 21, 22, 23, 24, 25 or 17-25 mmHg at rest and/or a pulmonary capillary wedge pressure (PCWP) or left ventricular end-diastolic pressure greater than about 15, 16, 17, or 18 mmHg and/or a pulmonary vascular resistance (PVR) equal to or less than about 3, 2.5, or 2 Wood units.

In some embodiments, the normal control is the level in an individual or individuals having a mPAP of about 13, 14, 15, 16 or 14-16, and/or a PCWP or left ventricular end-diastolic pressure of about 3, 4, 5, 6, 7, 8, 9, 0, 11, 12, or 3-12 mmHg, and/or a PVR of about 0.25, 0.5, 1.0, 1.5, 1.6 or 0.25-1.6 Wood units.

In some embodiments, the subject is identified as at risk of developing PH if the level of the full-length SCN5A protein or full-length SCN5A protein-encoding mRNA is at least about 5%, 10%, 15%, 20%, 25%, 30%, 35%, 40%, 45%, 50%, 5-50%, 1-fold, 2-fold, 3-fold, or 4-fold lower in the subject compared to a normal control, or if the level of the SCN5A splice variant protein or mRNA encoding the SCN5A splice variant is at least about 5%, 10%, 15%, 20%, 25%, 30%, 35%, 40%, 45%, 50%, 5-50%, 1-fold, 2-fold, 3-fold, or 4-fold greater in the subject compared to a normal control.

Aspect of the present subject matter provide a method for monitoring whether PH is progressing in a subject who has been diagnosed with PH, comprising periodically determining the level of a full-length SCN5A protein, a full-length SCN5A protein-encoding mRNA, a SCN5A splice variant protein, or a SCN5A splice variant protein-encoding mRNA in the subject, and (1) identifying the PH as worsening if (i) the level of the full-length SCN5A protein or full-length SCN5A protein-encoding mRNA in the subject decreases over time, or (ii) the level of the SCN5A splice variant protein or the SCN5A splice variant protein-encoding mRNA increases over time;

(2) identifying the PH as improving if (i) the level of the full-length SCN5A protein or full-length SCN5A protein-encoding mRNA in the subject increases over time, or (ii) the level of the SCN5A splice variant protein or the SCN5A splice variant protein-encoding mRNA decreases over time; or (3) identifying the PH as neither worsening nor improving if (i) the level of the full-length SCN5A protein or full-length SCN5A protein-encoding mRNA in the subject remains the same over time, or (ii) the level of the SCN5A splice variant protein or the SCN5A splice variant protein-encoding mRNA remains the same over time, wherein determining the level of the full-length SCN5A protein, the full-length SCN5A protein-encoding mRNA, the SCN5A splice variant protein, or the SCN5A splice variant protein-encoding mRNA comprises (a) providing a test sample from said subject, wherein said test sample comprises a circulating cell or a bodily fluid; and (b) assaying the level of the full-length SCN5A protein, the full-length SCN5A protein-encoding mRNA, the SCN5A splice variant protein, or the SCN5A splice variant protein-encoding mRNA in the test sample.

In some embodiments, the level of the full-length SCN5A protein, the full-length SCN5A protein-encoding mRNA, the SCN5A splice variant protein, or the SCN5A splice variant protein-encoding mRNA is determined at least about 2, 3, 4, 5, 6, 7, 8, 9, 10 times or more.

In some embodiments, the level of the full-length SCN5A protein, the full-length SCN5A protein-encoding mRNA, the SCN5A splice variant protein, or the SCN5A splice variant protein-encoding mRNA is determined at least about every 1, 2, 3, 4, 5, 8, 9, 10, 25, or 52 weeks or about once every 1, 2, 3, or 4 months.

In some embodiments, the subject is receiving therapy for PH.

Aspects of the present subject matter provide a method for identifying whether a subject afflicted with PH is at risk of dying from sudden cardiac death (SCD), comprising (a) providing a test sample from said subject, wherein said test sample comprises a circulating cell or a bodily fluid;

(b) assaying the level of a full-length SCN5A protein, a full-length SCN5A protein-encoding mRNA, a SCN5A splice variant protein, or a SCN5A splice variant protein-encoding mRNA in the test sample; and (c) (1) comparing the level determined in (b) to a value in a database to identify the subject's absolute or relative risk of suffering from SCD, or (2) identifying the subject is at risk of suffering from SCD if (i) the full-length SCN5A protein or full-length SCN5A protein-encoding mRNA is at least about 5%, 10%, 15%, 20%, 25%, 30%, 35%, 40%, 45%, 50%, 5-50%, 1-fold, 2-fold, 3-fold, or 4-fold lower in the subject compared to a normal control, or (ii) the level of the SCN5A splice variant protein or the SCN5A splice variant protein-encoding mRNA is at least about 5%, 10%, 15%, 20%, 25%, 30%, 35%, 40%, 45%, 50%, 5-50%, 1-fold, 2-fold, 3-fold, or 4-fold greater in the subject compared to a normal control.

In some embodiments, the database contains (a) level values of full-length SCN5A protein, full-length SCN5A protein-encoding mRNA, SCN5A splice variant protein, or SCN5A splice variant protein-encoding mRNA from (i) subjects who have suffered from SCN5A, (ii) subjects who are afflicted with PH but who have not suffered from SCN5A, (iii) subjects afflicted with PH for at least about 1, 2, 3, 4, 5, 10, 15, or 20 years without suffering from SCN5A, and/or (iv) subjects who are not afflicted with PH, and/or (b) mean or median level values calculated using full-length SCN5A protein, full-length SCN5A protein-encoding mRNA, SCN5A splice variant protein, or SCN5A splice variant protein-encoding mRNA level values from (i) subjects who have suffered from SCN5A, (ii) subjects who are afflicted with PH but who have not suffered from SCN5A, (iii) subjects afflicted with PH for at least about 1, 2, 3, 4, 5, 10, 15, or 20 years without suffering from SCN5A, and/or (iv) subjects who are not afflicted with PH.

In some embodiments, the method further comprises administering a prophylactic treatment to the subject if the subject is identified as being at risk of suffering from SCD.

In some embodiments, the method further comprises directing the subject to obtain additional screening for SCD risk based on the level of the full-length SCN5A protein, full-length SCN5A protein-encoding mRNA, SCN5A splice variant protein, or SCN5A splice variant protein-encoding mRNA in the test sample.

Aspects of the present subject matter provide a method of prophylaxis for SCD, comprising identifying a subject at risk of suffering from SCD and administering to the subject a prophylactic treatment for SCD.

In some embodiments, the prophylactic treatment for SCD comprises administration of an antiarrhythmic drug, an angiotensin converting enzyme inhibitor (ACE), an angiotensin II receptor blocker, a beta-blocker, digoxin, a diuretic, a blood vessel dilator, an aldactone inhibitor, or a calcium channel blocker to the subject.

In some embodiments, the prophylactic treatment for SCD comprises implantation of a cardioverter-defibrillator (ICD) or surgery to repair or replace a mitral valve or an aortic valve in the subject.

Aspects of the present subject matter provide a method for adjusting the dose of a compound administered to a subject during therapy for PH, comprising periodically determining the level of a full-length SCN5A protein, a full-length SCN5A protein-encoding mRNA, a SCN5A splice variant protein, or a SCN5A splice variant protein-encoding mRNA in the subject, and (1) increasing the dose of the compound if (i) the level of the full-length SCN5A protein or full-length SCN5A protein-encoding mRNA in the subject decreases over time, or (ii) the level of the SCN5A splice variant protein or the SCN5A splice variant protein-encoding mRNA increases over time;

(2) increasing, maintaining, or reducing the dose or frequency of administration of the compound if (i) the level of the full-length SCN5A protein or full-length SCN5A protein-encoding mRNA in the subject increases over time, or (ii) the level of the SCN5A splice variant protein or the SCN5A splice variant protein-encoding mRNA decreases over time; or (3) increasing or maintaining the dose or frequency of administration of the compound if (i) the level of the full-length SCN5A protein or full-length SCN5A protein-encoding mRNA in the subject remains the same over time, or (ii) the level of the SCN5A splice variant protein or the SCN5A splice variant protein-encoding mRNA remains the same over time, wherein determining the level of the full-length SCN5A protein, the full-length SCN5A protein-encoding mRNA, the SCN5A splice variant protein, or the SCN5A splice variant protein-encoding mRNA comprises (a) providing a test sample from said subject, wherein said test sample comprises a circulating cell or a bodily fluid; and (b) assaying the level of the full-length SCN5A protein, the full-length SCN5A protein-encoding mRNA, the SCN5A splice variant protein, or the SCN5A splice variant protein-encoding mRNA in the test sample.

In some embodiments, the therapy comprises administering the compound at least about 1, 2, 3, 4, 5, 6, 7, 8, 9, or 10 times per day, week, or month.

Aspects of the present subject matter provide a method for identifying whether a therapy has improved PH in a subject, comprising (a) providing a pre-therapy test sample from said subject;
(b) assaying a pre-therapy level of a full-length SCN5A protein, a full-length SCN5A protein-encoding mRNA, a SCN5A splice variant protein, or a SCN5A splice variant protein-encoding mRNA in the pre-therapy test sample;
(c) administering the therapy to the subject;
(d) providing a post-therapy test sample from said subject, wherein said test sample comprises a circulating cell or a bodily fluid;
(e) assaying a post-therapy level of the full-length SCN5A protein, the full-length SCN5A protein-encoding mRNA, the SCN5A splice variant protein, or the SCN5A splice variant protein-encoding mRNA in the post-therapy test sample; and
(f) identifying the therapy as having improved PH in the subject if (i) the pre-therapy level of the full-length SCN5A protein or the full-length SCN5A protein-encoding mRNA is lower than the post-therapy level of the full-length SCN5A protein or the full-length SCN5A protein-encoding mRNA, or (ii) the pre-therapy level of the SCN5A splice variant protein or the SCN5A splice variant protein-encoding mRNA is higher than the post-therapy level of the SCN5A splice variant protein or the SCN5A splice variant protein-encoding mRNA.

In some embodiments, the PH is pulmonary arterial hypertension (PAH).

In some embodiments, the SCN5A splice variant is E28B, E28C and/or E28D.

In some embodiments, the SCN5A splice variant is two or more splice variants, and the two or more splice variants comprise one or more of E28B, E28C, and E28D.

In some embodiments, the method further comprises determining the level of one or more of HIF-1α, AngII, LUC7L3, RBM25, and/or PERK in the test sample.

In some embodiments, the method further comprises assaying whether the subject has mitochondrial aerobic glycolysis.

In some embodiments, assaying whether the subject has mitochondrial aerobic glycolysis comprises 2-deoxy-2($^{18}F$) flouro-D-glucose positron emission tomography (FDG-PET).

In some embodiments, assaying the level of the full-length SCN5A protein, the full-length SCN5A protein-encoding mRNA, the SCN5A splice variant protein, or the SCN5A splice variant protein-encoding mRNA comprises contacting the full-length SCN5A protein, the full-length SCN5A protein-encoding mRNA, the SCN5A splice variant protein, or the SCN5A splice variant protein-encoding mRNA with a SCN5A-specific binding agent.

In some embodiments, the binding agent comprises an antibody or a fragment thereof, a detectable protein or a fragment thereof, or a nucleic acid molecule.

In some embodiments, the nucleic acid molecule comprises at least one probe or at least one primer.

In some embodiments, the assaying comprises a polymerase chain reaction (PCR), reverse transcription polymerase chain reaction (RT-PCR), quantitative PCR (qPCR), or a Northern Blot.

In some embodiments, assaying the level of the full-length SCN5A protein-encoding mRNA or the SCN5A splice variant protein-encoding mRNA comprises reverse-transcribing cDNA from the full-length SCN5A protein-encoding mRNA or the SCN5A splice variant protein-encoding mRNA.

In some embodiments, the binding agent comprises an antibody.

In some embodiments, the antibody comprises an anti-full-length SCN5A and/or an anti-SCN5A splice variant antibody.

In some embodiments, the antibody comprises conjugated to a detectable moiety.

In some embodiments, the antibody comprises a polyclonal antibody or a monoclonal antibody.

In some embodiments, said binding agent is attached to a solid support.

In some embodiments, said solid support comprises a strip, a multiwell plate, a microarray, a polymer, a bead, or a nanoparticle.

In some embodiments, the binding agent comprises a detectable moiety, and the detectable moiety comprises a fluorescent marker, a radioactive isotope, or a chemiluminescent compound.

In some embodiments, the detectable moiety comprises a fluorescent marker, and the fluorescent marker comprises fluorescein isothiocyanate, rhodamine, phycoerythrin, phycocyanin, allophycocyanin, p-phthaldehyde and fluorescamine, or $^{152}Eu$.

In some embodiments, the detectable moiety comprises a radioactive isotope, and the radioactive isotope is $^{125}$iodine, tritium, $^{75}$selenomethonine, or $^{64}$copper.

In some embodiments, the detectable moiety comprises a chemiluminescent compound, and the chemiluminescent compound is luminol, isoluminol, theromatic acridinium ester, imidazole, acridinium salt, or oxalate ester.

In some embodiments, the test sample comprises a circulating cell.

In some embodiments, the circulating cell comprises a peripheral blood mononuclear cell (PMBC).

In some embodiments, the test sample comprises plasma, whole blood, serum, saliva or urine.

In some embodiments, said test sample comprises serum.

In some embodiments, said test sample comprises a population of white blood cells or enriched white blood cells.

In some embodiments, said population comprises a buffy coat fraction of total white blood cells.

In some embodiments, said test sample comprises a monocyte.

In some embodiments, said circulating cell comprises a T-cell.

In some embodiments, said assaying comprises lysing the circulating cell.

In some embodiments, said assaying comprises an ELISA (enzyme-linked immunosorbent) assay, a Western blot, a mass spectrometry, a radioimmunoassay, or a fluoroimmunoassay.

In some embodiments, said assaying comprises a microarray.

Aspects of the present subject matter provide a kit comprising (a) an agent for detecting the level of a full-length SCN5A protein, a full-length SCN5A protein-encoding mRNA, a SCN5A splice variant protein, or a SCN5A splice variant protein-encoding mRNA for diagnosing PH, wherein the agent binds to the SCN5A protein or the mRNA encoding said protein, and yields a complex comprising (i) the full-length SCN5A protein, the full-length SCN5A protein-encoding mRNA, the SCN5A splice variant protein, or the SCN5A splice variant protein-encoding mRNA and (ii) said binding agent; and (b) instructions for using the agent for diagnosing PH.

In some embodiments, the kit further comprises reagents used to detect said complex.

In some embodiments, said agent is attached to a solid support.

In some embodiments, said solid support is a test strip or a microarray.

Aspects of the present subject matter provide a diagnostic test system comprising a collection or compilation of test results data representing levels of a marker in at least one test sample, a means for computing an index value from said marker, wherein the index value comprises a PH or a SCD risk score, and a means of reporting the index value.

In some embodiments, the marker comprises a full-length SCN5A protein, a full-length SCN5A protein-encoding mRNA, a SCN5A splice variant protein, or a SCN5A splice variant protein-encoding mRNA.

In some embodiments, the index value uses said marker measurement data, and wherein the index score is correlated with risk of developing PH or suffering from SCD.

In some embodiments, the test sample comprises a circulating cell, plasma, whole blood, serum, saliva, or urine.

Aspects of the present subject matter provide a diagnostic device comprising a solid support and a full-length SCN5A protein binding agent, a full-length SCN5A protein-encoding mRNA binding agent, a SCN5A splice variant protein binding agent, or a SCN5A splice variant protein-encoding mRNA binding agent immobilized on said support.

Aspects of the present subject matter provide a diagnostic device comprising a plurality of immobilized binding agents comprising a binding agent that binds to a SCN5A protein or a SCN5A-encoding mRNA, and one or more of (a) a binding agent that binds to a HIF-1α protein or HIF-1α-encoding mRNA, (b) a binding agent binds to a LUC7L3 protein or LUC7L3 protein-encoding mRNA, (c) a binding agent that binds to a RBM25 protein or a RBM25 protein-encoding mRNA, and (d) a binding agent that binds to a PERK protein or a PERK protein-encoding mRNA.

In certain embodiments, the subject does not comprise sleep apnea or renal disease (e.g. chronic renal disease). In some embodiments, the subject does not comprise obstructive sleep apnea, end stage renal disease, or hypertrophic cardiomyopathy.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DETAILED DESCRIPTION

Figure 1:
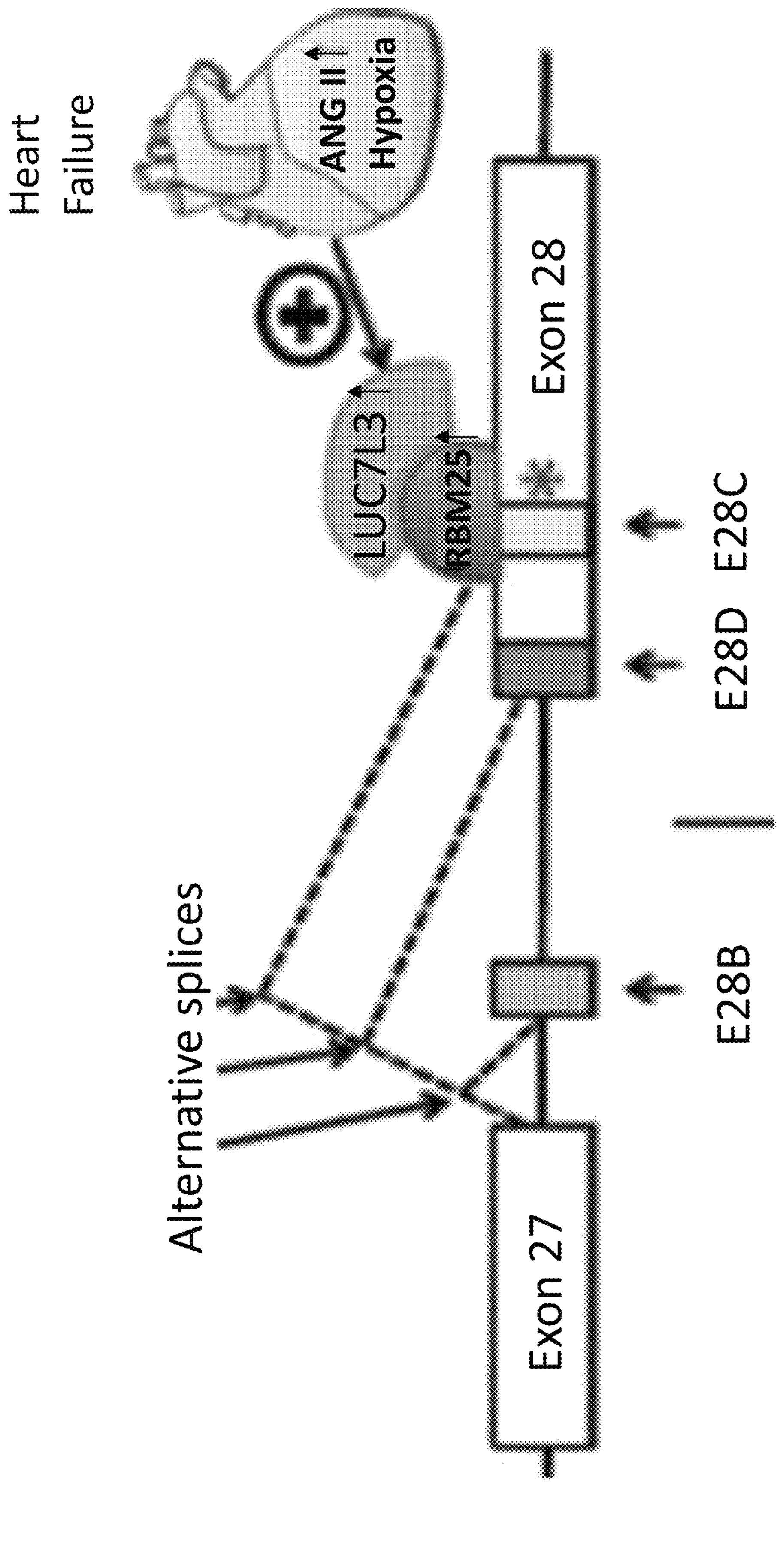
FIG. 1 is a diagram of SCN5A alternative splicing as mediated by hypoxia and Ang II in the setting of heart failure.

Patients with PAH are at increased risk for RV failure and SCD, but prior to the invention determinants of RV phenotype and mechanisms of SCD were unknown. Decreased expression of the cardiac sodium channel SCN5A is associated with left ventricular fibrosis and alternative splicing of SCN5A produces non-functioning splice variants (SVs), which have been implicated in mitochondrial stress, arrhythmogenesis, and sudden death in left heart failure. HIF-1α and Ang II, both of which are important in the pathogenesis of PAH, regulate alternative splicing; however SCN5A SVs have not been studied in PAH or RV failure.

As many as one quarter of deaths in PAH are due to SCD, and PAH patients monitored on telemetry prior to cardiac arrest have numerous arrhythmias (Kuriyama, Nihon Kyobu Shikkan Gakkai Zasshi. 1992; 30(1):3-11; Hoeper et al., Am J Respir Crit Care Med. 2002; 165(3):341-4). Hemodynamic burden does not accurately predict survival following cardiac arrest, and not all patients are of advanced functional class at the time of death, indicating a disconnect between common disease correlates and their ability to predict outcome (Hoeper et al., Am J Respir Crit Care Med. 2002; 165(3):341-4). Resuscitation of PAH patients is rarely successful, highlighting the critical need for risk stratification (Tonelli et al., Am J Respir Crit Care Med. 2013; 188(3): 365-9; Hoeper et al., Am J Respir Crit Care Med. 2002; 165(3):341-4) and preemptive treatment. The role of SCN5A in conduction abnormalities has been extensively studied in left heart failure and has been implicated in the pathogenesis of left ventricular fibrosis, cardiomyopathy, and SCD (Liu et al., Nat Rev Cardiol. 2014; 11(10):607-15). Systolic heart failure patients (patients having left heart disease/failure) have increased expression of SCN5A SV in their RVs, but whether this expression also pertains to patients with pulmonary vascular disease has not been studied. In addition to conduction abnormalities, alternative splicing has been linked to mitochondrial stress and metabolic changes via the UPR. Oxidative stress, abnormal mitochondrial respiration and the UPR are tied to cardiac arrthythmogenesis (Rutledge and Dudley, Expert Rev Cardiovasc Ther. 2013; 11(7):799-801; Liu and Dudley, Int J Mol Sci. 2016; 17(1)). While RV glycolytic shift has been described in PAH, RV phenotypes are not well understood even though the RV is a major determinant of outcome in PAH.

Abnormal intimal proliferation of the cardiac conduction system has been demonstrated at autopsy in PAH, implicating conduction abnormalities as a cause of death (James, Ann Intern Med. 1962; 56:252-64). The cardiac sodium channel SCN5A is responsible for the fast depolarization phase 0 of the cardiac action potential. Mutations in the encoding gene Nav1.5 lead to a wide spectrum of arrhythmogenic conditions including Brugada syndrome and long QT syndrome (Liu et al., Nat Rev Cardiol. 2014; 11(10):607-15). Resultant cardiac conduction disease can be traced to the RV outflow tract and SCN5A mutations have also been associated with structural changes including dilated cardiomyopathy (Meregalli et al., Cardiovasc Res. 2005; 67(3):367-78; Lambiase et al., Circulation. 2009; 120(2):106-17, 1-4; Lakdawala et al., Circ Arrhythm Electrophysiol. 2013; 6(1):228-37). Haploinsufficient mouse models show increased collagen deposition and fibrosis in ventricular tissue, thus demonstrating morphologic changes from deficient SCN5A in addition to electrophysiologic disturbances (Jeevaratnam et al., Acta Physiol (Oxf). 2016; 216(2):186-202; Jeevaratnam et al., Mech Ageing Dev. 2012; 133(9-10):591-9; Zhang et al., Acta Physiol (Oxf). 2014; 211(4):559-73).

Alternative splicing is a process by which a single gene can encode multiple distinct proteins (SVs) through transcription of particular combinations of exons, as regulated by splicing factors (SF). Alternative splicing of SCN5A is increased in the left ventricle in systolic heart failure, and produces SV (E28B, E28C and E28D) which are truncated, non-functioning channels with significantly reduced sodium current that may predispose patients to SCD (FIG. 1) (Gao et al., Circulation. 2011; 124(10):1124-31; Gao et al., Circ Arrhythm Electrophysiol. 2013; 6(5):1018-24; Shang et al., Circ Res. 2007; 101(11):1146-54). HIF-1α and the renin angiotensin system (RAS) via Ang II mediate the production of two SF, RBM25 and LUC7L3. Both of these SF influence alternative splicing of SCN5A to decrease expression of full length SCN5A and to produce SV which can be detected in WBC from peripheral blood (FIG. 2) (Gao et al., Circulation. 2011; 124(10):1124-31). Circulating mRNA levels of SF and SV have been shown to act as surrogates for fold changes in left ventricular tissue, and may act as a powerful point-of-care assay for SCD (Gao et al., Circulation. 2011; 124(10):1124-31; Gao et al., J Am Coll Cardiol. 2014; 63(21):2261-9).

In addition to direct electrochemical consequences, SV are trapped and accumulate in the endoplasmic reticulum (ER) and trigger the UPR, which can lead to pan downregulation of cellular protein synthesis including other ion conducting channels important for conduction (Gao et al., Circ Arrhythm Electrophysiol. 2013; 6(5):1018-24). Additionally, the UPR may have more global consequences including mitochondrial stress and cellular metabolic changes and apoptosis (Gao et al., Circ Arrhythm Electrophysiol. 2013; 6(5):1018-24; Rainbolt et al., Trends Endocrinol Metab. 2014; 25(10):528-37). The two identified triggers for alternative splicing of SCN5A, HIF-1α and RAS, are also implicated in pulmonary vascular disease pathogenesis (Morrell et al., Cardiovasc Res. 1997; 34(2):393-403; Morrell et al., Am J Physiol. 1995; 269:H1186-94; Zhang et al., Am J Physiol Lung Cell Mol Physiol. 2009; 297(4):10) and HIF-1α induces glycolytic metabolism in the RV of PAH patients demonstrated by increased FDG-PET uptake, however the mechanism underlying this relationship is heretofore unknown (Lundgrin et al., Ann Am Thorac Soc. 2013; 10(1):1-9). HIF-1α-driven alternative splicing of SCN5A with resultant mitochondrial dysfunction (via the UPR) as a contributor to RV phenotypic changes in PAH has not been explored.

PAH patients show higher SV to full length SCN5A mRNA levels than matched controls and SV mRNA is increased at baseline as compared to follow-up on PAH treatment.

The surprising link between SCN5A alternative splicing and RV PAH phenotypes support point-of-care assays for risk stratification in subjects afflicted with PAH (a progressive and often fatal disease). Aspects of the present subject matter provide a blood test to predict SCD risk and to determine the need for, e.g., an implanted defibrillator. Also provided is a blood test to determine disease and reduced heart function severity in subjects afflicted with PAH.

SCN5A (Sodium Channel, Voltage Gated, Type V Alpha Protein)

Cardiac voltage-gated $Na^+$ (Nav) channels have a heteromeric assembly of pore-forming a subunit and auxiliary β subunits that modulate channel functions. Nav1.5 (SCN5A) is the major Nav α subunit expressed in the mammalian myocardium, whereas multiple Nav β subunits have been described in cardiomyocytes. Voltage-gated $Na^+$ channels play a critical role in the membrane excitability of cardiomyocytes by generating the rapid upstroke of the action potential. Additionally, Nay channels govern the impulse conduction velocity in the myocardium. Abnormal cardiac $Na^+$ channel function has been associated in hereditary cardiac diseases such as long QT syndrome (LQTS), Brugada syndrome, and progressive cardiac conduction defect, as well as acquired cardiac conditions including myocardial ischemia and heart failure.

Alternative splicing of SCN5A has not been connected with right heart failure or PAH.

The present subject matter provides methods that comprise the step of determining a level of a full length transcript of SCN5A gene or of a splice variant of the SCN5A gene. A decreased level of the full length transcript of the SCN5A gene indicates a diagnosis of PAH, increased severity of PAH, and an increased risk for sudden cardiac death. In exemplary aspects, a level of a splice variant of the SCN5A gene is determined, and an increased level of the splice variant indicates a diagnosis of PAH, increased severity of PAH, and an increased risk for SCD. In specific aspects, the splice variant of the SCN5A gene is a splice variant produced from alternative splicing within Exon 28 of the SCN5A gene. In specific aspects, the splice variant is a SCN5A Exon 28 B splice variant (a.k.a., E28B; Exon 28 shown as SEQ ID NO: 3), a SCN5A Exon 28 C splice variant (a.k.a., E28C; Exon 28 shown as SEQ ID NO: 4), or a SCN5A Exon 28 D splice variant (a.k.a., E28D; Exon 28 shown as SEQ ID NO: 5).

The level may be an expression level of a full length transcript of SCN5A gene or of a splice variant of the SCN5A gene. Suitable methods of determining expression levels of transcripts of a gene are include direct methods of determining levels of transcripts (e.g., quantitative PCR) and indirect methods of determining levels of transcripts (e.g., Western blotting for translated protein or peptide products of the transcripts). The level may be an activity level of a full-length transcript of the SCN5A gene that is determined via measurement, e.g., measurement of the sodium current.

Exon 28 of SCN5A splice variant Exon 28 B (E28B)

```
                                                      (SEQ ID NO: 3)
ggagccctcc tagtgagtat gaagtgatat ctcactgagg ttttggtttg caaaagcaaa    60

tgactgatga ctaacgatgc aggacatctt tccatgtgca tgttggtcat ttatatatct   120

tccttggaga aatctctatt cagatcctta gctcattttt aattgggtta tttctcttct   180

tcttgttgag ttgtaagagt tctttacata ttctggatca cagtctctta tcagatatat   240

gatttaaaaa tattttctcc tagtctgtga gtttttttcat ttcctagtgg tgtccattaa   300

agcacaaaag ttttacatgt t                                             321
```

Exon 28 of SCN5A splice variant Exon 28 C (E28C)

```
                                                      (SEQ ID NO: 4)
gaactgcaca atgaccagca ggaggggaga agagagtagg aaaaaggagg gaaggacaga    60

catcaagtgc cagatgttgt ctgaactaat cgagcacttc tcaccaaact tcatgtataa   120

ataaaataca tatttttaaa acaaaccaat aaatggctta catg                    164
```

Exon 28 of SCN5A splice variant Exon 28 D (E28D)

```
                                                      (SEQ ID NO: 5)
ggcactgtgc tctcggacat catccagaag tacttcttct ccccgacgct cttccgagtc    60

atccgcctgg cccgaatagg ccgcatcctc agactgatcc gaggggccaa gggg         114
```

E28B SCN5A Splice Variant Complete Nucleotide Sequence (the portion of the sequence that is different from wild-type is bolded and underlined):

```
                                                      (SEQ ID NO: 6)
  1 agacggcggc ggcgcccgta ggatgcaggg atcgctcccc cggggccgct gagcctgcgc

 61 ccagtgcccc gagccccgcg ccgagccgag tccgcgccaa gcagcagccg cccaccccgg

121 ggcccggccg ggggaccagc agcttcccca caggcaacgt gaggagagcc tgtgcccaga

181 agcaggatga gaagatggca aacttcctat tacctcgggg caccagcagc ttccgcaggt

241 tcacacggga gtccctggca gccatcgaga agcgcatggc agagaagcaa gcccgcggct

301 caaccacctt gcaggagagc cgagaggggc tgcccgagga ggaggctccc cggccccagc

361 tggacctgca ggcctccaaa aagctgccag atctctatgg caatccaccc caagagctca

421 tcggagagcc cctggaggac ctggacccct tctatagcac ccaaaagact ttcatcgtac
```

-continued

```
 481 tgaataaagg caagaccatc ttccggttca gtgccaccaa cgccttgtat gtcctcagtc
 541 ccttccaccc catccggaga gcggctgtga agattctggt tcactcgctc ttcaacatgc
 601 tcatcatgtg caccatcctc accaactgcg tgttcatggc ccagcacgac cctccaccct
 661 ggaccaagta tgtcgagtac accttcaccg ccatttacac ctttgagtct ctggtcaaga
 721 ttctggctcg aggcttctgc ctgcacgcgt tcactttcct tcgggaccca tggaactggc
 781 tggactttag tgtgattatc atggcataca caactgaatt tgtggacctg ggcaatgtct
 841 cagccttacg caccttccga gtcctccggg ccctgaaaac tatatcagtc atttcagggc
 901 tgaagaccat cgtgggggcc ctgatccagt ctgtgaagaa gctggctgat gtgatggtcc
 961 tcacagtctt ctgcctcagc gtctttgccc tcatcggcct gcagctcttc atgggcaacc
1021 taaggcacaa gtgcgtgcgc aacttcacag cgctcaacgg caccaacggc tccgtggagg
1081 ccgacggctt ggtctgggaa tccctggacc tttacctcag tgatccagaa aattacctgc
1141 tcaagaacgg cacctctgat gtgttactgt gtgggaacag ctctgacgct gggacatgtc
1201 cggagggcta ccggtgccta aaggcaggcg agaaccccga ccacggctac accagcttcg
1261 attcctttgc ctgggccttt cttgcactct tccgcctgat gacgcaggac tgctgggagc
1321 gcctctatca gcagaccctc aggtccgcag ggaagatcta catgatcttc ttcatgcttg
1381 tcatcttcct ggggtccttc tacctggtga acctgatcct ggccgtggtc gcaatggcct
1441 atgaggagca aaaccaagcc accatcgctg agaccgagga gaaggaaaag cgcttccagg
1501 aggccatgga aatgctcaag aaagaacacg aggccctcac catcaggggt gtggataccg
1561 tgtcccgtag ctccttggag atgtcccctt tggccccagt aaacagccat gagagaagaa
1621 gcaagaggag aaaacggatg tcttcaggaa ctgaggagtg tggggaggac aggctcccca
1681 agtctgactc agaagatggt cccagagcaa tgaatcatct cagcctcacc cgtggcctca
1741 gcaggacttc tatgaagcca cgttccagcc gcgggagcat tttcaccttt cgcaggcgag
1801 acctgggttc tgaagcagat tttgcagatg atgaaaacag cacagcgggg gagagcgaga
1861 gccaccacac atcactgctg gtgccctggc ccctgcgccg gaccagtgcc cagggacagc
1921 ccagtcccgg aacctcggct cctggccacg ccctccatgg caaaaagaac agcactgtgg
1981 actgcaatgg ggtggtctca ttactggggg caggcgaccc agaggccaca tccccaggaa
2041 gccacctcct ccgccctgtg atgctagagc acccgccaga cacgaccacg ccatcggagg
2101 agccaggcgg gccccagatg ctgacctccc aggctccgtg tgtagatggc ttcgaggagc
2161 caggagcacg gcagcgggcc ctcagcgcag tcagcgtcct caccagcgca ctggaagagt
2221 tagaggagtc tcgccacaag tgtccaccat gctggaaccg tctcgcccag cgctacctga
2281 tctgggagtg ctgcccgctg tggatgtcca tcaagcaggg agtgaagttg gtggtcatgg
2341 acccgtttac tgacctcacc atcactatgt gcatcgtact caacacactc ttcatggcgc
2401 tggagcacta caacatgaca agtgaattcg aggagatgct gcaggtcgga aacctggtct
2461 tcacagggat tttcacagca gagatgacct tcaagatcat tgccctcgac ccctactact
2521 acttccaaca gggctggaac atcttcgaca gcatcatcgt catccttagc ctcatggagc
2581 tgggcctgtc ccgcatgagc aacttgtcgg tgctgcgctc cttccgcctg ctgcgggtct
2641 tcaagctggc caaatcatgg cccaccctga acacactcat caagatcatc gggaactcag
2701 tgggggcact ggggaacctg acactggtgc tagccatcat cgtgttcatc tttgctgtgg
2761 tgggcatgca gctctttggc aagaactact cggagctgag ggacagcgac tcaggcctgc
2821 tgcctcgctg gcacatgatg gacttctttc atgccttcct catcatcttc cgcatcctct
2881 gtggagagtg gatcgagacc atgtgggact gcatggaggt gtcggggcag tcattatgcc
```

-continued

```
2941 tgctggtctt cttgcttgtt atggtcattg gcaaccttgt ggtcctgaat ctcttcctgg
3001 ccttgctgct cagctccttc agtgcagaca acctcacagc ccctgatgag gacagagaga
3061 tgaacaacct ccagctggcc ctggcccgca tccagagggg cctgcgcttt gtcaagcgga
3121 ccacctggga tttctgctgt ggtctcctgc ggcagcggcc tcagaagccc gcagcccttg
3181 ccgcccaggg ccagctgccc agctgcattg ccacccccta ctccccgcca cccccagaga
3241 cggagaaggt gcctcccacc cgcaaggaaa cacggtttga ggaaggcgag caaccaggcc
3301 agggcacccc cggggatcca gagcccgtgt gtgtgcccat cgctgtggcc gagtcagaca
3361 cagatgacca agaagaagat gaggagaaca gcctgggcac ggaggaggag tccagcaagc
3421 agcaggaatc ccagcctgtg tccggtggcc cagaggcccc tccggattcc aggacctgga
3481 gccaggtgtc agcgactgcc tcctctgagg ccgaggccag tgcatctcag gccgactggc
3541 ggcagcagtg gaaagcggaa ccccaggccc cagggtgcgg tgagacccca gaggacagtt
3601 gctccgaggg cagcacagca gacatgacca acaccgctga gctcctggag cagatccctg
3661 acctcggcca ggatgtcaag gacccagagg actgcttcac tgaaggctgt gtccggcgct
3721 gtccctgctg tgcggtggac accacacagg ccccagggaa ggtctggtgg cggttgcgca
3781 agacctgcta ccacatcgtg gagcacagct ggttcgagac attcatcatc ttcatgatcc
3841 tactcagcag tggagcgctg gccttcgagg acatctacct agaggagcgg aagaccatca
3901 aggttctgct tgagtatgcc gacaagatgt tcacatatgt cttcgtgctg gagatgctgc
3961 tcaagtgggt ggcctacggc ttcaagaagt acttcaccaa tgcctggtgc tggctcgact
4021 tcctcatcgt agacgtctct ctggtcagcc tggtggccaa caccctgggc tttgccgaga
4081 tgggccccat caagtcactg cggacgctgc gtgcactccg tcctctgaga gctctgtcac
4141 gatttgaggg catgagggtg gtggtcaatg ccctggtggg cgccatcccg tccatcatga
4201 acgtcctcct cgtctgcctc atcttctggc tcatcttcag catcatgggc gtgaacctct
4261 ttgcggggaa gtttgggagg tgcatcaacc agacagaggg agacttgcct ttgaactaca
4321 ccatcgtgaa caacaagagc cagtgtgagt ccttgaactt gaccggagaa ttgtactgga
4381 ccaaggtgaa agtcaacttt gacaacgtgg gggccgggta cctggccctt ctgcaggtgg
4441 caacatttaa aggctggatg gacattatgt atgcagctgt ggactccagg gggtatgaag
4501 agcagcctca gtgggaatac aacctctaca tgtacatcta ttttgtcatt ttcatcatct
4561 ttgggtcttt cttcaccctg aacctcttta ttggtgtcat cattgacaac ttcaaccaac
4621 agaagaaaaa gttagggggc caggacatct tcatgacaga ggagcagaag aagtactaca
4681 atgccatgaa gaagctgggc tccaagaagc cccagaagcc catcccacgg cccctgaaca
4741 agtaccaggg cttcatattc gacattgtga ccaagcaggc ctttgacgtc accatcatgt
4801 ttctgatctg cttgaatatg gtgaccatga tggtggagac agatgaccaa agtcctgaga
4861 aaatcaacat cttggccaag atcaacctgc tctttgtggc catcttcaca ggcgagtgta
4921 ttgtcaagct ggctgccctg cgccactact acttcaccaa cagctggaat atcttcgact
4981 tcgtggttgt catcctctcc atcgtgggag ccctcctagt gagtatgaag tgatatctca
5041 ctgaggtttt ggtttgcaaa agcaaatgac tgatgactaa cgatgcagga catctttcca
5101 tgtgcatgtt ggtcatttat atatcttcct tggagaaatc tctattcaga tccttagctc
5161 atttttaatt gggttatttc tcttcttctt gttgagttgt aagagttctt tacatattct
5221 ggatcacagt ctcttatcag atatatgatt taaaaatatt ttctcctagt ctgtgagttt
5281 tttcatttcc tagtggtgtc cattaaagca caaaagtttt acatgtt
```

E28B SCN5A Splice Variant Complete Amino Acid Sequence (the portion of the sequence that is different from wild-type is bolded and underlined):

(SEQ ID NO: 7)

1 manfllprgt ssfrrftres laaiekrmae kqargsttlq esreglpeee aprpqldlqa 61 skklpdlygn ppqeligepl edldpfystq ktfivlnkgk tifrfsatna lyvlspfhpi 121 rraavkilvh slfnmlimct iltncvfmaq hdpppwtkyv eytftaiytf eslvkilarg 181 fclhaftflr dpwnwldfsv iimayttefv dlgnvsalrt frvlralkti svisglktiv 241 galiqsvkkl advmvltvfc lsvfaliglq lfmgnlrhkc vrnftalngt ngsveadglv 301 wesldlylsd penyllkngt sdvllcgnss dagtcpegyr clkagenpdh gytsfdsfaw 361 aflalfrlmt qdcwerlyqq tlrsagkiym iffmlviflg sfylvnlila vvamayeeqn 421 qatiaeteek ekrfqeamem lkkehealti rgvdtvsrss lemsplapvn sherrskrrk 481 rmssgteecg edrlpksdse dgpramnhls ltrglsrtsm kprssrgsif tfrrrdlgse 541 adfaddenst ageseshhts llvpwplrrt saqgqpspgt sapghalhgk knstvdcngv 601 vsllgagdpe atspgshllr pvmlehppdt ttpseepggp qmltsqapcv dgfeepgarq 661 ralsavsvlt saleeleesr hkcppcwnrl aqryliwecc plwmsikqgv klvvmdpftd 721 ltitmcivln tlfmalehyn mtsefeemlq vgnlvftgif taemtfkiia ldpyyyfqqg 781 wnifdsiivi lslmelglsr msnlsvlrsf rllrvfklak swptlntlik iignsvgalg 841 nltlvlaiiv fifavvgmql fgknyselrd sdsgllprwh mmdffhafli ifrilcgewi 901 etmwdcmevs gqslcllvfl lvmvignlvv lnlflallls sfsadnltap dedremnnlq 961 lalariqrgl rfvkrttwdf ccgllrqrpq kpaalaaqgq lpsciatpys ppppetekvp 1021 ptrketrfee geqpgqgtpg dpepvcvpia vaesdtddqe edeenslgte eesskqqesq 1081 pvsggpeapp dsrtwsqvsa tasseaeasa sqadwrqqwk aepqapgcge tpedscsegs 1141 tadmtntael leqipdlgqd vkdpedcfte gcvrrcpcca vdttqapgkv wwrlrktcyh 1201 ivehswfetf iifmillssg alafediyle erktikvlle yadkmftyvf vlemllkwva 1261 ygfkkyftna wcwldflivd vslvslvant lgfaemgpik slrtlralrp lralsrfegm 1321 rvvvnalvga ipsimnvllv clifwlifsi mgvnlfagkf grcinqtegd lplnytivnn 1381 ksqceslnlt gelywtkvkv nfdnvgagyl allqvatfkg wmdimyaavd srgyeeqpqw 1441 eynlymyiyf vifiifgsff tlnlfigvii dnfnqqkkkl ggqdifmtee qkkyynamkk 1501 lgskkpqkpi prplnkyqgf ifdivtkqaf dvtimflicl nmvtmmvetd dqspekinil 1561 akinllfvai ftgecivkla alrhyyftns wnifdfvvvi lsivgallvs mk

E28C SCN5A Splice Variant Complete Nucleotide Sequence (the portion of the sequence that is different from wild-type is bolded and underlined):

(SEQ ID NO: 8)

1 agacggcggc ggcgcccgta ggatgcaggg atcgctcccc cggggccgct gagcctgcgc 61 ccagtgcccc gagccccgcg ccgagccgag tccgcgccaa gcagcagccg cccaccccgg 121 ggcccggccg ggggaccagc agcttcccca caggcaacgt gaggagagcc tgtgcccaga 181 agcaggatga gaagatggca aacttcctat tacctcgggg caccagcagc ttccgcaggt 241 tcacacggga gtccctggca gccatcgaga agcgcatggc agagaagcaa gcccgcggct 301 caaccacctt gcaggagagc cgagaggggc tgcccgagga ggaggctccc cggccccagc 361 tggacctgca ggcctccaaa aagctgccag atctctatgg caatccaccc caagagctca -continued

```
421 tcggagagcc cctggaggac ctggacccct tctatagcac ccaaaagact ttcatcgtac
481 tgaataaagg caagaccatc ttccggttca gtgccaccaa cgccttgtat gtcctcagtc
541 ccttccaccc catccggaga gcggctgtga agattctggt tcactcgctc ttcaacatgc
601 tcatcatgtg caccatcctc accaactgcg tgttcatggc ccagcacgac cctccaccct
661 ggaccaagta tgtcgagtac accttcaccg ccatttacac ctttgagtct ctggtcaaga
721 ttctggctcg aggcttctgc ctgcacgcgt tcactttcct tcgggaccca tggaactggc
781 tggactttag tgtgattatc atggcataca caactgaatt tgtggacctg ggcaatgtct
841 cagccttacg caccttccga gtcctccggg ccctgaaaac tatatcagtc atttcagggc
901 tgaagaccat cgtgggggcc ctgatccagt ctgtgaagaa gctggctgat gtgatggtcc
961 tcacagtctt ctgcctcagc gtctttgccc tcatcggcct gcagctcttc atgggcaacc
1021 taaggcacaa gtgcgtgcgc aacttcacag cgctcaacgg caccaacggc tccgtggagg
1081 ccgacggctt ggtctgggaa tccctggacc tttacctcag tgatccagaa aattacctgc
1141 tcaagaacgg cacctctgat gtgttactgt gtgggaacag ctctgacgct gggacatgtc
1201 cggagggcta ccggtgccta aaggcaggcg agaaccccga ccacggctac accagcttcg
1261 attcctttgc ctgggccttt cttgcactct tccgcctgat gacgcaggac tgctgggagc
1321 gcctctatca gcagaccctc aggtccgcag ggaagatcta catgatcttc ttcatgcttg
1381 tcatcttcct ggggtccttc tacctggtga acctgatcct ggccgtggtc gcaatggcct
1441 atgaggagca aaaccaagcc accatcgctg agaccgagga gaaggaaaag cgcttccagg
1501 aggccatgga aatgctcaag aaagaacacg aggccctcac catcaggggt gtggataccg
1561 tgtcccgtag ctccttggag atgtcccctt tggccccagt aaacagccat gagagaagaa
1621 gcaagaggag aaaacggatg tcttcaggaa ctgaggagtg tggggaggac aggctcccca
1681 agtctgactc agaagatggt cccagagcaa tgaatcatct cagcctcacc cgtggcctca
1741 gcaggacttc tatgaagcca cgttccagcc gcgggagcat tttcaccttt cgcaggcgag
1801 acctgggttc tgaagcagat tttgcagatg atgaaaacag cacagcgggg gagagcgaga
1861 gccaccacac atcactgctg gtgccctggc cctgcgccg gaccagtgcc cagggacagc
1921 ccagtcccgg aacctcggct cctggccacg ccctccatgg caaaaagaac agcactgtgg
1981 actgcaatgg ggtggtctca ttactggggg caggcgaccc agaggccaca tccccaggaa
2041 gccacctcct ccgccctgtg atgctagagc acccgccaga cacgaccacg ccatcggagg
2101 agccaggcgg gccccagatg ctgacctccc aggctccgtg tgtagatggc ttcgaggagc
2161 caggagcacg gcagcgggcc ctcagcgcag tcagcgtcct caccagcgca ctggaagagt
2221 tagaggagtc tcgccacaag tgtccaccat gctggaaccg tctcgcccag cgctacctga
2281 tctgggagtg ctgcccgctg tggatgtcca tcaagcaggg agtgaagttg gtggtcatgg
2341 acccgtttac tgacctcacc atcactatgt gcatcgtact caacacactc ttcatggcgc
2401 tggagcacta caacatgaca agtgaattcg aggagatgct gcaggtcgga aacctggtct
2461 tcacagggat tttcacagca gagatgacct tcaagatcat tgccctcgac ccctactact
2521 acttccaaca gggctggaac atcttcgaca gcatcatcgt catccttagc ctcatggagc
2581 tgggcctgtc ccgcatgagc aacttgtcgg tgctgcgctc cttccgcctg ctgcgggtct
2641 tcaagctggc caaatcatgg cccaccctga acacactcat caagatcatc gggaactcag
2701 tgggggcact ggggaacctg acactggtgc tagccatcat cgtgttcatc tttgctgtgg
2761 tgggcatgca gctctttggc aagaactact cggagctgag ggacagcgac tcaggcctgc
2821 tgcctcgctg gcacatgatg gacttctttc atgccttcct catcatcttc cgcatcctct
```

-continued 2881 gtggagagtg gatcgagacc atgtgggact gcatggaggt gtcggggcag tcattatgcc
2941 tgctggtctt cttgcttgtt atggtcattg gcaaccttgt ggtcctgaat ctcttcctgg
3001 ccttgctgct cagctccttc agtgcagaca acctcacagc ccctgatgag gacagagaga
3061 tgaacaacct ccagctggcc ctggcccgca tccagagggg cctgcgcttt gtcaagcgga
3121 ccacctggga tttctgctgt ggtctcctgc ggcagcggcc tcagaagccc gcagcccttg
3181 ccgcccaggg ccagctgccc agctgcattg ccacccccta ctccccgcca cccccagaga
3241 cggagaaggt gcctcccacc cgcaaggaaa cacggtttga ggaaggcgag caaccaggcc
3301 agggcacccc cggggatcca gagcccgtgt gtgtgcccat cgctgtggcc gagtcagaca
3361 cagatgacca agaagaagat gaggagaaca gcctgggcac ggaggaggag tccagcaagc
3421 agcaggaatc ccagcctgtg tccggtggcc cagaggcccc tccggattcc aggacctgga
3481 gccaggtgtc agcgactgcc tcctctgagg ccgaggccag tgcatctcag gccgactggc
3541 ggcagcagtg gaaagcggaa ccccaggccc cagggtgcgg tgagacccca gaggacagtt
3601 gctccgaggg cagcacagca gacatgacca acaccgctga gctcctggag cagatccctg
3661 acctcggcca ggatgtcaag gacccagagg actgcttcac tgaaggctgt gtccggcgct
3721 gtccctgctg tgcggtggac accacacagg ccccagggaa ggtctggtgg cggttgcgca
3781 agacctgcta ccacatcgtg gagcacagct ggttcgagac attcatcatc ttcatgatcc
3841 tactcagcag tggagcgctg gccttcgagg acatctacct agaggagcgg aagaccatca
3901 aggttctgct tgagtatgcc gacaagatgt tcacatatgt cttcgtgctg gagatgctgc
3961 tcaagtgggt ggcctacggc ttcaagaagt acttcaccaa tgcctggtgc tggctcgact
4021 tcctcatcgt agacgtctct ctggtcagcc tggtggccaa caccctgggc tttgccgaga
4081 tgggccccat caagtcactg cggacgctgc gtgcactccg tcctctgaga gctctgtcac
4141 gatttgaggg catgagggtg gtggtcaatg ccctggtggg cgccatcccg tccatcatga
4201 acgtcctcct cgtctgcctc atcttctggc tcatcttcag catcatgggc gtgaacctct
4261 ttgcggggaa gtttgggagg tgcatcaacc agacagaggg agacttgcct ttgaactaca
4321 ccatcgtgaa caacaagagc cagtgtgagt ccttgaactt gaccggagaa ttgtactgga
4381 ccaaggtgaa agtcaacttt gacaacgtgg gggccgggta cctggccctt ctgcaggtgg
4441 caacatttaa aggctggatg gacattatgt atgcagctgt ggactccagg gggtatgaag
4501 agcagcctca gtgggaatac aacctctaca tgtacatcta ttttgtcatt ttcatcatct
4561 ttgggtcttt cttcaccctg aacctcttta ttggtgtcat cattgacaac ttcaaccaac
4621 agaagaaaaa gttagggggc caggacatct tcatgacaga ggagcagaag aagtactaca
4681 atgccatgaa gaagctgggc tccaagaagc cccagaagcc catcccacgg cccctgaaca
4741 agtaccaggg cttcatattc gacattgtga ccaagcaggc ctttgacgtc accatcatgt
4801 ttctgatctg cttgaatatg gtgaccatga tggtggagac agatgaccaa agtcctgaga
4861 aaatcaacat cttggccaag atcaacctgc tctttgtggc catcttcaca ggcgagtgta
4921 ttgtcaagct ggctgccctg cgccactact acttcaccaa cagctggaat atcttcgact
4981 tcgtggttgt catcctctcc atcgtg<u>gaac tgcacaatga ccagcaggag gggagaagag</u>
5041 <u>agtaggaaaa aggagggaag gacagacatc aagtgccaga tgttgtctga actaatcgag</u>
5101 <u>cacttctcac caaacttcat gtataaataa aatacatatt tttaaaacaa accaataaat</u>
5161 <u>ggcttacatg</u>

E28C SCN5A Splice Variant Complete Amino Acid Sequence (the portion of the sequence that is different from wild-type is bolded and underlined):

(SEQ ID NO: 9)

```
   1 manfllprgt ssfrrftres laaiekrmae kqargsttlq esreglpeee aprpqldlqa
  61 skklpdlygn ppqeligepl edldpfystq ktfivlnkgk tifrfsatna lyvlspfhpi
 121 rraavkilvh slfnmlimct iltncvfmaq hdpppwtkyv eytftaiytf eslvkilarg
 181 fclhaftflr dpwnwldfsv iimayttefv dlgnvsalrt frvlralkti svisglktiv
 241 galiqsvkkl advmvltvfc lsvfaliglq lfmgnlrhkc vrnftalngt ngsveadglv
 301 wesldlylsd penyllkngt sdvllcgnss dagtcpegyr clkagenpdh gytsfdsfaw
 361 aflalfrlmt qdcwerlyqq tlrsagkiym iffmlviflg sfylvnlila vvamayeeqn
 421 qatiaeteek ekrfqeamem lkkehealti rgvdtvsrss lemsplapvn sherrskrrk
 481 rmssgteecg edrlpksdse dgpramnhls ltrglsrtsm kprssrgsif tfrrrdlgse
 541 adfaddenst ageseshhts llvpwplrrt saqgqpspgt sapghalhgk knstvdcngv
 601 vsllgagdpe atspgshllr pvmlehppdt ttpseepggp qmltsqapcv dgfeepgarq
 661 ralsavsvlt saleeleesr hkcppcwnrl aqryliwecc plwmsikqgv klvvmdpftd
 721 ltitmcivln tlfmalehyn mtsefeemlq vgnlvftgif taemtfkiia ldpyyyfqqg
 781 wnifdsiivi lslmelglsr msnlsvlrsf rllrvfklak swptlntlik iignsvgalg
 841 nltlvlaiiv fifavvgmql fgknyselrd sdsgllprwh mmdffhafli ifrilcgewi
 901 etmwdcmevs gqslcllvfl lvmvignlvv lnlflallls sfsadnltap dedremnnlq
 961 lalariqrgl rfvkrttwdf ccgllrqrpq kpaalaaqgq lpsciatpys ppppetekvp
1021 ptrketrfee geqpgqgtpg dpepvcvpia vaesdtddqe edeenslgte eesskqqesq
1081 pvsggpeapp dsrtwsqvsa tasseaeasa sqadwrqqwk aepqapgcge tpedscsegs
1141 tadmtntael leqipdlgqd vkdpedcfte gcvrrcpcca vdttqapgkv wwrlrktcyh
1201 ivehswfetf iifmillssg alafediyle erktikvlle yadkmftyvf vlemllkwva
1261 ygfkkyftna wcwldflivd vslvslvant lgfaemgpik slrtlralrp lralsrfegm
1321 rvvvnalvga ipsimnvllv clifwlifsi mgvnlfagkf grcinqtegd lplnytivnn
1381 ksqceslnlt gelywtkvkv nfdnvgagyl allqvatfkg wmdimyaavd srgyeeqpqw
1441 eynlymyiyf vifiifgsff tlnlfigvii dnfnqqkkkl ggqdifmtee qkkyynamkk
1501 lgskkpqkpi prplnkyqgf ifdivtkqaf dvtimflicl nmvtmmvetd dqspekinil
1561 akinllfvai ftgecivkla alrhyyftns wnifdfvvvi lsiv**elhndq qeqrre**
```

E28D SCN5A Splice Variant Complete Nucleotide Sequence (the portion of the sequence that is different from wild-type is bolded and underlined):

(SEQ ID NO: 10)

```
   1 agacggcggc ggcgcccgta ggatgcaggg atcgctcccc cggggccgct gagcctgcgc
  61 ccagtgcccc gagccccgcg ccgagccgag tccgcgccaa gcagcagccg cccaccccgg
 121 ggcccggccg ggggaccagc agcttcccca caggcaacgt gaggagagcc tgtgcccaga
 181 agcaggatga aagatggcaa acttcctat tacctcgggg caccagcagc ttccgcaggt
 241 tcacacggga gtccctggca gccatcgaga gcgcatggc agagaagcaa gcccgcggct
 301 caaccacctt gcaggagagc cgagaggggc tgcccgagga ggaggctccc cggccccagc
 361 tggacctgca ggcctccaaa aagctgccag atctctatgg caatccaccc caagagctca
```

-continued

```
421 tcggagagcc cctggaggac ctggacccct tctatagcac ccaaaagact ttcatcgtac
481 tgaataaagg caagaccatc ttccggttca gtgccaccaa cgccttgtat gtcctcagtc
541 ccttccaccc catccggaga gcggctgtga agattctggt tcactcgctc ttcaacatgc
601 tcatcatgtg caccatcctc accaactgcg tgttcatggc ccagcacgac cctccaccct
661 ggaccaagta tgtcgagtac accttcaccg ccatttacac ctttgagtct ctggtcaaga
721 ttctggctcg aggcttctgc ctgcacgcgt tcactttcct tcgggaccca tggaactggc
781 tggactttag tgtgattatc atggcataca caactgaatt tgtggacctg ggcaatgtct
841 cagccttacg caccttccga gtcctccggg ccctgaaaac tatatcagtc atttcagggc
901 tgaagaccat cgtgggggcc ctgatccagt ctgtgaagaa gctggctgat gtgatggtcc
961 tcacagtctt ctgcctcagc gtctttgccc tcatcggcct gcagctcttc atgggcaacc
1021 taaggcacaa gtgcgtgcgc aacttcacag cgctcaacgg caccaacggc tccgtggagg
1081 ccgacggctt ggtctgggaa tccctggacc tttacctcag tgatccagaa aattacctgc
1141 tcaagaacgg cacctctgat gtgttactgt gtgggaacag ctctgacgct gggacatgtc
1201 cggagggcta ccggtgccta aaggcaggcg agaaccccga ccacggctac accagcttcg
1261 attcctttgc ctgggccttt cttgcactct tccgcctgat gacgcaggac tgctgggagc
1321 gcctctatca gcagaccctc aggtccgcag ggaagatcta catgatcttc ttcatgcttg
1381 tcatcttcct ggggtccttc tacctggtga acctgatcct ggccgtggtc gcaatggcct
1441 atgaggagca aaaccaagcc accatcgctg agaccgagga gaaggaaaag cgcttccagg
1501 aggccatgga aatgctcaag aaagaacacg aggccctcac catcaggggt gtggataccg
1561 tgtcccgtag ctccttggag atgtcccctt tggccccagt aaacagccat gagagaagaa
1621 gcaagaggag aaaacggatg tcttcaggaa ctgaggagtg tggggaggac aggctcccca
1681 agtctgactc agaagatggt cccagagcaa tgaatcatct cagcctcacc cgtggcctca
1741 gcaggacttc tatgaagcca cgttccagcc gcgggagcat tttcaccttt cgcaggcgag
1801 acctgggttc tgaagcagat tttgcagatg atgaaaacag cacagcgggg gagagcgaga
1861 gccaccacac atcactgctg gtgccctggc cctgcgccg gaccagtgcc cagggacagc
1921 ccagtcccgg aacctcggct cctggccacg ccctccatgg caaaaagaac agcactgtgg
1981 actgcaatgg ggtggtctca ttactggggg caggcgaccc agaggccaca tccccaggaa
2041 gccacctcct ccgccctgtg atgctagagc acccgccaga cacgaccacg ccatcggagg
2101 agccaggcgg gccccagatg ctgacctccc aggctccgtg tgtagatggc ttcgaggagc
2161 caggagcacg gcagcgggcc ctcagcgcag tcagcgtcct caccagcgca ctggaagagt
2221 tagaggagtc tcgccacaag tgtccaccat gctggaaccg tctcgcccag cgctacctga
2281 tctgggagtg ctgcccgctg tggatgtcca tcaagcaggg agtgaagttg gtggtcatgg
2341 acccgtttac tgacctcacc atcactatgt gcatcgtact caacacactc ttcatggcgc
2401 tggagcacta caacatgaca agtgaattcg aggagatgct gcaggtcgga aacctggtct
2461 tcacagggat tttcacagca gagatgacct tcaagatcat tgccctcgac ccctactact
2521 acttccaaca gggctggaac atcttcgaca gcatcatcgt catccttagc ctcatggagc
2581 tgggcctgtc ccgcatgagc aacttgtcgg tgctgcgctc cttccgcctg ctgcgggtct
2641 tcaagctggc caaatcatgg cccaccctga acacactcat caagatcatc gggaactcag
2701 tgggggcact ggggaacctg acactggtgc tagccatcat cgtgttcatc tttgctgtgg
2761 tgggcatgca gctctttggc aagaactact cggagctgag ggacagcgac tcaggcctgc
2821 tgcctcgctg gcacatgatg gacttctttc atgccttcct catcatcttc cgcatcctct
```

-continued 2881 gtggagagtg gatcgagacc atgtgggact gcatggaggt gtcggggcag tcattatgcc 2941 tgctggtctt cttgcttgtt atggtcattg gcaaccttgt ggtcctgaat ctcttcctgg 3001 ccttgctgct cagctccttc agtgcagaca acctcacagc ccctgatgag gacagagaga 3061 tgaacaacct ccagctggcc ctggcccgca tccagagggg cctgcgcttt gtcaagcgga 3121 ccacctggga tttctgctgt ggtctcctgc ggcagcggcc tcagaagccc gcagcccttg 3181 ccgcccaggg ccagctgccc agctgcattg ccaccccccta ctccccgcca cccccagaga 3241 cggagaaggt gcctcccacc cgcaaggaaa cacggtttga ggaaggcgag caaccaggcc 3301 agggcacccc cggggatcca gagcccgtgt gtgtgcccat cgctgtggcc gagtcagaca 3361 cagatgacca agaagaagat gaggagaaca gcctgggcac ggaggaggag tccagcaagc 3421 agcaggaatc ccagcctgtg tccggtggcc cagaggcccc tccggattcc aggacctgga 3481 gccaggtgtc agcgactgcc tcctctgagg ccgaggccag tgcatctcag gccgactggc 3541 ggcagcagtg gaaagcggaa ccccaggccc cagggtgcgg tgagacccca gaggacagtt 3601 gctccgaggg cagcacagca gacatgacca acaccgctga gctcctggag cagatccctg 3661 acctcggcca ggatgtcaag gacccagagg actgcttcac tgaaggctgt gtccggcgct 3721 gtccctgctg tgcggtggac accacacagg ccccagggaa ggtctggtgg cggttgcgca 3781 agacctgcta ccacatcgtg gagcacagct ggttcgagac attcatcatc ttcatgatcc 3841 tactcagcag tggagcgctg gccttcgagg acatctacct agaggagcgg aagaccatca 3901 aggttctgct tgagtatgcc gacaagatgt tcacatatgt cttcgtgctg gagatgctgc 3961 tcaagtgggt ggcctacggc ttcaagaagt acttcaccaa tgcctggtgc tggctcgact 4021 tcctcatcgt agacgtctct ctggtcagcc tggtggccaa caccctgggc tttgccgaga 4081 tgggccccat caagtcactg cggacgctgc gtgcactccg tcctctgaga gctctgtcac 4141 gatttgaggg catgagggtg gtggtcaatg ccctggtggg cgccatcccg tccatcatga 4201 acgtcctcct cgtctgcctc atcttctggc tcatcttcag catcatgggc gtgaacctct 4261 ttgcggggaa gtttgggagg tgcatcaacc agacagaggg agacttgcct ttgaactaca 4321 ccatcgtgaa caacaagagc cagtgtgagt ccttgaactt gaccggagaa ttgtactgga 4381 ccaaggtgaa agtcaacttt gacaacgtgg gggccgggta cctggccctt ctgcaggtgg 4441 caacatttaa aggctggatg gacattatgt atgcagctgt ggactccagg gggtatgaag 4501 agcagcctca gtgggaatac aacctctaca tgtacatcta ttttgtcatt ttcatcatct 4561 ttgggtcttt cttcaccctg aacctcttta ttggtgtcat cattgacaac ttcaaccaac 4621 agaagaaaaa gttagggggc caggacatct tcatgacaga ggagcagaag aagtactaca 4681 atgccatgaa gaagctgggc tccaagaagc cccagaagcc catcccacgg cccctgaaca 4741 agtaccaggg cttcatattc gacattgtga ccaagcaggc ctttgacgtc accatcatgt 4801 ttctgatctg cttgaatatg gtgaccatga tggtggagac agatgaccaa agtcctgaga 4861 aaatcaacat cttggccaag atcaacctgc tctttgtggc catcttcaca ggcgagtgta 4921 ttgtcaagct ggctgccctg cgccactact acttcaccaa cagctggaat atcttcgact 4981 tcgtggttgt catcctctcc atcgtgggca ctgtgctctc ggacatcatc cagaagtact

5041 tcttctcccc gacgctcttc cgagtcatcc gcctggcccg aataggccgc atcctcagac

5101 tgatccgagg ggccaagggg

E28D SCN5A Splice Variant Complete Amino Acid Sequence (the portion of the sequence that is different from wild-type is bolded and underlined):

(SEQ ID NO: 11)

1 manfllprgt ssfrrftres laaiekrmae kqargsttlq esreglpeee aprpqldlqa 61 skklpdlygn ppqeligepl edldpfystq ktfivlnkgk tifrfsatna lyvlspfhpi 121 rraavkilvh slfnmlimct iltncvfmaq hdpppwtkyv eytftaiytf eslvkilarg 181 fclhaftflr dpwnwldfsv iimayttefv dlgnvsalrt frvlralkti svisglktiv 241 galiqsvkkl advmvltvfc lsvfaliglq lfmgnlrhkc vrnftalngt ngsveadglv 301 wesldlylsd penyllkngt sdvllcgnss dagtcpegyr clkagenpdh gytsfdsfaw 361 aflalfrlmt qdcwerlyqq tlrsagkiym iffmlviflg sfylvnlila vvamayeeqn 421 qatiaeteek ekrfqeamem lkkehealti rgvdtvsrss lemsplapvn sherrskrrk 481 rmssgteecg edrlpksdse dgpramnhls ltrglsrtsm kprssrgsif tfrrrdlgse 541 adfaddenst ageseshhts llvpwplrrt saqgqpspgt sapghalhgk knstvdcngv 601 vsllgagdpe atspgshllr pvmlehppdt ttpseepggp qmltsqapcv dgfeepgarq 661 ralsavsvlt saleeleesr hkcppcwnrl aqryliwecc plwmsikqgv klvvmdpftd 721 ltitmcivln tlfmalehyn mtsefeemlq vgnlvftgif taemtfkiia ldpyyyfqqg 781 wnifdsiivi lslmelglsr msnlsvlrsf rllrvfklak swptlntlik iignsvgalg 841 nltlvlaiiv fifavvgmql fgknyselrd sdsgllprwh mmdffhafli ifrilcgewi 901 etmwdcmevs gqslcllvfl lvmvignlvv lnlflallls sfsadnltap dedremnnlq 961 lalariqrgl rfvkrttwdf ccgllrqrpq kpaalaaqgq lpsciatpys ppppetekvp 1021 ptrketrfee geqpgqgtpg dpepvcvpia vaesdtddqe edeenslgte eesskqqesq 1081 pvsggpeapp dsrtwsqvsa tasseaeasa sqadwrqqwk aepqapgcge tpedscsegs 1141 tadmtntael leqipdlgqd vkdpedcfte gcvrrcpcca vdttqapgkv wwrlrktcyh 1201 ivehswfetf iifmillssg alafediyle erktikvlle yadkmftyvf vlemllkwva 1261 ygfkkyftna wcwldflivd vslvslvant lgfaemgpik slrtlralrp lralsrfegm 1321 rvvvnalvga ipsimnvllv clifwlifsi mgvnlfagkf grcinqtegd lplnytivnn 1381 ksqceslnlt gelywtkvkv nfdnvgagyl allqvatfkg wmdimyaavd srgyeeqpqw 1441 eynlymyiyf vifiifgsff tlnlfigvii dnfnqqkkkl ggqdifmtee qkkyynamkk 1501 lgskkpqkpi prplnkyqgf ifdivtkqaf dvtimflicl nmvtmmvetd dqspekinil 1561 akinllfvai ftgecivkla alrhyyftns wnifdfvvvi lsivgtvlsd iiqkyffspt

1621 lfrvirlari grilrlirga kg

A full-length SCN5A amino acid sequence:

(SEQ ID NO: 12)

1 manfllprgt ssfrrftres laaiekrmae kqargsttlq esreglpeee aprpqldlqa 61 skklpdlygn ppqeligepl edldpfystq ktfivlnkgk tifrfsatna lyvlspfhpi 121 rraavkilvh slfnmlimct iltncvfmaq hdpppwtkyv eytftaiytf eslvkilarg 181 fclhaftflr dpwnwldfsv iimayttefv dlgnvsalrt frvlralkti svisglktiv 241 galiqsvkkl advmvltvfc lsvfaliglq lfmgnlrhkc vrnftalngt ngsveadglv 301 wesldlylsd penyllkngt sdvllcgnss dagtcpegyr clkagenpdh gytsfdsfaw 361 aflalfrlmt qdcwerlyqq tlrsagkiym iffmlviflg sfylvnlila vvamayeeqn -continued

```
 421 qatiaeteek ekrfqeamem lkkehealti rgvdtvsrss lemsplapvn sherrskrrk
 481 rmssgteecg edrlpksdse dgpramnhls ltrglsrtsm kprssrgsif tfrrrdlgse
 541 adfaddenst ageseshhts llvpwplrrt saqgqpspgt sapghalhgk knstvdcngv
 601 vsllgagdpe atspgshllr pvmlehppdt ttpseepggp qmltsqapcv dgfeepgarq
 661 ralsavsvlt saleeleesr hkcppcwnrl aqryliwecc plwmsikqgv klvvmdpftd
 721 ltitmcivln tlfmalehyn mtsefeemlq vgnlvftgif taemtfkiia ldpyyyfqqg
 781 wnifdsiivi lslmelglsr msnlsvlrsf rllrvfklak swptlntlik iignsvgalg
 841 nltlvlaiiv fifavvgmql fgknyselrd sdsgllprwh mmdffhafli ifrilcgewi
 901 etmwdcmevs gqslcllvfl lvmvignlvv lnlflallls sfsadnltap dedremnnlq
 961 lalariqrgl rfvkrttwdf ccgllrqrpq kpaalaaqgq lpsciatpys ppppetekvp
1021 ptrketrfee geqpgqgtpg dpepvcvpia vaesdtddqe edeenslgte eesskqqesq
1081 pvsggpeapp dsrtwsqvsa tasseaeasa sqadwrqqwk aepqapgcge tpedscsegs
1141 tadmtntael leqipdlgqd vkdpedcfte gcvrrcpcca vdttqapgkv wwrlrktcyh
1201 ivehswfetf iifmillssg alafediyle erktikvlle yadkmftyvf vlemllkwva
1261 ygfkkyftna wcwldflivd vslvslvant lgfaemgpik slrtlralrp lralsrfegm
1321 rvvvnalvga ipsimnvllv clifwlifsi mgvnlfagkf grcinqtegd lplnytivnn
1381 ksqceslnlt gelywtkvkv nfdnvgagyl allqvatfkg wmdimyaavd srgyeeqpqw
1441 eynlymyiyf vifiifgsff tlnlfigvii dnfnqqkkkl ggqdifmtee qkkyynamkk
1501 lgskkpqkpi prplnkyqgf ifdivtkqaf dvtimflicl nmvtmmvetd dqspekinil
1561 akinllfvai ftgecivkla alrhyyftns wnifdfvvvi lsivgtvlsd iiqkyffspt
1621 lfrvirlari grilrlirga kgirtllfal mmslpalfni glllflvmfi ysifgmanfa
1681 yvkweagidd mfnfqtfans mlclfqitts agwdgllspi lntgppycdp tlpnsngsrg
1741 dcgspavgil ffttyiiisf livvnmyiai ilenfsvate esteplsedd fdmfyeiwek
1801 fdpeatqfie ysvlsdfada lseplriakp nqislinmdl pmvsgdrihc mdilfaftkr
1861 vlgesgemda lkiqmeekfm aanpskisye pitttlrrkh eevsamviqr afrrhllqrs
1921 lkhasflfrq qagsglseed aperegliay vmsenfsrpl gppssssiss tsfppsydsv
1981 tratsdniqv rgsdyshsed ladfppspdr dresiv
```

GenBank Accession NP_932173.1 (GI: 37622907), incorporated herein by reference.

Exemplary regions or fragments of SCN5A include residues 159-412 (ion transport region), 159-178 (transmembrane region), 842-862 (transmembrane region), and 1201-1224 (sodium ion transport-associated region).

A full-length SCN5A nucleotide sequence (the start and stop codons of the coding sequence are bold and underlined):

(SEQ ID NO: 5)

```
  1 agacggcggc ggcgcccgta ggatgcaggg atcgctcccc cggggccgct gagcctgcgc
 61 ccagtgcccc gagccccgcg ccgagccgag tccgcgccaa gcagcagccg cccacccc gg
121 ggcccggccg ggggaccagc agcttcccca caggcaacgt gaggagagcc tgtgcccaga
181 agcaggatga gaagatggca aacttcctat tacctcgggg caccagcagc ttccgcaggt
241 tcacacggga gtccctggca gccatcgaga agcgcatggc agagaagcaa gcccgcggct
301 caaccacctt gcaggagagc cgagaggggc tgcccgagga ggaggctccc cggccccagc
```

-continued 361 tggacctgca ggcctccaaa aagctgccag atctctatgg caatccaccc caagagctca
421 tcggagagcc cctggaggac ctggacccct tctatagcac ccaaaagact ttcatcgtac
481 tgaataaagg caagaccatc ttccggttca gtgccaccaa cgccttgtat gtcctcagtc
541 ccttccaccc catccggaga gcggctgtga agattctggt tcactcgctc ttcaacatgc
601 tcatcatgtg caccatcctc accaactgcg tgttcatggc ccagcacgac cctccaccct
661 ggaccaagta tgtcgagtac accttcaccg ccatttacac ctttgagtct ctggtcaaga
721 ttctggctcg aggcttctgc ctgcacgcgt tcactttcct tcgggaccca tggaactggc
781 tggactttag tgtgattatc atggcataca caactgaatt tgtggacctg ggcaatgtct
841 cagccttacg caccttccga gtcctccggg ccctgaaaac tatatcagtc atttcagggc
901 tgaagaccat cgtgggggcc ctgatccagt ctgtgaagaa gctggctgat gtgatggtcc
961 tcacagtctt ctgcctcagc gtctttgccc tcatcggcct gcagctcttc atgggcaacc
1021 taaggcacaa gtgcgtgcgc aacttcacag cgctcaacgg caccaacggc tccgtggagg
1081 ccgacggctt ggtctgggaa tccctggacc tttacctcag tgatccagaa aattacctgc
1141 tcaagaacgg cacctctgat gtgttactgt gtgggaacag ctctgacgct gggacatgtc
1201 cggagggcta ccggtgccta aaggcaggcg agaaccccga ccacggctac accagcttcg
1261 attcctttgc ctgggccttt cttgcactct tccgcctgat gacgcaggac tgctgggagc
1321 gcctctatca gcagaccctc aggtccgcag ggaagatcta catgatcttc ttcatgcttg
1381 tcatcttcct ggggtccttc tacctggtga acctgatcct ggccgtggtc gcaatggcct
1441 atgaggagca aaaccaagcc accatcgctg agaccgagga gaaggaaaag cgcttccagg
1501 aggccatgga aatgctcaag aaagaacacg aggccctcac catcaggggt gtggataccg
1561 tgtcccgtag ctccttggag atgtcccctt tggccccagt aaacagccat gagagaagaa
1621 gcaagaggag aaaacggatg tcttcaggaa ctgaggagtg tggggaggac aggctcccca
1681 agtctgactc agaagatggt cccagagcaa tgaatcatct cagcctcacc cgtggcctca
1741 gcaggacttc tatgaagcca cgttccagcc gcgggagcat tttcaccttt cgcaggcgag
1801 acctgggttc tgaagcagat tttgcagatg atgaaaacag cacagcgggg gagagcgaga
1861 gccaccacac atcactgctg gtgccctggc ccctgcgccg gaccagtgcc cagggacagc
1921 ccagtcccgg aacctcggct cctggccacg ccctccatgg caaaaagaac agcactgtgg
1981 actgcaatgg ggtggtctca ttactggggg caggcgaccc agaggccaca tccccaggaa
2041 gccacctcct ccgccctgtg atgctagagc acccgccaga cacgaccacg ccatcggagg
2101 agccaggcgg gccccagatg ctgacctccc aggctccgtg tgtagatggc ttcgaggagc
2161 caggagcacg gcagcgggcc ctcagcgcag tcagcgtcct caccagcgca ctggaagagt
2221 tagaggagtc tcgccacaag tgtccaccat gctggaaccg tctcgcccag cgctacctga
2281 tctgggagtg ctgcccgctg tggatgtcca tcaagcaggg agtgaagttg gtggtcatgg
2341 acccgtttac tgacctcacc atcactatgt gcatcgtact caacacactc ttcatggcgc
2401 tggagcacta caacatgaca agtgaattcg aggagatgct gcaggtcgga aacctggtct
2461 tcacagggat tttcacagca gagatgacct tcaagatcat tgccctcgac ccctactact
2521 acttccaaca gggctggaac atcttcgaca gcatcatcgt catccttagc ctcatggagc
2581 tgggcctgtc ccgcatgagc aacttgtcgg tgctgcgctc cttccgcctg ctgcgggtct
2641 tcaagctggc caaatcatgg cccaccctga acacactcat caagatcatc gggaactcag
2701 tgggggcact ggggaacctg acactggtgc tagccatcat cgtgttcatc tttgctgtgg
2761 tgggcatgca gctctttggc aagaactact cggagctgag ggacagcgac tcaggcctgc -continued

```
2821 tgcctcgctg gcacatgatg gacttctttc atgccttcct catcatcttc cgcatcctct
2881 gtggagagtg gatcgagacc atgtgggact gcatggaggt gtcggggcag tcattatgcc
2941 tgctggtctt cttgcttgtt atggtcattg gcaaccttgt ggtcctgaat ctcttcctgg
3001 ccttgctgct cagctccttc agtgcagaca acctcacagc ccctgatgag gacagagaga
3061 tgaacaacct ccagctggcc ctggcccgca tccagagggg cctgcgcttt gtcaagcgga
3121 ccacctggga tttctgctgt ggtctcctgc ggcagcggcc tcagaagccc gcagcccttg
3181 ccgcccaggg ccagctgccc agctgcattg ccacccccta ctccccgcca cccccagaga
3241 cggagaaggt gcctcccacc cgcaaggaaa cacggtttga ggaaggcgag caaccaggcc
3301 agggcacccc cggggatcca gagcccgtgt gtgtgcccat cgctgtggcc gagtcagaca
3361 cagatgacca agaagaagat gaggagaaca gcctgggcac ggaggaggag tccagcaagc
3421 agcaggaatc ccagcctgtg tccggtggcc cagaggcccc tccggattcc aggacctgga
3481 gccaggtgtc agcgactgcc tcctctgagg ccgaggccag tgcatctcag gccgactggc
3541 ggcagcagtg gaaagcggaa ccccaggccc cagggtgcgg tgagacccca gaggacagtt
3601 gctccgaggg cagcacagca gacatgacca acaccgctga gctcctggag cagatccctg
3661 acctcggcca ggatgtcaag gacccagagg actgcttcac tgaaggctgt gtccggcgct
3721 gtccctgctg tgcggtggac accacacagg ccccagggaa ggtctggtgg cggttgcgca
3781 agacctgcta ccacatcgtg gagcacagct ggttcgagac attcatcatc ttcatgatcc
3841 tactcagcag tggagcgctg gccttcgagg acatctacct agaggagcgg aagaccatca
3901 aggttctgct tgagtatgcc gacaagatgt tcacatatgt cttcgtgctg gagatgctgc
3961 tcaagtgggt ggcctacggc ttcaagaagt acttcaccaa tgcctggtgc tggctcgact
4021 tcctcatcgt agacgtctct ctggtcagcc tggtggccaa caccctgggc tttgccgaga
4081 tgggccccat caagtcactg cggacgctgc gtgcactccg tcctctgaga gctctgtcac
4141 gatttgaggg catgagggtg gtggtcaatg ccctggtggg cgccatcccg tccatcatga
4201 acgtcctcct cgtctgcctc atcttctggc tcatcttcag catcatgggc gtgaacctct
4261 ttgcggggaa gtttgggagg tgcatcaacc agacagaggg agacttgcct ttgaactaca
4321 ccatcgtgaa caacaagagc cagtgtgagt ccttgaactt gaccggagaa ttgtactgga
4381 ccaaggtgaa agtcaacttt gacaacgtgg gggccgggta cctggccctt ctgcaggtgg
4441 caacatttaa aggctggatg gacattatgt atgcagctgt ggactccagg gggtatgaag
4501 agcagcctca gtgggaatac aacctctaca tgtacatcta ttttgtcatt ttcatcatct
4561 ttgggtcttt cttcaccctg aacctcttta ttggtgtcat cattgacaac ttcaaccaac
4621 agaagaaaaa gttagggggc caggacatct tcatgacaga ggagcagaag aagtactaca
4681 atgccatgaa gaagctgggc tccaagaagc cccagaagcc catcccacgg cccctgaaca
4741 agtaccaggg cttcatattc gacattgtga ccaagcaggc ctttgacgtc accatcatgt
4801 ttctgatctg cttgaatatg gtgaccatga tggtggagac agatgaccaa agtcctgaga
4861 aaatcaacat cttggccaag atcaacctgc tctttgtggc catcttcaca ggcgagtgta
4921 ttgtcaagct ggctgccctg cgccactact acttcaccaa cagctggaat atcttcgact
4981 tcgtggttgt catcctctcc atcgtgggca ctgtgctctc ggacatcatc cagaagtact
5041 tcttctcccc gacgctcttc cgagtcatcc gcctggcccg aataggccgc atcctcagac
5101 tgatccgagg ggccaagggg atccgcacgc tgctctttgc cctcatgatg tccctgcctg
5161 ccctcttcaa catcgggctg ctgctcttcc tcgtcatgtt catctactcc atctttggca
```

-continued 5221 tggccaactt cgcttatgtc aagtgggagg ctggcatcga cgacatgttc aacttccaga
5281 ccttcgccaa cagcatgctg tgcctcttcc agatcaccac gtcggccggc tgggatggcc
5341 tcctcagccc catcctcaac actgggccgc cctactgcga ccccactctg cccaacagca
5401 atggctctcg gggggactgc gggagcccag ccgtgggcat cctcttcttc accacctaca
5461 tcatcatctc cttcctcatc gtggtcaaca tgtacattgc catcatcctg gagaacttca
5521 gcgtggccac ggaggagagc accgagcccc tgagtgagga cgacttcgat atgttctatg
5581 agatctggga gaaatttgac ccagaggcca ctcagtttat tgagtattcg gtcctgtctg
5641 actttgccga tgccctgtct gagccactcc gtatcgccaa gcccaaccag ataagcctca
5701 tcaacatgga cctgcccatg gtgagtgggg accgcatcca ttgcatggac attctctttg
5761 ccttcaccaa aagggtcctg ggggagtctg gggagatgga cgccctgaag atccagatgg
5821 aggagaagtt catggcagcc aacccatcca agatctccta cgagcccatc accaccacac
5881 tccggcgcaa gcacgaagag gtgtcggcca tggttatcca gagagccttc cgcaggcacc
5941 tgctgcaacg ctctttgaag catgcctcct tcctcttccg tcagcaggcg ggcagcggcc
6001 tctccgaaga ggatgcccct gagcgagagg gcctcatcgc ctacgtgatg agtgagaact
6061 tctcccgacc ccttggccca ccctccagct cctccatctc ctccacttcc ttcccaccct
6121 cctatgacag tgtcactaga gccaccagcg ataacctcca ggtgcggggg tctgactaca
6181 gccacagtga agatctcgcc gacttccccc cttctccgga cagggaccgt gagtccatcg
6241 tgtgagcctc ggcctggctg gccaggacac actgaaaagc agcctttttc accatggcaa
6301 acctaaatgc agtcagtcac aaaccagcct ggggccttcc tggctttggg agtaagaaat
6361 gggcctcagc cccgcggatc aaccaggcag agttctgtgg cgccgcgtgg acagccggag
6421 cagttggcct gtgcttggag gcctcagata gacctgtgac ctggtctggt caggcaatgc
6481 cctgcggctc tggaaagcaa cttcatccca gctgctgagg cgaaatataa aactgagact
6541 gtatatgttg tgaatgggct ttcataaatt tattatattt gatatttttt tacttgagca
6601 aagaactaag gatttttcca tggacatggg cagcaattca cgctgtctct tcttaaccct
6661 gaacaagagt gtctatggag cagccggaag tctgttctca aagcagaagt ggaatccagt
6721 gtggctccca caggtcttca ctgcccaggg gtcgaatggg gtcccccctcc cacttgacct
6781 gagatgctgg gagggctgaa cccccactca cacaagcaca cacacacagt cctcacacac
6841 ggaggccaga cacaggccgt gggacccagg ctcccagcct aagggagaca ggcctttccc
6901 tgccggcccc ccaaggatgg ggttcttgtc cacggggctc actctggccc cctattgtct
6961 ccaaggtccc attttccccc tgtgttttca cgcaggtcat attgtcagtc ctacaaaaat
7021 aaaaggcttc cagaggagag tggcctgggt cccagggctg gccctaggca ctgatagttg
7081 ccttttcttc ccctcctgta agagtattaa caaaaccaaa ggacacaagg gtgcaagccc
7141 cattcacggc ctggcatgca gcttgtcctt gctcctggaa cctggcaggc cctgcccagc
7201 cagccatcgg aagagagggc tgagccatgg gggtttgggg ctaagaagtt caccagccct
7261 gagccatggc ggcccctcag cctgcctgaa gagaggaaac tggcgatctc ccagggctct
7321 ctggaccata cgcggaggag ttttctgtgt ggtctccagc tcctctccag acacagagac
7381 atgggagtgg ggagcggagc ttggccctgc gccctgtgca gggaaaggga tggtcaggcc
7441 cagttctcgt gcccttagag gggaatgaac catggcacct ttgagagagg gggcactgtg
7501 gtcaggccca gcctctctgg ctcagcccgg gatcctgatg gcacccacac agaggacctc
7561 tttggggcaa gatccaggtg gtcccatagg tcttgtgaaa aggctttttc agggaaaaat
7621 attttactag tccaatcacc cccaggacct cttcagctgc tgacaatcct atttagcata -continued

```
7681 tgcaaatctt ttaacataga gaactgtcac cctgaggtaa cagggtcaac tggcgaagcc
7741 tgagcaggca ggggcttggc tgccccattc cagctctccc atggagcccc tccaccgggc
7801 gcatgcctcc caggccacct cagtctcacc tgccggctct gggctggctg ctcctaacct
7861 acctcgccga gctgtcggag ggctggacat ttgtggcagt gctgaagggg gcattgccgg
7921 cgagtaaagt attatgtttc ttcttgtcac cccagttccc ttggtggcaa ccccagaccc
7981 aacccatgcc cctgacagat ctagttctct tctcctgtgt tccctttgag tccagtgtgg
8041 gacacggttt aactgtccca gcgacatttc tccaagtgga aatcctattt ttgtagatct
8101 ccatgctttg ctctcaaggc ttggagaggt atgtgcccct cctgggtgct caccgcctgc
8161 tacacaggca ggaatgcggt tgggaggcag gtcgggctgc cagcccagct ggccggaagg
8221 agactgtggt ttttgtgtgt gtggacagcc cgggagcttt gagacaggtg cctggggctg
8281 gctgcagacg gtgtggttgg gggtgggagg tgagctagac ccaaccctta gcttttagcc
8341 tggctgtcac ctttttaatt tccagaactg cacaatgacc agcaggaggg aaggacagac
8401 atcaagtgcc agatgttgtc tgaactaatc gagcacttct caccaaactt catgtataaa
8461 taaaatacat atttttaaaa caaaccaata aatggcttac atga
```

GenBank Accession NM_198056.2 (GI: 124518659), incorporated herein by reference.

Exemplary regions or fragments of SCN5A include residues 95-1022 (transmembrane region), 1563-1565 (phosphorylation site), 1731-1733 (methylation site), and 5172-5240 (transmembrane region).

Pulmonary Hypertension

There are multiple subtypes of pulmonary hypertension (PH). Classifications for PH include the World Health Organization (WHO) Groups (the "WHO Groups") adopted during the 5$^{th}$ World Symposium on Pulmonary Hypertension which was held in 2015 in Nice, France. The adopted classification system is also known as "Nice Classification." The Nice WHO Group classifications are described in Simonneau et al., (2013) "Updated Clinical Classification of Pulmonary Hypertension" Journal of the American College of Cardiology Vol 62 No 25 D34-41, the entire content of which is incorporated herein by reference.

Though the Nice Classification may be used for convenience herein, the WHO has modified its classification system multiple times, highlighting the difficulties associated with correctly phenotyping (e.g. the Evian classification of 1998, the Venice classification of 2003, the Dana Point classification of 2008, and the Nice Classification of 2013). The WHO's repeated modification to classification systems demonstrate a long felt need for a reliable and consistent system for assessing PH and reliably risk stratifying PH. The present subject matter provides valuable new tools for classifying subjects afflicted with PH and for evaluating a subject's risk, e.g., for subjects falling within Nice WHO Group I.

The Nice Classification categorizes subjects having a mPAP of >25 mmHg at rest as being afflicted with PH. The term PH encompasses PAH.

Nice WHO Group I is also known as PAH. The Nice Classification categorizes subjects having a mPAP of >25 mmHg at rest, a PCWP≤15 mmHg and a PVR>3 Wood units as being afflicted with PAH. Subtypes of PAH include Idiopathic PAH (IPAH); heritable PAH (e.g., due to a mutation in a bone morphogenetic protein receptor type 2 (BMPR2), activin receptor-like kinase type 1 (ALK1), or endoglin gene (ENG), mothers against decapentaplegic 9 (SMAD9), Caveolin 1 (CAV1), Potassium Channel, Two Pore Domain Subfamily K, Member 3 (KCNK3) or due to another unknown hereditary factor); drug-induced PAH and toxin-induced PAH (e.g., due to aminorex, fenfluramine and fenfluramine derivatives, dexfenfluramine, St. John's Wort, benflurex, interferon (IFN)-α or β, chemotherapeutic agents, dasatanib, phenylpropanolamine, cocaine, toxic rapeseed oil, selective serotonin reuptake inhibitors, amphetamines, L-tryptophan, and methamphetamines); PAH associated with a connective tissue disease (e.g., systemic sclerosis, lung fibrosis, systemic lupus erythematosus, mixed connective tissue disease, Sjögren syndrome, polymyositis, rheumatoid arthritis); an human immunodeficiency virus (HIV) infection; portal hypertension (i.e. portopulmonary hypertension (POPH)); a congenital heart disease (e.g., Eisenmenger syndrome and PAH after corrective cardiac surgery) not including left heart congenital diseases such as congenital or acquired left heart inflow/outflow obstructive lesions and congenital cardiomyopathies; and schistosomiasis.

Nice WHO Group I' includes PH resulting from pulmonary veno-occlusive disease (PVOD) and/or pulmonary capillary hemangiomatosis (PCH).

Nice WHO Group I" includes persistent pulmonary hypertension of the newborn.

Nice WHO Group II pulmonary hypertension is pulmonary hypertension owing to left heart disease, such as left heart disease relating to systolic dysfunction, diastolic dysfunction, or valvular disease. Group II also includes congenital or acquired left heart inflow/outflow obstructive lesions and congenital cardiomyopathies. In some embodiments, the present subject matter does not relate to WHO Group II hypertension. All references to PH or PAH with respect to embodiments of the present invention exclude pulmonary hypertension resulting from left heart disease. In left heart disease or left ventricular (LV) heart failure, the left side of the heart must work harder to pump the same amount of blood. Two types of left sided heart disease are systolic dysfunction and diastolic dysfunction. In systolic failure (also called systolic dysfunction), the left ventricle loses its ability to contract normally. The heart cannot pump with enough force to push enough blood into circulation. In diastolic failure (also called diastolic dysfunction), the left ventricle loses its ability to relax normally and the heart cannot properly fill with blood during the resting period between each beat. Left-sided ventricular or valvular diseases may produce an increase in left atrial pressure, with passive backward transmission of the pressure leading to increased mPAP. In this situation, PVR is normal or near normal (<3.0 Wood units) and there is no gradient between mPAP and pulmonary wedge pressure (transpulmonary gradient<12 mm Hg). In some patients with left heart disease, the elevation of mPAP is out of proportion to that expected from the elevation of left arterial pressure (transpulmonary gradient>12 mm Hg) and PVR is increased to 3.0 Wood units.

Nice WHO Group III is pulmonary hypertension owing to lung diseases and/or hypoxia, such as chronic obstructive pulmonary disease; interstitial lung disease; other pulmonary diseases with mixed restrictive and obstructive pattern; sleep-disordered breathing; alveolar hypoventilation disorders; chronic exposure to high altitude; and developmental lung abnormalities.

Nice WHO Group IV is chronic thromboembolic pulmonary hypertension (CTEPH).

Nice WHO Group V is pulmonary hypertension with unclear multifactorial mechanisms, such as chronic hemolytic anemia (e.g., chronic hereditary and acquired hemolytic anemias, including sickle cell disease, thalassemia, hereditary spherocytosis, stomatocytosis, and microangiopathic hemolytic anemia); hematologic disorders (such as myeloproliferative disorders and splenectomy; systemic disorders (such as sarcoidosis, pulmonary Langerhans cell histiocytosis, e.g., lymphangioleiomyomatosis, neurofibromatosis, vasculitis); metabolic disorders (such as glycogen storage disease, Gaucher disease, and thyroid disorders); and others, such as tumoral obstruction, fibrosing mediastinitis, chronic renal failure on dialysis, and segmental PH.

In some embodiments, a subject suffers from PH within WHO Group I, I', I", III, IV, or V. For example, the subject may suffer from PH within WHO Group I, I', or I".

In various embodiments, the subject suffers from PH within Group I, i.e., PAH. In some embodiments, the subject suffers from IPAH, heritable PAH, drug-induced PAH, toxin-induced PAH; PAH associated with a connective tissue disease; PAH associated with systemic sclerosis, lung fibrosis, systemic lupus erythematosus, mixed connective tissue disease, Sjögren syndrome, polymyositis, rheumatoid arthritis; PAH associated with a HIV infection; PAH associated with a portal hypertension; PAH associated with a congenital heart disease; PAH associated with a Eisenmenger syndrome; PAH after corrective cardiac surgery; PAH associated with schistosomiasis; PAH associated with chronic hemolytic anemia; PAH associated with a chronic hereditary or acquired hemolytic anemia; PAH associated with a sickle cell disease, thalassemia, hereditary spherocytosis, stomatocytosis, or microangiopathic hemolytic anemia, or persistent pulmonary hypertension of a newborn. In some embodiments, the subject suffers from IPAH and a connective tissue disease, systemic sclerosis, lung fibrosis, systemic lupus erythematosus, mixed connective tissue disease, Sjögren syndrome, polymyositis, rheumatoid arthritis; a HIV infection; portal hypertension; a congenital heart disease; Eisenmenger syndrome; congenital heart disease with systemic-to-pulmonary shunts, congenital heart disease with small defects, and schistosomiasis.

Aspects of the present subject matter relate to the diagnosis of PAH and the prophylactic treatment of PAH in subjects at risk of developing PAH. Thus, in certain embodiments, a subject is at risk of developing PAH. Subjects at risk of developing PAH include subjects having a mutation in a BMPR2, ALK1, ENG, SMAD9, CAV1, or KCNK3 gene; subjects with 1 or 2 parents who have been diagnosed with PAH, or 1, 2, 3, 4, 5, or more siblings who have been diagnosed with PAH; subjects who have been administered aminorex, a fenfluramine or fenfluramine derivatives, dexfenfluramine, St. John's Wort, benflurex, IFN-α or IFN-β, a chemotherapeutic agent, dasatanib, phenylpropanolamine, cocaine, toxic rapeseed oil, a selective serotonin reuptake inhibitor, an amphetamine, L-tryptophan, or a methamphetamine); subjects suffering from a connective tissue disease (e.g., systemic sclerosis, lung fibrosis, systemic lupus erythematosus, mixed connective tissue disease, Sjögren syndrome, polymyositis, rheumatoid arthritis); subjects infected with HIV infection; subjects suffering from a congenital heart disease (other than a left heart congenital disease such as congenital or acquired left heart inflow/outflow obstructive lesions and congenital cardiomyopathies); subjects suffering from schistosomiasis.

In some embodiments, a subject suffers from WHO Group I' PH. For example, the subject suffers from PVOD or PCH.

In some embodiments, a subject suffers from WHO Group II" PH.

In various embodiments, a subject does not suffer from a left heart disease.

In some embodiments, a subject suffers from WHO Group III PH. For example the subject may suffer from PH associated with a chronic obstructive pulmonary disease; interstitial lung disease; a pulmonary disease with a mixed restrictive and obstructive pattern; sleep-disordered breathing; an alveolar hypoventilation disorder; chronic exposure to high altitude; or a developmental lung abnormality. In certain embodiments, a subject at risk of developing PH suffers from a chronic obstructive pulmonary disease; interstitial lung disease; a pulmonary disease with a mixed restrictive and obstructive pattern; sleep-disordered breathing; an alveolar hypoventilation disorder; or a developmental abnormality, or has suffered from chronic exposure to high altitude.

In various embodiments, a subject suffers from WHO Group IV PH, such as CTEPH.

In various embodiments, a subject suffers from WHO Group V PH. For example the subject suffers from PH associated with chronic hemolytic anemia, a chronic hereditary or acquired hemolytic anemia, a sickle cell disease, thalassemia, hereditary spherocytosis, stomatocytosis, or microangiopathic hemolytic anemia, a hematologic disorder (such as a myeloproliferative disorder); a splenectomy; a systemic disorder (such as sarcoidosis or pulmonary Langerhans cell histiocytosis such as lymphangioleiomyomatosis, neurofibromatosis, or vasculitis); a metabolic disorder (such as a glycogen storage disease, Gaucher disease, or a thyroid disorder); or a tumoral obstruction, fibrosing mediastinitis, chronic renal failure on dialysis, or segmental PH. In certain embodiments, a subject at risk of developing PH suffers from chronic hemolytic anemia (e.g., a chronic hereditary or acquired hemolytic anemia, such as sickle cell disease, thalassemia, hereditary spherocytosis, stomatocytosis, or microangiopathic hemolytic anemia); a hematologic disorder (such as a myeloproliferative disorder); a splenectomy; a systemic disorder (such as sarcoidosis or pulmonary Langerhans cell histiocytosis such as lymphangioleiomyomatosis, neurofibromatosis, or vasculitis); suffers from a metabolic disorder (such as a glycogen storage disease, Gaucher disease, or a thyroid disorder); or a tumoral obstruction, fibrosing mediastinitis, or chronic renal failure on dialysis.

In certain embodiments, the subject does not comprise sleep apnea or renal disease (e.g. chronic renal disease). In some embodiments, the subject does not comprise obstructive sleep apnea, end stage renal disease, or hypertrophic cardiomyopathy.

Sudden Cardiac Death

PH can lead to sudden cardiac death (SCD). SCD is a sudden, unexpected death caused by loss of heart function (sudden cardiac arrest). SCD is not a heart attack (myocardial infarction) but can occur during a heart attack. SCD occurs when the electrical system to the heart malfunctions and suddenly becomes very irregular (i.e., there is an arrhythmia). The most common life-threatening arrhythmia is ventricular fibrillation, which is an erratic, disorganized firing of impulses from the ventricles (the heart's lower chambers). When this occurs, the heart is unable to pump blood and death will occur within minutes, if left untreated.

Binding Ligands for Biomarkers

As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab}$ and $F_{(ab')2}$ fragments, and an $F_{ab}$ expression library. By "specifically bind" or "immunoreacts with" is meant that the antibody reacts with one or more antigenic determinants of the desired antigen and does not react (i.e., bind) with other polypeptides or binds at much lower affinity ($K_d > 10^{-6}$) with other polypeptides.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ea., 2nd ed. Raven Press, N.Y. (1989)). The variable regions of each light/heavy chain pair form the antibody binding site.

The term "monoclonal antibody" (MAb) or "monoclonal antibody composition," as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs." Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, a scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ µM; preferably $\leq 100$ nM and most preferably $\leq 10$ nM.

Antibodies can be produced according to any method known in the art.

Methods of preparing monoclonal antibodies are known in the art. For example, monoclonal antibodies may be prepared using hybridoma methods, such as those described by Kohler and Milstein (1975) Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a full length protein or a fragment thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (see pp. 59-103 in Goding (1986) Monoclonal Antibodies: Principles and Practice Academic Press) Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In some examples the antibodies to an epitope for an interested protein as described herein or a fragment thereof are humanized antibodies. Humanized forms of non-human (e.g., murine) antibodies are chimeric molecules of immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al. 1986. Nature 321:522-525; Riechmann et al. 1988. Nature 332:323-329; Presta. 1992. Curr. Op. Struct. Biol. 2:593-596). Humanization can be essentially performed following methods of Winter and co-workers (see, e.g., Jones et al. 1986. Nature 321:522-525; Riechmann et al. 1988. Nature 332:323-327; and Verhoeyen et al. 1988. Science 239:1534-1536), by substituting rodent CDRs or CDR sequences for the corresponding sequences of a human antibody. Accordingly, such humanized antibodies are chimeric antibodies (e.g., U.S. Pat. No. 4,816,567), wherein substantially less than an intact human variable domain has been substituted by the corresponding sequence from a non-human species.

In another example the antibodies to an epitope of an interested protein as described herein or a fragment thereof are human antibodies. Human antibodies can also be produced using various techniques known in the art, including phage display libraries (Hoogenboom and Winter. 1991. J. Mol. Biol. 227:381-388; Marks et al. 1991. J. Mol. Biol. 222:581-597) or the preparation of human monoclonal antibodies (e.g., Cole et al. 1985. Monoclonal Antibodies and Cancer Therapy Liss; Boerner et al. 1991. J. Immunol. 147(1):86-95). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in most respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al. 1992. Bio/Technology 10:779-783; Lonberg et al. 1994. Nature 368:856-859; Morrison. 1994. Nature 368:812-13; Fishwild et al. 1996. Nature Biotechnology 14:845-51; Neuberger. 1996. Nature Biotechnology 14:826; Lonberg and Huszar. 1995. Intern. Rev. Immunol. 13:65-93. U.S. Pat. No. 6,719,971 also provides guidance to methods of generating humanized antibodies.

Exemplary antibodies against human SCN5A protein include, but are not limited to, antibodies obtained from "Thermo Scientific online" (e.g., Cat. No. PAS-34190; Cat. No. MA1-27429; Cat. No. PAS-39462; Cat. No. PAS-36074, and more can be found at the website www.pierce-antibodies.com), antibodies obtained from "abcam.com" (e.g., ab53724, ab62388, ab116706, ab86321, and more can be found at its website www.abcam.com), antibodies obtained from Santa Cruz Biotech (e.g., sc-271255, sc-81631, sc22758, sc23174, and more can be found at its website www.scbt.com); any commercially available antibodies against SCN5A, and any antibodies that are generated by a known method in the art utilizing the full-length protein or a fragment of human SCN5A (e.g., residues 159-412, residues 159-178, residues 842-862, residues 1201-1224, any fragment or full length of SEQ ID NO 5).

Alternative Splicing of SCN5A and Right Heart Failure

Figure 4:
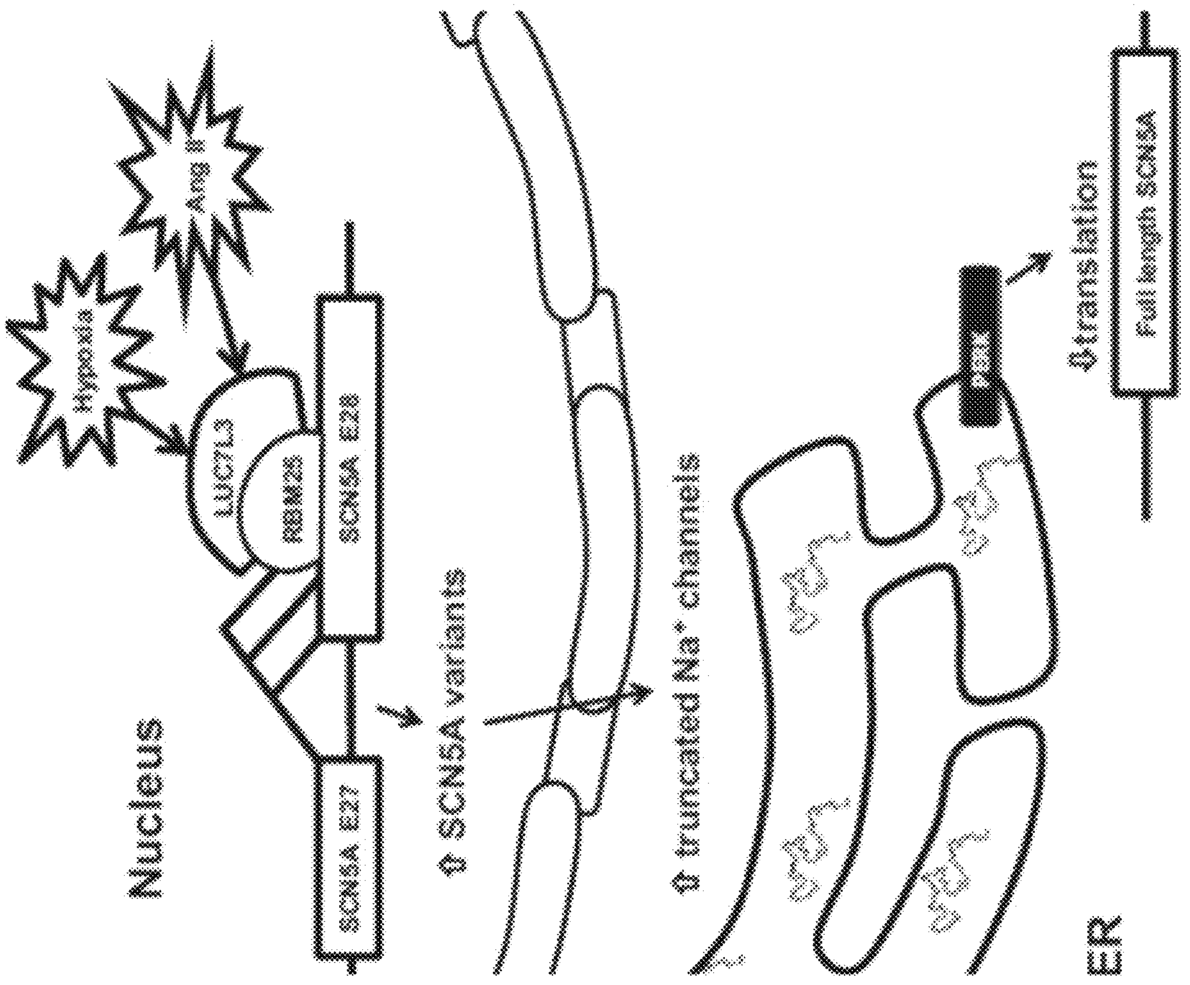
FIG. 4 is a cartoon showing HIF-1α- and Ang II-mediated alternative splicing of SCN5A and subsequent triggering of the unfolded protein response (UPR) (via PERK). ER=endoplasmic reticulum.
Figure 5:
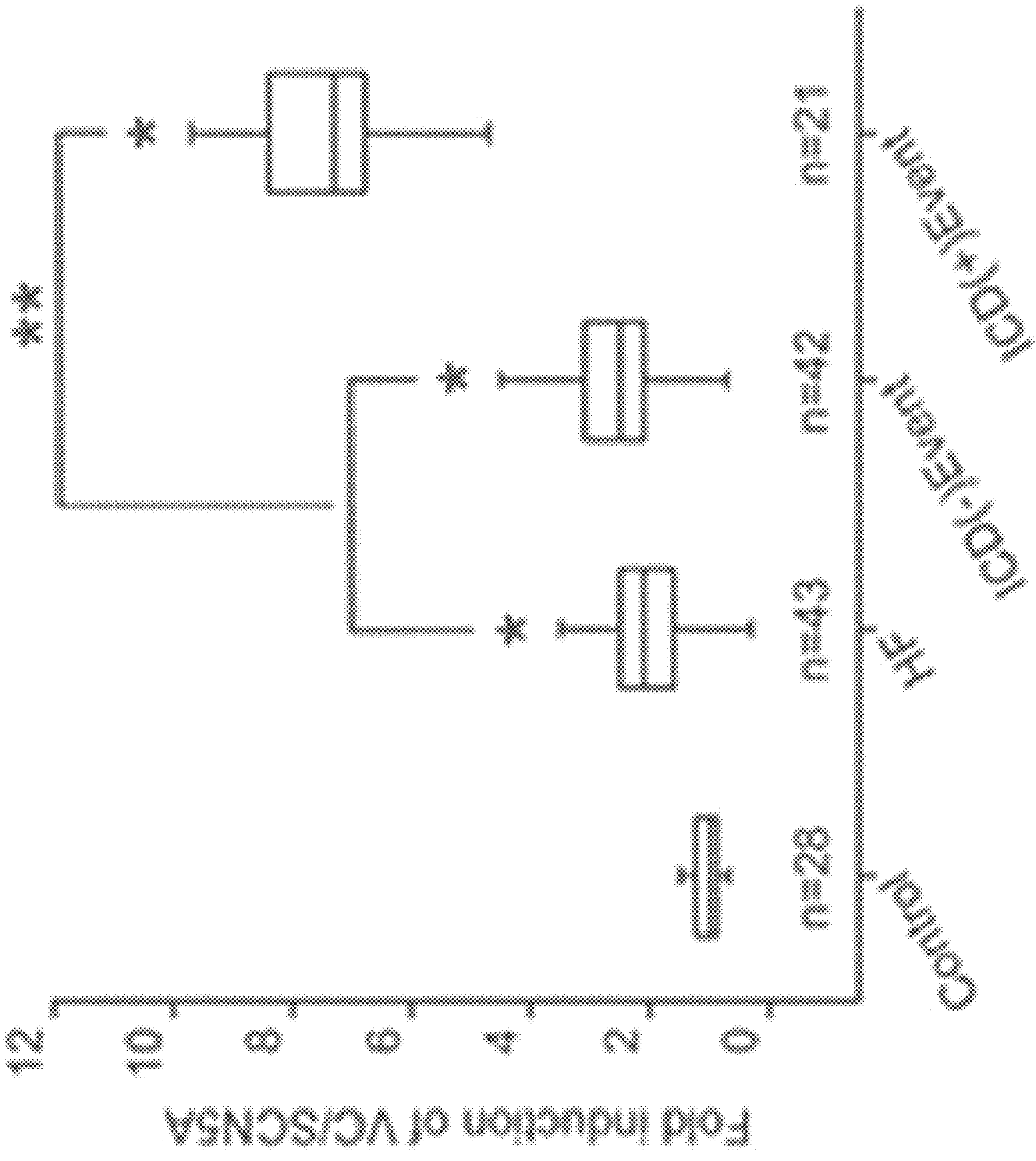
FIG. 5 is a graph showing increased splice variant (SV) expression in those with defibrillator shocks (* and **=p<0.005). VC=full transcript levels; ICD=implanted cardioverter-defibrillator; HF=heart failure.

Alternative splicing of SCN5A, though studied in conjunction with left heart failure, has not, prior to the invention, been connected with right heart failure. Two SFs influence alternative splicing of SCN5A during cellular hypoxia and exposure to Ang II (FIG. 4) (Shang et al., Circ Res. 2007; 101(11):1146-54). This splicing complex causes a frameshift mutation with a premature stop codon leading to increased levels of two SV which are truncated nonfunctional proteins (Gao et al., Circ Arrhythm Electrophysiol. 2013; 6(5):1018-24). Expression of these SV cause a dominant negative effect that is dose dependent, decreasing cardiomyocyte membrane potential by 50% to levels equivalent to that seen in the Brugada syndrome (Shang et al., Circ Res. 2007; 101(11):1146-54). Transcript levels of these SF and SV correlate with protein expression in human left heart failure ventricular tissue and recent work by Dr. Samuel Dudley has demonstrated strong correlations between myocardial SV levels, circulating WBC SV mRNA levels and defibrillator shocks in chronic left heart failure patients (FIG. 5) (Gao et al., Circ Arrhythm Electrophysiol. 2013; 6(5):1018-24; Gao et al., J Am Coll Cardiol. 2014; 63(21):2261-9). SV are a promising point-of-care assay for SCD.

Surprisingly, alternative splicing, the UPR and mitochondrial stress contribute to right heart failure. ER stress can lead to mitochondrial dysfunction in several chronic disease states including cardiac arrhythmia (Rainbolt et al., Trends Endocrinol Metab. 2014; 25(10):528-37; Rutledge and Dudley, Expert Rev Cardiovasc Ther. 2013; 11(7):799-801; Vannuvel et al., J Cell Physiol. 2015). The physical interaction between the organelles through mitochondrial associated membranes (MAM) allow for intimate communication of biologic molecules (Vannuvel et al., J Cell Physiol. 2015). SCN5A SV have been shown to localize to the ER (as opposed to the cellular membrane as is the case for full length SCN5A) and activate PERK (protein kinase RNA-like endoplasmic reticulum kinase), a transmembrane protein involved in the UPR that acts as a sensor of ER stress in cardiomyocytes (Gao et al., Circ Arrhythm Electrophysiol. 2013; 6(5):1018-24). Without wishing to be bound by any scientific theory, sublethal and transient ER stress in the form of accumulated misfolded proteins decreases mitochondrial oxygen consumption and temporarily induces mitochondrial fragmentation, which alters metabolism in the cells that undergo alternative splicing of SCN5A (Vannuvel et al., J Cell Physiol. 2015). Increases in SV may therefore signal RV metabolic changes in addition to electrochemical changes in PAH.

Hypoxia and RAS may impact the RV in PAH. Hypoxia is the upstream trigger for transcriptional modifications of SCN5A through the RAS (Gao et al., Circ Arrhythm Electrophysiol. 2013; 6(5):1018-24). RAS plays a pivotal role in the hypertrophy and proliferation of pulmonary artery smooth muscle cells (PASMCs) that leads to remodeling in pulmonary hypertension (Morrell et al., Am J Physiol. 1995; 269:H1186-94; Hatakeyama et al., J Biol Chem. 1994; 269(39):24316-20; Tuder et al., Clin Chest Med. 2013; 34(4):639-50). Independent of vascular remodeling, angiotensin converting enzyme (ACE) is increased >3-fold in the RV as compared to the left ventricle and in areas of RV fibrosis specifically during hypoxic stress (Morrell et al., Cardiovasc Res. 1997; 34(2):393-403; Maron et al., Pulm Circ. 2014; 4(2):200-10). Increased pulmonary endothelial ACE activity has been documented in the explanted lungs of PAH patients, and ACE2 (a counterregulatory homolog of ACE) and HIF-1α expression increases in failing RVs of cardiac transplant recipients (Gao et al., Circ Arrhythm Electrophysiol. 2013; 6(5):1018-24; Morrell et al., Cardiovasc Res. 1997; 34(2):393-403; Zhang et al., Am J Physiol Lung Cell Mol Physiol. 2009; 297(4):10). Without wishing to be bound by any scientific theory, this implies that hypoxia-RAS cross-talk may contribute to modulating the RV phenotype in PAH patients.

Cellular Stress and Metabolism in PAH

Normoxic induction of HIF-1α leads to reduced mitochondrial oxidative metabolism, fission of mitochondria and PASMC proliferation leading to pulmonary vascular disease in both animals and humans (Marsboom et al., Circ Res. 2012; 110(11):1484-97). The shift of cellular metabolism to aerobic glycolysis as the result of mitochondrial injury (i.e., the Warburg effect) has long been described in oncogenesis (Weinberg et al., Proc Natl Acad Sci USA. 2010; 107(19): 8788-93). Recently, glycolytic shift has been detected not only in the pulmonary vasculature but also in the RV of PAH patients by increased glucose uptake on FDG-PET (Lundgrin et al., Ann Am Thorac Soc. 2013; 10(1):1-9). However, a direct connection between HIF-1α and metabolic changes in the RV of PAH patients has not been established. Pathways which preferentially or uniquely impact the RV over the vasculature may explain why survival after cardiopulmonary resuscitation appears to be independent of hemodynamic impairment (Hoeper et al., Am J Respir Crit Care Med. 2002; 165(3):341-4). Thus, there is a need to refine "classic" PH risk stratification and explore more sensitive markers of prognosis. Without wishing to be bound by any scientific theory, the previously undefined relationship between HIF-1α and the metabolic shift in the RV of PAH patients may be due to chronically increased ER stress by way of SCN5A alternative splicing and the UPR (Rainbolt et al., Trends Endocrinol Metab. 2014; 25(10):528-37).

UPR, arrhythmogenesis, and the RV phenotype in PAH may be linked. Prolonged corrected QT (QTc) increases the risk of arrhythmias and death in PAH (Rich et al., Int J Cardiol. 2013; 167(3):669-76). In a monocrotaline model of pulmonary hypertension, QTc is prolonged and associated with spontaneous ventricular tachycardia in vivo and in the explanted RV (Tanaka et al., Am J Respir Cell Mol Biol. 2013; 49(3):426-36). The SV products of SCN5A accumulate in the ER causing organelle stress and triggering the UPR, which causes downregulation of multiple ion channels including potassium channels (Gao et al., Circ Arrhythm Electrophysiol. 2013; 6(5):1018-24). Loss of function mutations in the potassium channel subfamily K, member 3 (KCNK3) have recently been identified in heritable and idiopathic PAH (Chung et al., N Engl J Med. 2013; 369 (22):2162). Without wishing to be bound by any scientific theory, inherited or acquired potassium channel changes act synergistically with alternative splicing of SCN5A (triggered by hypoxia-RAS activation) and lead to electrophysiologic disturbance captured on electrocardiogram (EKG) as prolonged QTc in PAH. The UPR has been shown to contribute to left ventricular fibrosis, hypertrophy, and arrthymogenesis and blocking downstream effectors of the UPR rescues SCN5A channel conductance (Liu et al., Int J Mol Sci. 2016; 17(1)). While the UPR serves primarily as a homeostatic measure during times of cellular stress, prolonged activation of the UPR might contribute to maladaptive ventricular remodeling (Liu et al., Int J Mol Sci. 2016; 17(1)).

RV metabolism may be explored using an FDG-PET scan. Multiple studies have demonstrated FDG-PET may serve as a novel RV imaging end point in PAH based on the hypothesis that the RV increases glycolysis and undergoes a shift from fatty acid oxidation when compromised (Lundgrin et al., Ann Am Thorac Soc. 2013; 10(1):1-9; Fang et al., Pulm Circ. 2012; 2(3):365-72; Oikawa et al., J Am Coll Cardiol. 2005; 45(11):1849-55; Wang et al., J Nucl Cardiol. 2013; 20(2):242-52; Ahmadi et al., Curr Cardiol Rep. 2015; 17(1): 555). While accepted cut-offs for standardized uptake value (SUV) in various regions of the chest (RV and pulmonary parenchyma) have not been established, the RV/left ventricle ratio of SUV has been studied and appears to track with PAH therapy (33). FDG-PET therefore serves as a reasonable target of investigation to study altered metabolism in RV cardiomyocytes in vivo in PAH patients.

GENERAL DEFINITIONS

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

In various embodiments, and in the context of protein or mRNA levels, a "normal" amount refers to a normal amount of a protein or mRNA in an individual known not to be diagnosed with PH. The amount of a protein or mRNA can be measured in a test sample and compared to a "normal control" level, utilizing techniques such as reference limits, discrimination limits, or risk defining thresholds to define cutoff points and abnormal values (e.g., for PH or SCD). Depending on the context, the normal control level means the level of a protein or mRNA typically found in a subject known to not be afflicted with PH. In some instances, the normal control level may be obtained by calculating the average of the levels of a protein or mRNA in subjects not afflicted with PH. Such normal control levels and cutoff points may vary based on whether a protein or mRNA is used alone or in a formula combining with other proteins or mRNA into an index.

The level that is determined may be the same as a control level or a cut off level or a threshold level, or may be increased or decreased relative to a control level or a cut off level or a threshold level. In some aspects, the control subject (or subjects, e.g., in the case of an averaged normal control level) is a matched control of the same species, gender, ethnicity, age group, smoking status, BMI, current therapeutic regimen status, medical history, or a combination thereof, but differs from the subject being diagnosed in that the control does not suffer from the disease in question or is not at risk for the disease.

In some embodiments, a control level for SCD can be a database of protein/mRNA patterns from previously tested subjects who did not suffer from SCD over a clinically relevant time horizon.

In various embodiments, an "increased level" may be determined, e.g., relative to a control level or a previous level determined for a subject. As used herein in certain embodiments, the term "increased" with respect to a level (e.g., expression level, protein level, biological activity level) may refer to any % increase above a control level or previous level for a subject, depending on the context. The increased level may be at least or about a 1, 2, 3, 4, or 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, at least or about a 95% increase, relative to a control level or previous level.

In various embodiments, a "decreased level" may be determined, e.g., relative to a control level or a previous level determined for a subject. As used herein in certain embodiments, the term "decreased" with respect to a level (e.g., expression level, protein level, biological activity level) may refer to any % decrease above a control level or previous level for a subject, depending on the context. The decreased level may be at least or about a 1, 2, 3, 4, or 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, at least or about a 95% decrease, relative to a control level or previous level.

Polynucleotides, polypeptides, or other agents are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. Purified also defines a degree of sterility that is safe for administration to a human subject, e.g., lacking infectious or toxic agents.

By a "substantially pure" compound is meant a compound that has been separated from the components that naturally accompany it. Typically, a compound is substantially pure when it is at least 60%, 70%, 80%, 90%, 95%, or even 99%, by weight, free from the proteins and naturally-occurring organic molecules with which it is naturally associated.

With respect to a cell type, an isolated or purified cell is one that has been substantially separated or purified away from other biological components of the organism in which the cell naturally occurs, such as other cells of the organism. For example, an isolated lymphocyte cell population is a population of lymphocytes that is substantially separated or purified away from other blood cells, such as red blood cells. In a particular example, an isolated CD4 positive cell population is a population of CD4 positive cells that is substantially separated or purified away from other blood cells, such as CD8 positive cells. In various embodiments, an isolated or purified cell is at least about 60%, 70%, 80%, 90%, 95%, 99% or more pure. In one example, an isolated CD4 positive T-cell population is at least 95% pure, such as at least 99% pure. In another particular example, an isolated B-cell population is a population of B-cells that is substantially separated or purified away from other blood cells, such as T-cells. In one example, an isolated B-cell population is at least 95% pure, such as at least 99% pure. An enriched population of white blood cells (e.g., buffy coat fraction) is a population that have been separated from red blood cells, e.g., by density gradient. For example, the white blood cells may be enriched to a level of about 20%, 25%, 30%, 35%, 40%, 45%, 50%, 55%, or more. For example, cells may be enriched from a primary bodily source, such as a body fluid, such as blood. In various embodiments, the blood is peripheral blood obtained, collected, or provided from a subject. In some embodiments, the cells are peripheral blood mononuclear cells (PBMCs).

The term "subject" as used herein includes all members of the animal kingdom that may suffer from the indicated disorder. In some aspects, the mammal is a human. In some embodiments, the subject is a mammal, and in some aspects, the subject is a human. Certain embodiments are applicable to companion animals such as dogs and cats as well as livestock such as cows, horses, sheep, goats, pigs, and other domesticated and wild animals. Subjects may also be non-human primates (e.g., monkeys or chimpanzees), rodents (e.g., mice, hamsters, rats), and rabbits.

As used herein, a "treatment" or "therapy" is an approach for obtaining beneficial or desired results, including clinical results. For purposes of this disclosure, beneficial or desired clinical results include, but are not limited to, alleviation or amelioration of symptoms, diminishment of extent of disease, stabilized (i.e., not worsening) state of disease, delay or slowing of disease progression, amelioration or palliation of the disease state, and recovery (whether partial or total), whether detectable or undetectable. Treating a subject can also mean prolonging survival as compared to expected survival if not receiving treatment.

Insofar as the methods of the present disclosure are directed to compositions and methods for treating a disease or disease state, it is understood that the term "prevent" does not require that the disease state (e.g., PAH or sudden cardiac death) be completely thwarted. The term "prevent" can encompass partial effects when the agents disclosed herein are administered as a prophylactic measure. The prophylactic measures include, without limitation, administration to one (or more) individual(s) who is suspected of developing or being at risk of developing, e.g., PAH. With respect to SCD, the prophylactic measures include, without limitation, administration to one (or more) individual(s) who has been diagnosed with PAH. Preventing SCD comprises delaying SCD relative to the likely (e.g., greater than 30%, 40%, 50% or 51% likely) time of death of a corresponding subject not receiving treatment.

As used herein, "assaying" means using an analytic procedure to qualitatively assess or quantitatively measure the presence or amount or the functional activity of a target entity. For example, assaying the level of a full-length SCN5A protein, a full-length SCN5A protein-encoding mRNA, a SCN5A splice variant protein, or a SCN5A splice variant protein-encoding mRNA means using an analytic procedure (such as an in vitro procedure) to qualitatively assess or quantitatively measure the presence or amount of the full-length SCN5A protein, the full-length SCN5A protein-encoding mRNA, the SCN5A splice variant protein, or the SCN5A splice variant protein-encoding mRNA.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1: Alternative Splicing of the Cardiac Sodium Channel in Pulmonary Arterial Hypertension While right ventricular (RV) failure is felt to be the proximate cause of death in PAH, the RV phenotype is not well understood. Patients with PAH are at increased risk for SCD. Alternative splicing of the cardiac sodium channel SCN5A leads to increased expression of splice variants (SV) and has been implicated in ventricular remodeling and SCD in left heart failure. Experiments were performed to determine whether PAH patients have increased expression of SCN5A SV messenger ribonucleic acid (mRNA) as compared to healthy controls. In this study, increased SV mRNA correlates with hypoxia inducible factor-1α (HIF1α) (which induces alternative splicing) mRNA levels and RV function respectively in PAH patients.

A cross-sectional study was performed comparing mRNA levels of splicing factors (SF) and SV in prevalent World Health Organization Group I PAH patients to levels in healthy control subjects. RNA extraction and qPCR were performed (PAXgene Blood RNA Kit, Qiagen, Valencia, Calif.). Levels of mRNA expression of SCN5A SV normalized to full length transcript SCN5A levels, LUC7L3, and HIF1α were quantified and concentrations and purity of RNA isolates tested (NanoDrop8000, Thermo Scientific, Carlsbad, Calif.). Unpaired Student t tests and Spearman's rho were used to compare mean values and correlation respectively.

Figure 6:
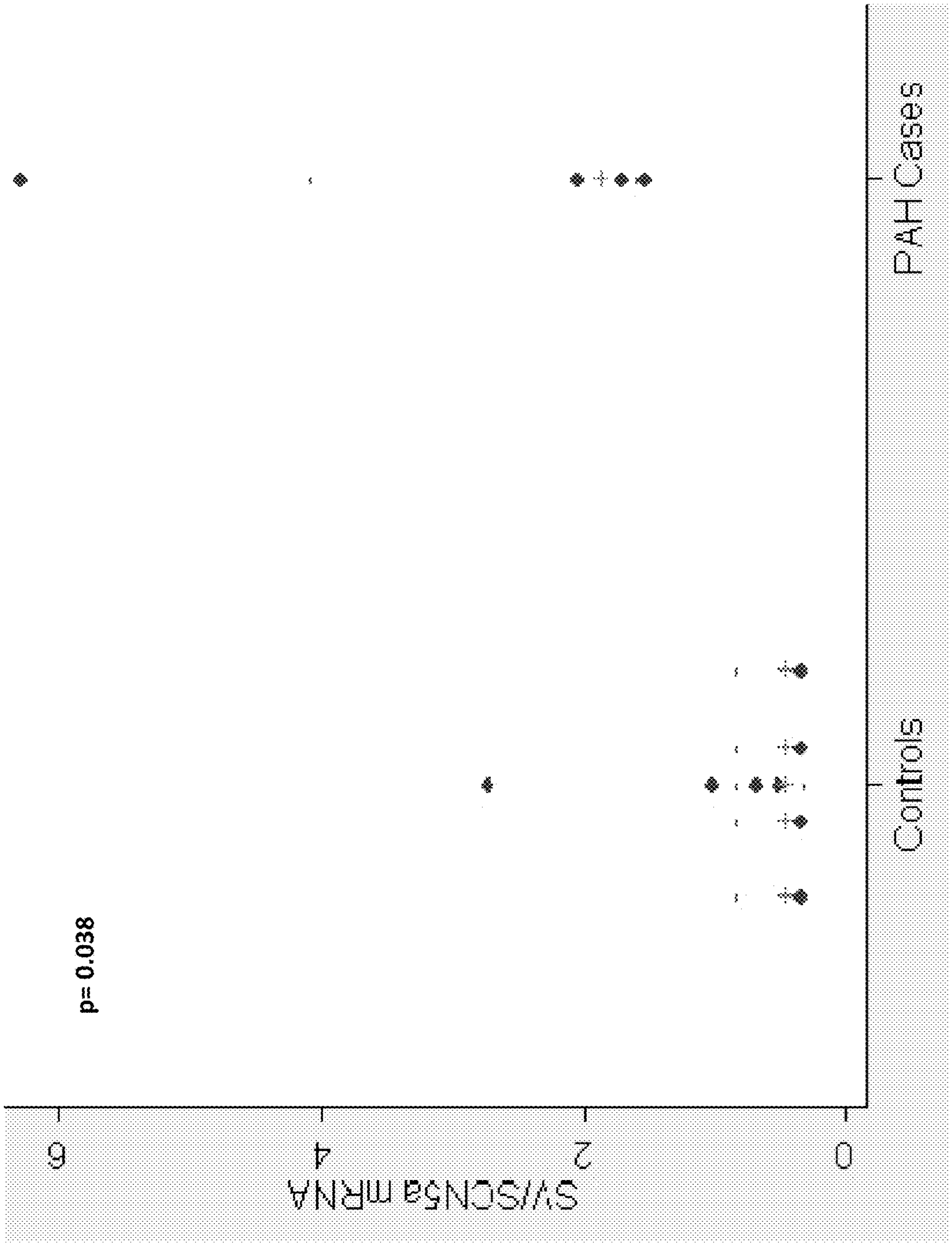
FIG. 6 is a graph showing a four-fold increase in SV/SCN5A mRNA in PAH cases versus controls.
Figure 7A:
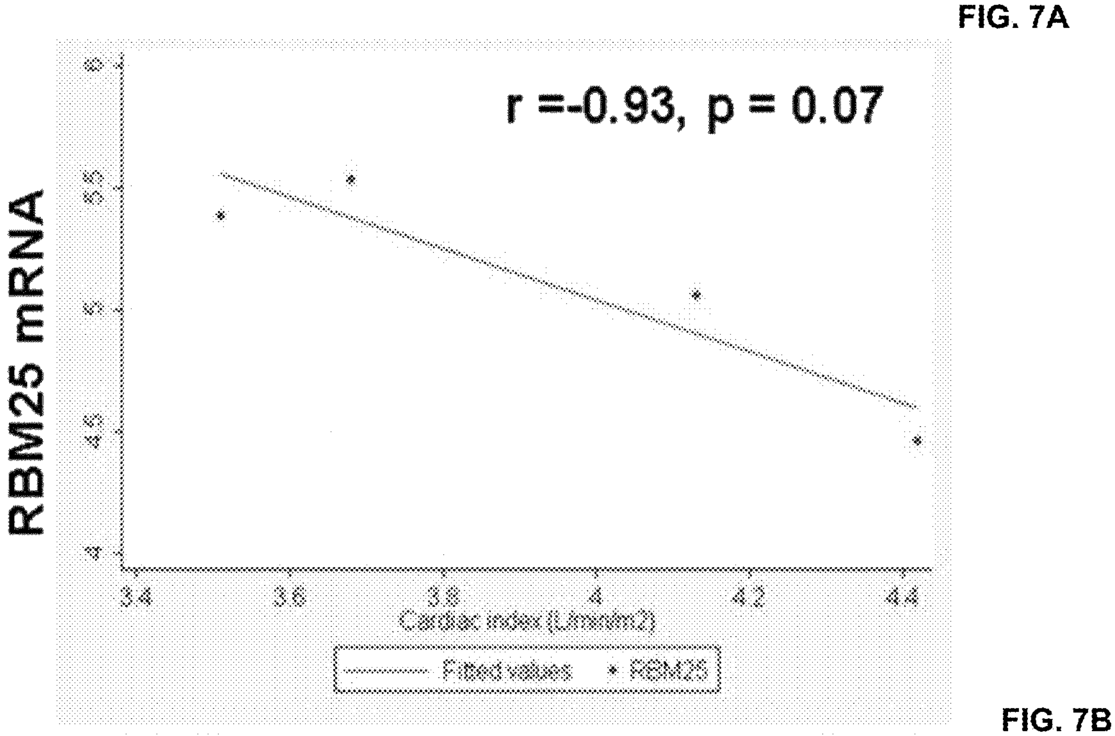
FIGS. 7A and B are a graphs showing the correlation between RBM25 (FIG. 7A) and LUC7L3 (FIG. 7B) and cardiac index in PAH cases.
Figure 7B:
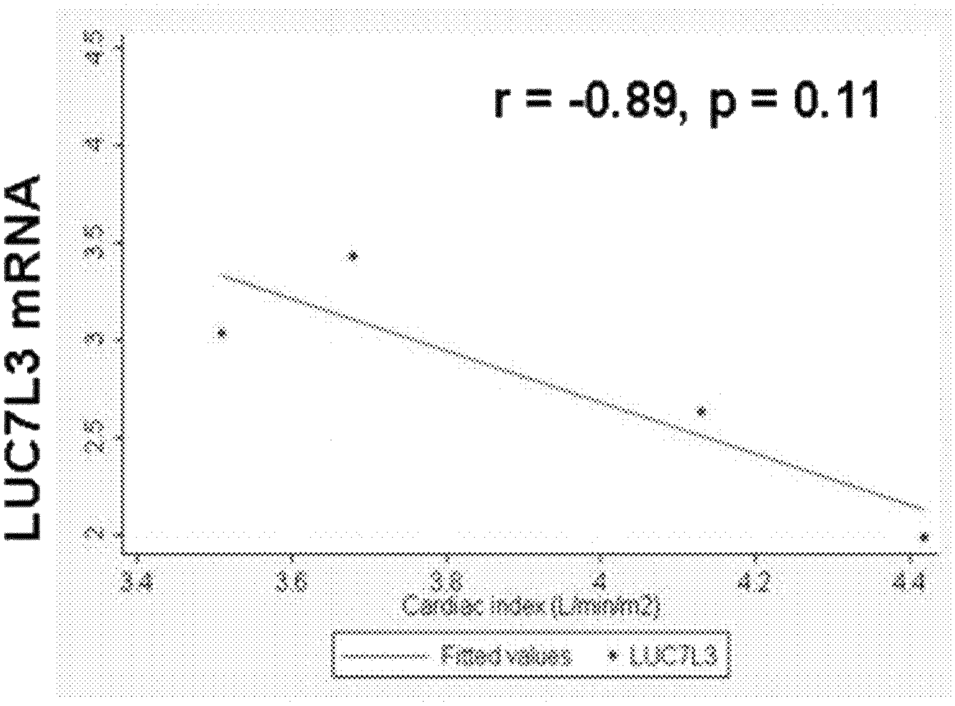

Five PAH patients (cases) and ten healthy controls were included (Table 1). Among cases, 60% had connective tissue disease associated PAH, 60% had advanced symptoms (WHOfunctional class III/IV, meaning shortness of breath with minimal activity or rest, respectively) and 80% were on combination (more than 1 drug from the 3 major drug classes) PAH therapy. There was a 4-fold increase in the relative expression of circulating SV mRNA isolated from whole blood of PAH patients compared with controls (SCN5A/SV 1.13 in cases vs. 0.29 in control subjects, $p=0.04$) (FIG. 6). There were strong correlations between SF (LUC7L3) levels and HIF-1α expression ($r=0.74$-$0.82$, $p=0.05$-$0.09$) as well as inverse correlations between SF levels and cardiac index ($r=-0.89$-$-0.93$, $p=0.07$-$0.11$) in cases. Effect sizes are consistent with prior published data on patients with systolic heart failure linking these expression levels with a clinically meaningful end point (e.g., defibrillator discharges) (Gao et al., (2011) Circulation. 2011; 124(10):1124-31). In addition, there was a strong correlation between HIF1α and RBM25 ($r=0.82$, $p=0.05$) and possible correlation with LUC7L3 ($r=0.74$, $p=0.09$). An inverse correlation was observed between RBM25 and cardiac index (CI) ($r=-0.93$, $p=0.07$) and possibly LUC7L3 ($r=-0.89$, $p=0.11$) and CI (FIG. 7).

TABLE 1

Patient Characteristics

| | PAH Cases (n = 5) | Controls (n = 10) |
|---|---|---|
| Age, yr | 58 (39-65) | 33.5 (32-35) |
| Female, % | 80 | 30 |
| WBC × $10^{-9}$/L | 6.9 (4.2-16.1) | 7.2 (6-7.4) |

TABLE 1-continued

| Patient Characteristics | | |
|---|---|---|
| | PAH Cases (n = 5) | Controls (n = 10) |
| BMI, kg/$m^2$ | 36.5 (36.1-37.6) | 25 (23.4-26.3) |
| White, n (%) | 100 | 70 |
| QTc, msec | 430 (421-484) | |
| PDE5i, % | 80 | |
| ERA, % | 40 | |
| Prostacyclin | 60 | |
| 6MWD, m | 472 (185-620) | |
| FC III/IV, % | 20% | |
| RAP, mmHg | 7 (3-11) | |
| mPAP, mmHg | 37 (25-40) | |
| PCWP, mmHg | 10 (7-15) | |
| CO, L/min | 7.19 (6.62-7.69) | |
| PVR, Wood units | 3.32 (3.02-6.44) | |

Since the WHO Group I classification by definition excludes left-sided disease, these data show that alternative splicing of SCN5A contributes to RV dysfunction in PAH. These data also show that there is a strong correlation between HIF-1α, the major regulator of cardiopulmonary remodeling in PAH, and alternative splicing of SCN5A. These prevalent patients are well-controlled on targeted therapy (which may temper expression levels and lead to an underestimation of the magnitude of these observations). Thus, this data provides strong support for SCN5A's role in PAH.

Alternative splicing of SCN5A measured in whole blood was markedly increased in PAH patients as compared with levels in healthy controls. There were strong correlations between alternative splicing and HIF-1α expression (a major regulator of cardiopulmonary remodeling in PAH) as well as cardiac index.

Figure 8:
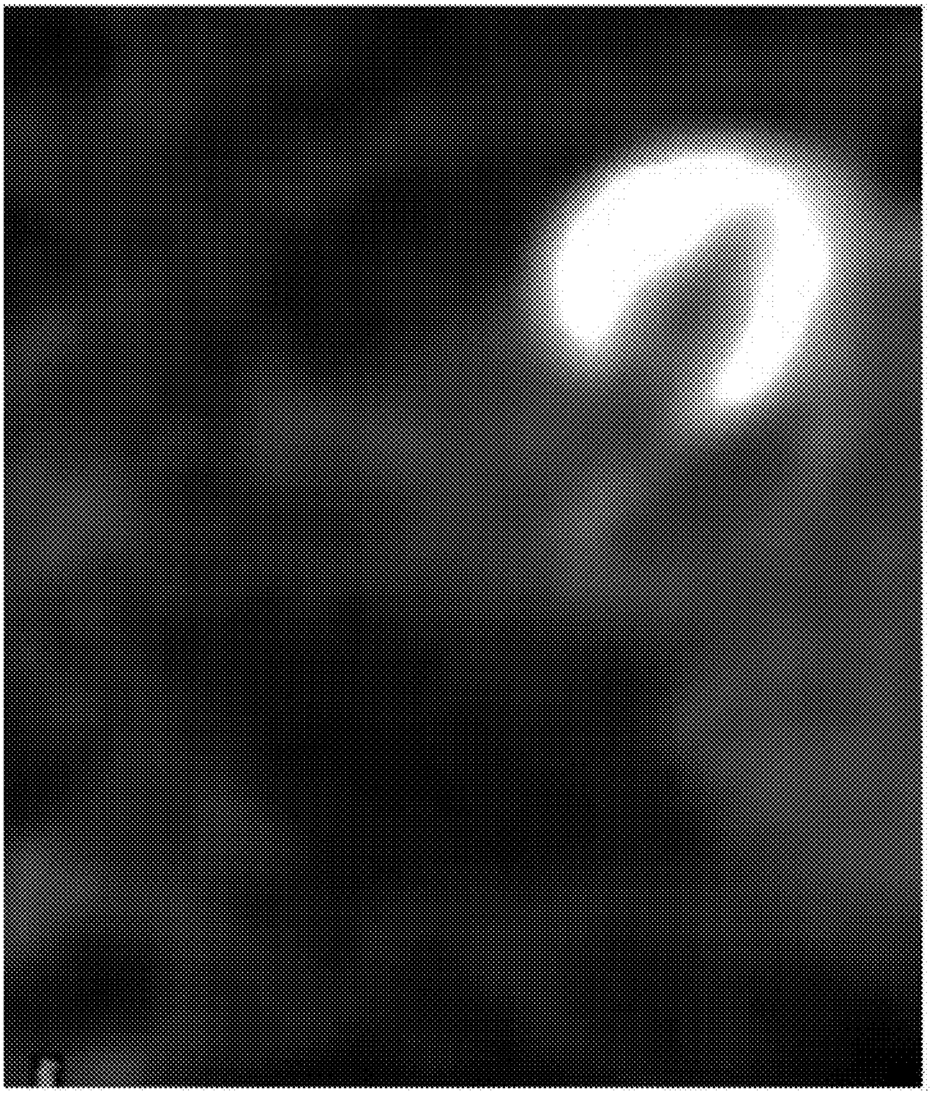
FIG. 8 is a picture of a positron emission tomography (PET) scan showing an example of 2-deoxy-2[18F]flouro-D-glucose positron emission tomography (FDG-PET) cardiac uptake in a PAH patient.
Figure 9:
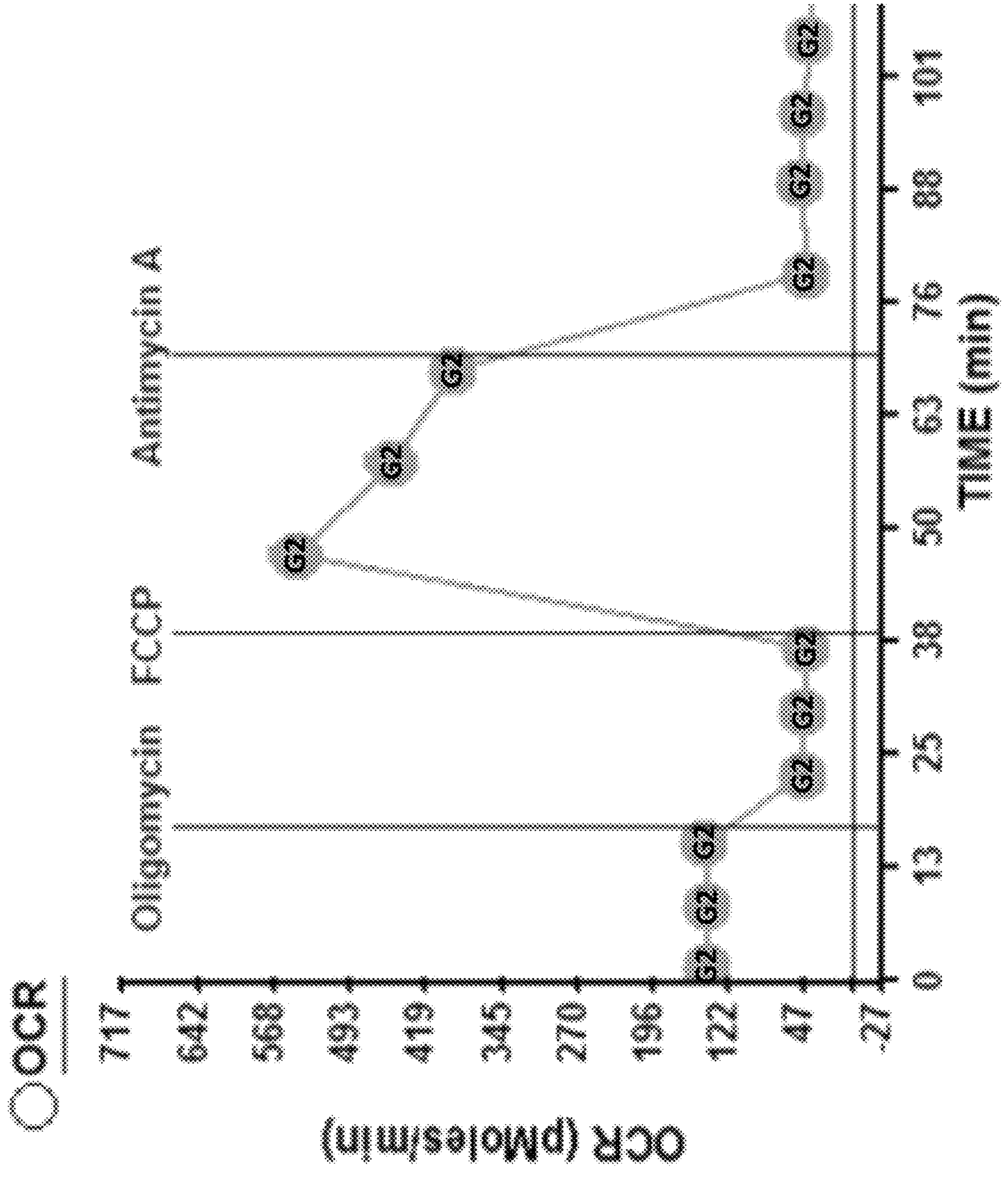
FIG. 9 is a graph showing a mitochondrial respiration profile in a patient sample. OCR=oxygen consumption rate; Time 0-13 min is basal respiration; time 13-38 min is proton leak; time 38-45 min is maximal respiration; time 45-70 min is spare capacity; time 80 to test end is non mitochondrial respiration.
Figure 10:
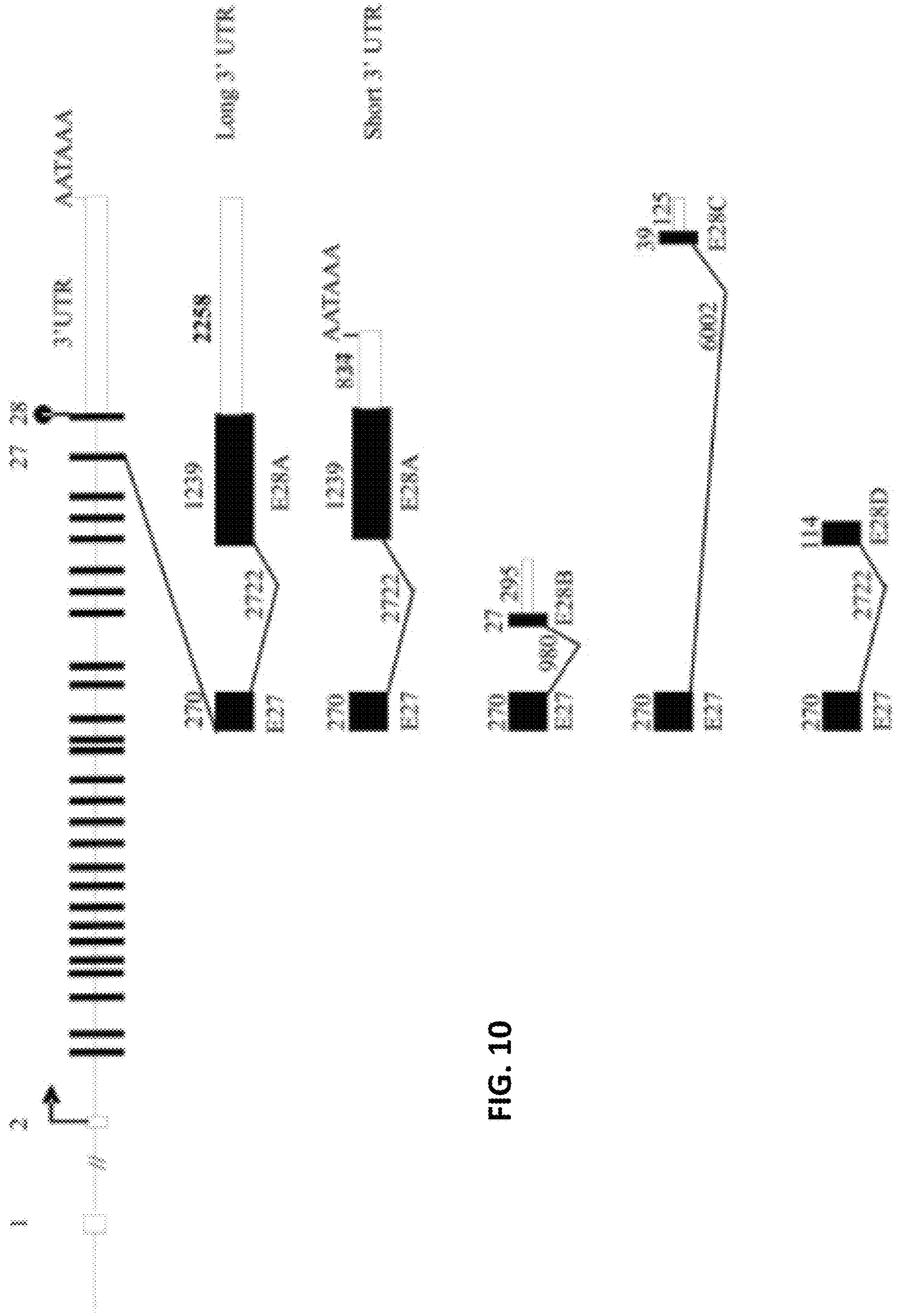
FIG. 10 is an illustration of the E28B, E28C, and E28D C-terminal splice variants of SCN5A, as well as full-length SCN5A (E28A). The top line represents the genomic structure of SCN5A. Untranslated, translated, and nontranscribed sequences are shown as open bars, closed bars, and lines, respectively. The arrow and black dot indicate the start codon at exon 2 and the terminal codon, respectively. Splicing patterns for exon 28 (E28B, E28C, and E28D C-terminal splice variants of SCN5A, as well as full-length SCN5A (E28A)) are identified below. Numbers indicate the nucleotide length of the exons and introns in base pairs.
Figure 11:
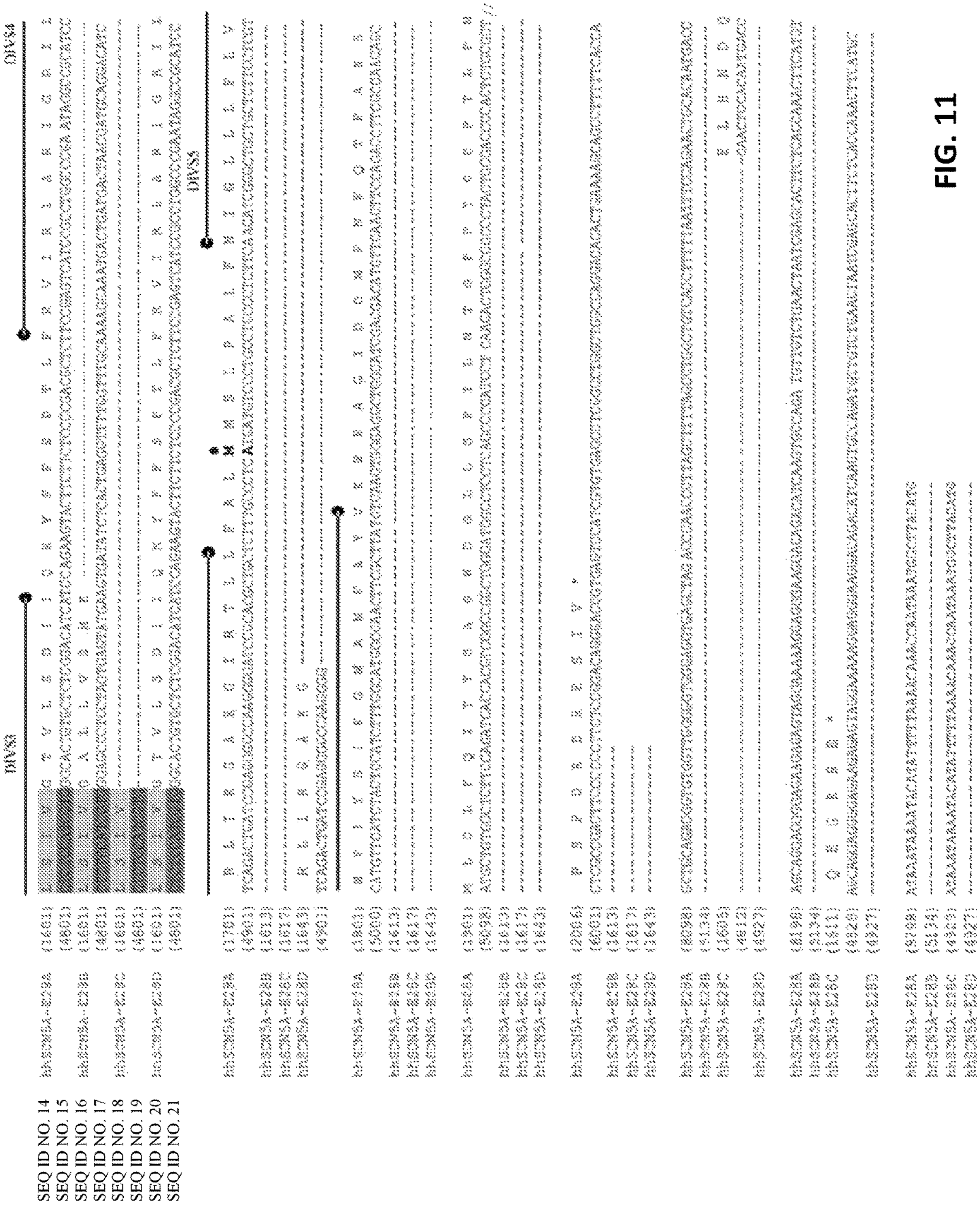
FIG. 11 is an alignment of the nucleotide and amino acid sequences (single letter) of the SCN5A transcriptional variants. The variant name and nucleotide base pairs numbering starting at the initial AUG codon are indicated at the left. The sequences start from exon 27 (shaded) and continue to the poly-A tail. Introns are shown as dashed lines. Splicing of exons B, C, and D result in frame shifts and premature stop codons. Methionine at amino acid 1652 is bolded to indicate the site of introduction of a stop codon in a gene-targeted mouse created in Shang et al. "Human Heart Failure Is Associated With Abnormal C-Terminal Splicing Variants in the Cardiac Sodium Channel" Circulation Research, 2007; 101:1146-1154, the entire content of which is incorporated herein by reference.

One subject has undergone PET scanning at time of blood draw per the specified protocol in Example 2. Increased RV (and left ventricular) uptake is demonstrated, as has previously been described (FIG. 8). Isolation of PBMC from whole blood was performed to confirm adequate cell count for respirometry profiling (BioEnergetics LLC, Boston, Mass.) (FIG. 9).

These data show that the determination of alternative splicing of SCN5A measured by a point-of-care assay reveals a RV PAH phenotype and the risk of SCD in PAH.

Example 2: Alternative Splicing of the Cardiac Sodium Channel and the RV Phenotype in Pulmonary Arterial Hypertension The role of SF and SV in RV failure or SCD has not been studied in PAH. This study quantifies relative expression of circulating SF and SV in PAH patients compared with controls, measures up-stream (HIF1α and Ang II) and down-stream (mitochondrial function) regulators, and correlates expression changes with metabolic changes in the RV longitudinally. In addition, this is the first study in PAH to track mitochondrial bioenergetics from peripheral blood, and among the first studies to look at novel RV biomarkers detected with a point-of-care assay. The prophetic experiments in this Example provide new data about mechanisms that drive RV phenotype in PAH, an area where there are considerable knowledge gaps, and identifying a blood test for risk stratification in PAH. Finally, the study of alternative splicing identifies a molecular target for the advancement of precision medicine in pulmonary vascular disease.

A prospective case-control study is performed to compare whole blood SV messenger ribonucleic acid (mRNA) levels in incident (treatment naïve) WHO Nice Group I PAH patients to SV levels in healthy control subjects matched by age and sex. Upstream triggers of alternative splicing (HIF-1α and Ang II expression levels) and downstream metabolic effects (mitochondrial respiration profile of peripheral blood mononuclear cells (Seahorse Biosciences, North Billerica, Mass., USA) and RV glycolytic shift as measured by 2-deoxy-2[18F]flouro-D-glucose positron emission tomography (FDG-PET)) are assessed. In PAH patients, longitudinal changes in SV mRNA levels and these markers are measured after 3 months of PAH therapy.

Additionally, SV levels track with HIF-1α and Ang II expression levels. The mitochondrial respiration analysis demonstrates increased glycolysis along with increased uptake in the RV on FDG-PET at baseline in PAH patients, and that there is a correlation between levels of SV and metabolic markers.

Figure 2:
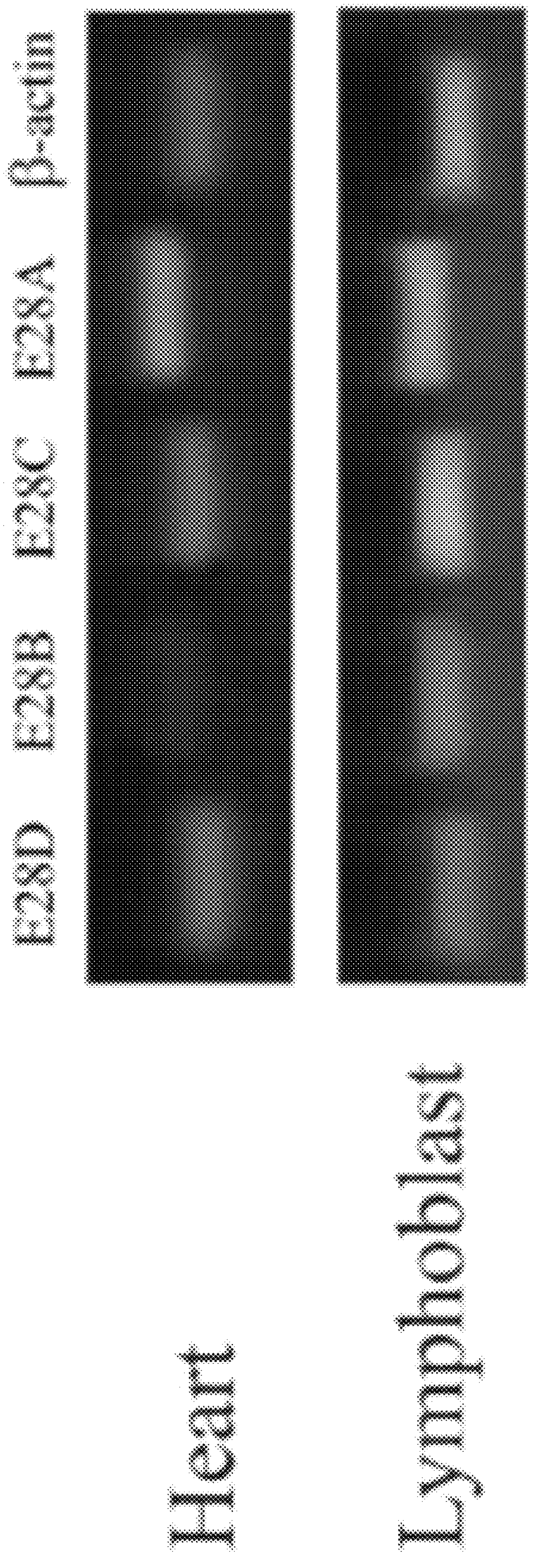
FIG. 2 is a set of pictures of electrophoretic gels showing the presence of splice variants in circulating WBC.
Figure 3:
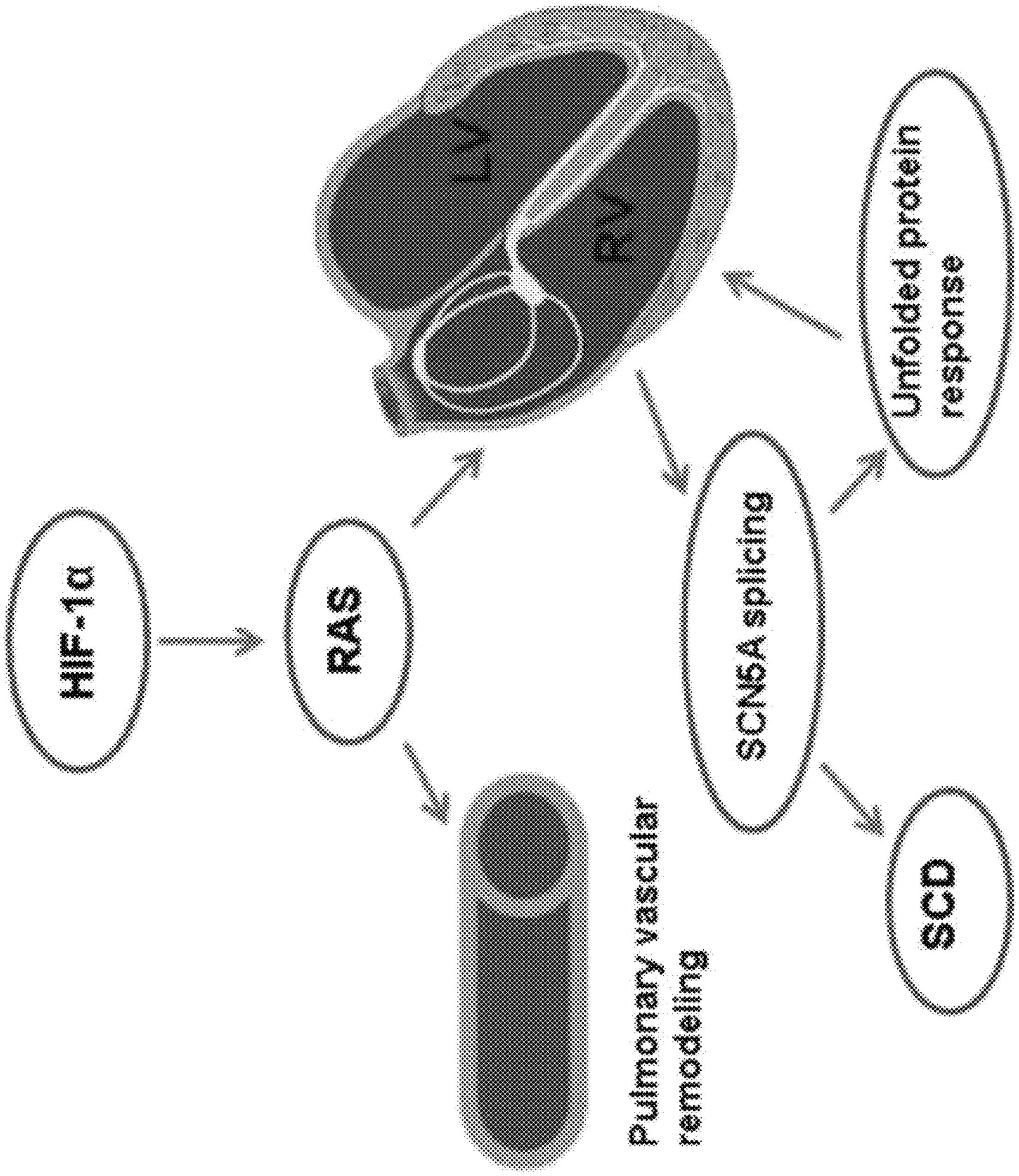
FIG. 3 is a diagram showing a relationship of alternative splicing to pulmonary vascular disease and RV phenotype. LV=left ventricle; RV=right ventricle.

This research improves risk stratification and outcomes in PAH. Alternative splicing of SCN5A is determined to be a unique determinant of RV phenotype in pulmonary vascular disease. Without wishing to be bound by any scientific theory, alternative splicing of SCN5A contributes to RV metabolic changes in PAH, and underpins arrhythmogenesis and SCD (FIG. 1).

SCN5A Expression Levels and PH

SCN5A SV expression levels are determined to be higher in incident PAH cases as compared to age- and sex-matched controls and whether SV expression levels change with PAH therapy. PAH patients have higher SV levels at baseline as compared to controls and SV levels decrease with PAH therapy in PAH patients at three months.

SCN5A SV expression levels are determined to correlate with HIF-1α and Ang II expression levels in whole blood. HIF-1α and Ang II induce SV expression and that SV levels will track with these measurements at baseline in all subjects and at three-month follow-up in PAH patients.

SCN5A SV expression is determined to be associated with markers of the UPR as determined by the mitochondrial respiration profile in circulating peripheral blood mononuclear cells (PBMCs) and glycolytic shift in the RV of PAH patients on FDG-PET. Higher SV levels are associated with lower basal and maximal mitochondrial respiration rates and higher extracellular acidification rates in PAH patients compared to controls at baseline, and the mitochondrial oxygen consumption rate (OCR) increases with PAH therapy in PAH patients at three months. PAH patients have increased FDG uptake in the RV at baseline as compared with FDG uptake after three months of PAH therapy. Further, FDG uptake correlates with mitochondrial OCR.

These data reveal a mechanism that drives RV phenotype and SCD in PAH. This work identifies a simple blood test for risk stratification in PAH as well as targets for molecular therapy to advance precision medicine in this devastating disease.

This is a case-control study of WHO Group I PAH patients and sex- and age-(within 5 years) matched healthy controls. Whole blood is drawn to assess SCN5A SV mRNA levels (normalized to full transcript SCN5A levels) and HIF-1α and Ang II mRNA levels (normalized to (3 actin) at the time of enrollment (in cases and controls) and after three months of PAH therapy (in cases only) (Table 2). Mitochondrial bioenergetics (OCR including basal respiration, maximal respiration, proton leak and non-mitochondrial respiration) are performed by BioEnergetics, LLC Boston, Mass. after PBMC isolation at baseline (in cases and controls) and again after three months of PAH therapy (in cases only). FDG-PET scans for RV tracer uptake are also performed within 2 weeks of blood draw at baseline and at three months in PAH patients.

TABLE 2

Study Overview

| | Study Measures | Cases (n = 5-10) | Controls (n = 10) | Cases, 3 mos PAH Rx |
|---|---|---|---|---|
| Part 1 | SCN5A, SF: RBM25, LUC7L3, SV: E28C and E28D | X | X | X |
| Part 2 | HIF-1α, Ang II | X | X | X |
| Part 3 | Seahorse Analysis | X | X | X |
| | RV uptake (FDG-PET) | X | | X |

Subjects

Cases are recruited according to the criteria set forth below. See Table 5 for inclusion and exclusion criteria. Certain PAH-sub types (e.g., congenital heart disease, PAH related to human immunodeficiency virus) are intentionally excluded given potential for confounding with left heart disease and circulating abnormal WBCs, respectively.

TABLE 5

Inclusion and Exclusion Criteria

| |
|---|
| Inclusion Criteria |
| Mean PAP ≥25 mmHg at rest, pulmonary capillary wedge pressure or left ventricular end-diastolic pressure ≤15 mmHg, and PVR >3 Wood units |
| Diagnosis of PAH that is 1) idiopathic, 2) heritable or 3) associated with connective tissue disease, porto-pulmonary hypertension, former anorexigen/stimulant use |
| Recent pulmonary function testing, chest tomography, and ventilation/perfusion (V/Q) testing (within 2 years) documenting forced expiratory volume in one second/forced vital capacity ratio ≥70% predicted, total lung capacity ≥70% predicted, absence of parenchymal lung disease, and absence of thromboembolic disease (normal or low probability V/Q scan), respectively. |
| Exclusion Criteria |
| Age <18 years old |
| Active treatment of PAH |
| Immunosuppressive medication use |
| Diabetes |
| Active malignancy |
| Untreated severe obstructive sleep apnea diagnosed by polysomnography |
| Evidence of left-sided valvular disease or systolic dysfunction on echocardiogram (≥ moderate mitral or aortic disease or LV ejection fraction ≤50%) |
| PAH related to human immunodeficiency virus infection, or congenital systemic-to-pulmonary shunt |
| Prisoners |
| Pregnant or breastfeeding |

The control group is screened to confirm the absence of cardiopulmonary symptoms and history of heart or lung disease. A baseline EKG is performed to confirm no abnormalities. Cases and controls are matched on sex and age within 5 years.

Study Protocol

The study protocol is summarized in Table 2. Subjects are given information about diet and fasting prior to PET as well as restrictions on the day of PET scanning. The day of the research visit, subjects have an EKG performed in a research examination room. Demographic and clinical characteristics to be collected are described in Tables 3 and 4.

TABLE 3

Study Variables, Cases and Controls

| |
|---|
| Demographics |
| Sex |
| Age, year |
| Race/ethnicity |
| Anthropomorphics |
| Height, m |
| Weight, kg |
| BMI, kg/m$^2$ |
| Smoking status, pack year |
| Current |
| Former |
| Never |
| Laboratory |
| BNP, pg/ml |
| WBC, cells/ml$^3$ |
| EKG |
| Arrhythmia (classify) |
| QTC, ms |
| Medical History |
| Medication list |
| Allergies |
| Problem list |

WBC = white blood cell,

BMI = body mass index;

BNP = beta natriuretic peptide;

EKG = electrocardiogram;

QTc = QT corrected interval

TABLE 4

Study Variables, Cases Only

| |
|---|
| PAH diagnosis |
| Subtype |
| Medication |
| PDE5i |
| ERA |
| Prostacyclin analogue, type |
| sGC stimulator |
| Calcium channel blocker |
| Functional domains |
| 6MWD, m |
| Functional class |
| Hemodynamic parameters |
| RAP, mmHg |
| mPAP, mmHg |
| PCWP, mmHg |
| CO, L/min |
| PVR, Wood units |

TABLE 4-continued

| Study Variables, Cases Only |
| --- |
| Echocardiography parameters |
| RV size and function grading |
| RA size grading |
| TAPSE, mm |
| RVSP, mmHg |

PDE5i = phosphodiesterase type five inhibitor;
ERA = endothelin receptor antagonist;
sGC = soluble guanylyl cyclase;
6MWD = Six-minute walk distance;
FC = functional class;
RAP = right atrial pressure;
mPAP = mean pulmonary artery pressure;
PCWP = pulmonary capillary wedge pressure;
CO = cardiac output;
PVR = pulmonary vascular resistance;
RA = right atrial;
TAPSE = tricuspid annular plane systolic excursion;
RVSP = RV systolic pressure Approximately 25 cc of blood are drawn from each subject for: 1) a complete blood count and brain natriuretic peptide level (lavender top tube), 2) two PAXgene tubes (for RNA isolation) and 3) a Cell Preparation Tube (for PBMC isolation). Cases receive PET scanning either before or after blood draw. Subjects receive intravenous placement and tracer (2-deoxy-2[18F]flouro-D-glucose) administration and after 90 minutes the subjects undergo PET scanning PBMCs are isolated within 2 hours of blood draw and PAXgene tubes are stored at room temperature before freezing at −80° C. for RNA extraction. This process is repeated after 3 months for all cases.

Determination of Expression Levels

SCN5A SV expression levels are determined to be increased in incident PAH cases as compared to age- and sex-matched controls. Additionally, SV expression levels change with PAH therapy. Whole blood mRNA expression levels are compared between cases and controls for the following targets: SCN5A, SF and their SV E28C and E28D. Standardized procedures for RNA extraction and qPCR from whole blood are performed using the PAXgene Blood RNA Kit (Qiagen, Valencia, Calif.). Concentrations and purity of RNA isolate are quantified with (NanoDrop8000, Thermo Scientific, Carlsbad, Calif.). All samples are normalized to absolute values of β-actin. Fold changes for SV are normalized to total SCN5A transcripts. The intra-assay coefficient of variation for RBM25 is <1%, demonstrating excellent precision. In subjects afflicted with PAH, SV and SF expression levels are repeated 3 months after the initiation of PAH therapy.

SCN5A SV expression levels are determined to correlate with HIF-1α and Ang II expression levels in whole blood. RNA extraction for the measurement of HIF-1α and Ang II is performed as above.

SCN5A SV expression is determined to be associated with markers of the UPR as determined by the mitochondrial respiration profile in circulating PBMCs and glycolytic shift in the RV on FDG-PET. The XF24 Analyzer (Seahorse Biosciences, North Billerica, Mass., USA) is used to measure the OCR from PBMC isolated from whole blood using standardized procedures. PBMCs are stored immediately in freezing media and placed in a −80° C. freezer. Cryovials are then transferred on dry ice for storage in liquid nitrogen and shipped to (e.g., BioEnergetics LLC (Boston, Mass.)) for Seahorse analysis within 3 months. Briefly, the optimum concentration of the inhibitors and activators is determined for OCR (Chacko et al., Lab Invest. 2013; 93(6):690-700). Mean basal respiration is quantified by obtaining OCR measurements prior to the addition of the inhibitors or activators. ATP-linked OCR and proton leak is determined by injecting oligomycin at 0.5 μM followed by 0.6 μM FCCP, an uncoupler of the electron transport chain, which decides the maximal respiration rate and spare capacity (Chacko et al., Lab Invest. 2013; 93(6):690-700). Quality control data from Bioenergetics LLC shows minimal intra-plate variability between samples and over time during repeat testing.

SCN5A SV expression is determined to be associated with glycolytic shift in the RV on FDG-PET. Only PAH cases (defined below) are included in this portion of the Study. Fasting FDG-PET is performed as has been previously described for PAH (Lundgrin et al., Ann Am Thorac Soc. 2013; 10(1):1-9; Oikawa et al., J Am Coll Cardiol. 2005; 45(11):1849-55). After a six-hour fast, subjects 370 MBq (10 mCi) of FDG glucose tracer injected followed by sequential hybrid PET/CT 90 minutes later. FDG uptake is measured in all four chambers of the heart and normalized to FDG of blood pool in the thoracic aorta using the published calculation: average FDG-SUV in region of interest/average FDG-SUV in blood pool of the thoracic aorta (Lundgrin et al., Ann Am Thorac Soc. 2013; 10(1):1-9). Uptake in the pulmonary circulation is also be compared and assessed over time in cases.

Sample Size and Power Analysis 5-10 incident (treatment naïve) PAH patients are enrolled to be age- and sex-matched 1:1 with controls for this study. Including 2-3 matched pairs would provide a 80% power to detect a 1.0 fold difference in RBM25 mRNA levels and a 0.5-fold difference in LUC7L3 mRNA, as is seen in systolic heart failure patients versus normal controls (α=0.05) (FIG. 6) (Gao et al., Circulation. 2011; 124(10):1124-31).

Statistical Analyses

Continuous data is expressed using median (interquartile range). Categorical variables are reported as frequency and percentages.

Case status is regressed on SV (and HIF-1α and Ang II) expression levels using generalized estimating equations assuming a binary distribution. Classical sandwich estimation is used to adjust for model misspecification after maximizing the appropriateness of distribution selected. No adjustment for multiple comparisons is made. The relationships between SV and markers of disease severity (functional class, 6MWD, and hemodynamics) in cases are examined with multivariable linear or binomial regression as appropriate. A generalized linear model for repeated measures is used and mitochondrial respiration profile. Comparisons of FDG uptake at 3 months are reported as percent change from baseline and analyzed by paired t tests or non-parametric equivalent. Spearman's rho is used to assess for correlations between bioassays and clinical parameters with FDG-PET uptake. Results are tested using two-tailed tests. P values<0.05 are considered significant. All analyses are conducted using SAS Software 9.4 (SAS Inc., Cary, N.C.).

PAH patients show higher mRNA expression levels of SV and SF with concurrent decreased expression of total mRNA transcripts of SCN5A, higher levels of HIF-1α and Ang II expression as compared to controls, and that all molecular signatures are increased at baseline as compared to follow-up once treated in PAH patients. Mitochondrial respiration is significantly altered (with a shifted glycolytic pathway) in PAH patients compared with controls and is reflected by increased RV uptake on FUG-PET in PAH cases. This uptake correlates with circulating SV and SF expression levels.

WBC are used to measure SCN5A transcript and/or protein/peptide levels. Assays include the evaluation of patients with pulmonary hypertension (PH) related to heart failure with preserved ejection fraction, an extremely common phenotype, in whom PH/RV failure is poorly characterized/understood but is an independent risk factor for death. The present subject matter provides valuable new methods and compositions for diagnosing and evaluating risks associated with PH, as well as for stratifying subjects afflicted with PH.

OTHER EMBODIMENTS

While the invention has been described in conjunction with the detailed description thereof, the foregoing description is intended to illustrate and not limit the scope of the disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank, NCBI, UniProt, or other submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the disclosure encompassed by the appended claims.

What is claimed is:

1. A method for diagnosing pulmonary hypertension (PH) or a risk of developing PH in a subject comprising
(a) providing a test sample from said subject, wherein said test sample comprises a circulating cell of whole blood;
(b) assaying the level of a full-length SCN5A protein-encoding mRNA or a SCN5A splice variant protein-encoding mRNA in the test sample; and
(c) diagnosing the subject with PH or a risk of developing PH if (i) the level of the full-length SCN5A protein-encoding mRNA is reduced in the subject compared to a normal control, or (ii) the level of the mRNA encoding the SCN5A splice variant is increased by at least 4-fold compared to a normal control.

2. The method of claim 1, wherein (i) the level of the full-length SCN5A protein-encoding mRNA is reduced in the subject compared to a normal control, or (ii) the level of mRNA encoding the SCN5A splice variant is increased compared to a normal control indicates a diagnosis of PH.

3. A method for identifying whether a subject afflicted with PH is at risk of dying from sudden cardiac death (SCD), comprising
(a) providing a test sample from said subject, wherein said test sample comprises whole blood;
(b) assaying the level of a full-length SCN5A protein-encoding mRNA or a SCN5A splice variant protein-encoding mRNA in the test sample; and
(c) (1) comparing the level determined in (b) to a value in a database to identify the subject's absolute or relative risk of suffering from SCD, or (2) identifying the subject is at risk of suffering from SCD if the level of the SCN5A splice variant protein-encoding mRNA is at least about 4-fold greater in the subject compared to a normal control.

4. The method of claim 3, wherein the database contains
(a) level values of full-length SCN5A protein-encoding mRNA or SCN5A splice variant protein-encoding mRNA from (i) subjects who have suffered from SCD, (ii) subjects who are afflicted with PH but who have not suffered from SCD, (iii) subjects afflicted with PH for at least about 1, 2, 3, 4, 5, 10, 15, or 20 years without suffering from SCD, and/or (iv) subjects who are not afflicted with PH, and/or
(b) mean or median level values calculated using full-length SCN5A protein-encoding mRNA or SCN5A splice variant protein-encoding mRNA level values from (i) subjects who have suffered from SCN5A, (ii) subjects who are afflicted with PH but who have not suffered from SCD, (iii) subjects afflicted with PH for at least about 1, 2, 3, 4, 5, 10, 15, or 20 years without suffering from SCD, and/or (iv) subjects who are not afflicted with PH.

5. The method of claim 3, further comprising administering a treatment to the subject if the subject is identified as being at risk of suffering from SCD.

6. The method of claim 3, further comprising directing the subject to obtain additional screening for SCD risk based on the level of the full-length SCN5A protein-encoding mRNA or SCN5A splice variant protein-encoding mRNA in the test sample.

7. A method of SCD treatment, comprising identifying a subject at risk of suffering from SCD according to the method of claim 3, and administering to the subject a treatment for SCD.

8. The method of claim 7, wherein the treatment for SCD comprises administration of an antiarrhythmic drug, an angiotensin converting enzyme inhibitor (ACE), an angiotensin II receptor blocker, a beta-blocker, digoxin, a diuretic, a blood vessel dilator, an aldactone inhibitor, or a calcium channel blocker to the subject.

9. The method of claim 7, wherein the treatment for SCD comprises implantation of a cardioverter-defibrillator (ICD) or surgery to repair or replace a mitral valve or an aortic valve in the subject.

10. The method of claim 1, wherein the PH is pulmonary arterial hypertension (PAH).

11. The method of claim 1, wherein the SCN5A splice variant is E28B, E28C and/or E28D, or wherein the SCN5A splice variant is two or more splice variants, and the two or more splice variants comprise one or more of E28B, E28C, and E28D.

12. The method of claim 1, further comprising
(a) determining the level of one or more of HIF-1α, AngII, LUC7L3, RBM25, and/or PERK in the test sample;
(b) assaying whether the subject comprises mitochondrial aerobic glycolysis; or
(c) assaying whether the subject comprises mitochondrial aerobic glycolysis, wherein said assaying comprises 2-deoxy-2($^{18}$F)flouro-D-glucose positron emission tomography (FDG-PET).

13. The method of claim 1, wherein assaying the level of the full-length SCN5A protein-encoding mRNA or the SCN5A splice variant protein-encoding mRNA comprises contacting the full-length SCN5A protein-encoding mRNA or the SCN5A splice variant protein-encoding mRNA with a SCN5A-specific binding agent.

14. The method of claim 13, wherein the binding agent comprises an antibody or a fragment thereof, a detectable protein or a fragment thereof, or a nucleic acid molecule.

15. The method of claim 14, wherein
(a) the nucleic acid molecule comprises at least one probe or at least one primer;
(b) the assaying comprises a polymerase chain reaction (PCR), reverse transcription polymerase chain reaction (RT-PCR), quantitative PCR (qPCR), or a Northern Blot;
(c) assaying the level of the full-length SCN5A protein-encoding mRNA or the SCN5A splice variant protein-encoding mRNA comprises reverse-transcribing cDNA from the full-length SCN5A protein-encoding mRNA or the SCN5A splice variant protein-encoding mRNA;
(d) the binding agent comprises an antibody;
(e) the binding agent comprises an antibody wherein the antibody comprises an anti-full-length SCN5A and/or an anti-SCN5A splice variant antibody;
(f) the binding agent comprises an antibody, wherein the antibody comprises conjugated to a detectable moiety;
(g) the binding agent comprises an antibody wherein said antibody comprises a polyclonal antibody or a monoclonal antibody;
(h) wherein said binding agent is attached to a solid support;
(i) wherein said binding agent is attached to a solid support, wherein said solid support comprises a strip, a multiwell plate, a microarray, a polymer, a bead, or a nanoparticle;
(j) wherein the binding agent comprises a detectable moiety, and the detectable moiety comprises a fluorescent marker, a radioactive isotope, or a chemiluminescent compound;
(k) wherein the binding agent comprises a detectable moiety, and the detectable moiety comprises a fluorescent marker, a radioactive isotope, or a chemiluminescent compound, wherein the detectable moiety comprises a fluorescent marker, and the fluorescent marker comprises fluorescein isothiocyanate, rhodamine, phycoerythrin, phycocyanin, allophycocyanin, p-phthaldehyde and fluorescamine, or $^{152}$Eu;

(l) wherein the binding agent comprises a detectable moiety, and the detectable moiety comprises a fluorescent marker, a radioactive isotope, or a chemiluminescent compound, wherein the detectable moiety comprises a radioactive isotope, and the radioactive isotope is $^{125}$iodine, tritium, $^{75}$selenomethonine, or $^{64}$copper; or (m) wherein the binding agent comprises a detectable moiety, and the detectable moiety comprises a fluorescent marker, a radioactive isotope, or a chemiluminescent compound, wherein the detectable moiety comprises a chemiluminescent compound, and the chemiluminescent compound is luminol, isoluminol, theromatic acridinium ester, imidazole, acridinium salt, or oxalate ester.

* * * * *

SEQUENCE LISTING

```
<160> NUMBER OF SEQ ID NOS: 21

<210> SEQ ID NO 1
<211> LENGTH: 4303
<212> TYPE: DNA
<213> ORGANISM: Artificial Sequence
<220> FEATURE:
<223> OTHER INFORMATION: cDNA Sequence for RBM25

<400> SEQUENCE: 1

agtgcacgcc gggcaagagg aagacctcca tcagctcgcc gcgcagcgcg gctgtatttg      60

cggcctgtgc gagtaggcgc ttgggcactc agtctccctg gcgagcgacg ggcagaaatc     120

tcgaaccagt ggagcgcact cgtaacctgg atcccagaag gtcgcgaagg cagtaccgtt     180

tcctcagcgg cggactgctg cagtaagaat gtcttttcca cctcatttga atcgccctcc     240

catgggaatc ccagcactcc caccagggat cccacccccg cagtttccag gatttcctcc     300

acctgtacct ccagggaccc caatgattcc tgtaccaatg agcattatgg ctcctgctcc     360

aactgtctta gtacccactg tgtctatggt tggaaagcat ttgggcgcaa gaaaggatca     420

tccaggctta aaggctaaag aaaatgatga aaattgtggt cctactacca ctgtttttgt     480

tggcaacatt tccgagaaag cttcagacat gcttataaga caactcttag ctaaatgtgg     540

tttggttttg agctggaaga gagtacaagg tgcttccgga aagcttcaag ccttcggatt     600

ctgtgagtac aaggagccag aatctaccct ccgtgcactc agattattac atgacctgca     660

aattggagag aaaaagctac tcgttaaagt tgatgcaaag acaaaggcac agctggatga     720

atggaaagca aagaagaaag cttctaatgg gaatgcaagg ccagaaactg tcactaatga     780

cgatgaagaa gccttggatg aagaaacaaa gaggagagat cagatgatta aaggggctat     840

tgaagtttta attcgtgaat actccagtga gctaaatgcc ccctcacagg aatctgattc     900

tcaccccagg aagaagaaga aggaaaagaa ggaggacatt ttccgcagat ttccagtggc     960

cccactgatc ccttatccac tcatcactaa ggaggatata aatgctatag aaatggaaga    1020

agacaaaaga gacctgatat ctcgagagat cagcaaattc agagacacac ataagaaact    1080

ggaagaagag aaaggcaaaa aggaaaaaga aagacaggaa attgagaaag aacggagaga    1140

aagagagagg gagcgtgaaa gggaacgaga aaggcgagaa cgggaacgag aaagggaaag    1200

agaacgtgaa cgagaaaagg agaaagaacg ggagcgggaa cgagaacggg atagggaccg    1260
```

tgaccggaca aaagagagag accgagatcg ggatcgagag agagatcgtg accgggatag 1320
agaaaggagc tcagatcgta ataaggatcg cagtcgatca agagaaaaaa gcagagatcg 1380
tgaaagggaa cgagagcggg aaagagagag agagagagaa cgagagcgag aacgagaacg 1440
ggagcgagag agagagcgag agagggaacg ggagcgagaa agagaaaaag acaaaaaacg 1500
ggaccgagaa gaagatgaag aagatgcata cgaacgaaga aaacttgaaa gaaaactccg 1560
agagaaagaa gctgcttatc aagagcgcct taagaattgg gaaatcagag aacgaaagaa 1620
aacccgggaa tatgagaaag aagctgaaag agaagaagaa agaagaagag aaatggccaa 1680
agaagctaaa cgactaaaag aattcttaga agactatgat gatgatagag atgaccccaa 1740
atattacaga ggaagtgctc ttcagaaaag gttgcgtgat agagaaaagg aaatggaagc 1800
agatgaacga gataggaaga gagagaagga ggagcttgag gaaatcaggc agcgccttct 1860
ggcagaaggg catccagatc cagatgcaga gctccagagg atggaacaag aggctgagag 1920
gcgcaggcag ccacaaataa agcaagagcc agaatcagaa gaggaggaag aagaaaagca 1980
agaaaaagaa gaaaaacgag aagaacccat ggaagaggaa gaggagccag agcaaaagcc 2040
ttgtctgaaa cctactctga ggcccatcag ctctgctcca tctgtttcct ctgccagtgg 2100
caatgcaaca cctaacactc ctggggatga gtctccctgt ggtattatta ttcctcatga 2160
aaactcacca gatcaacagc aacctgagga gcataggcca aaaataggac taagtcttaa 2220
actgggtgct tccaatagtc ctggtcagcc taattctgtg aagagaaaga aactacctgt 2280
agatagtgtc tttaacaaat ttgaggatga agacagtgat gacgtacccc gaaaaaggaa 2340
actggttccc ttggattatg gtgaagatga taaaaatgca accaaaggca ctgtaaacac 2400
tgaagaaaag cgtaaacaca ttaagagtct cattgagaaa atccctacag ccaaacctga 2460
gctcttcgct tatcccctgg attggtctat tgtggattct atactgatgg aacgtcgaat 2520
tagaccatgg attaataaga aaatcataga atatataggt gaagaagaag ctacattagt 2580
tgattttgtt tgttctaagg ttatggctca tagttcaccc cagagcattt tagatgatgt 2640
tgccatggta cttgatgaag aagcagaagt tttatatagtc aaaatgtgga gattattgat 2700
atatgaaaca gaagccaaga aaattggtct tgtgaagtaa aactttttat atttagagtt 2760
ccatttcaga tttcttcttt gccacccttt taaggacttt gaatttttct ttgtctttga 2820
agacattgtg agatctgtaa tttttttttt ttgtagaaaa tgtgaatttt ttggtcctct 2880
aatttgttgt tgccctgtgt actcccttgg ttgtaaagtc atctgaatcc ttggttctct 2940
ttatactcac caggtacaaa ttactggtat gttttataag ccgcagctac tgtacacagc 3000
ctatctgata taatcttgtt ctgctgattt gtttcttgta aatattaaaa cgactcccca 3060
attattttgc agaattgcac ttaatattga aatgtactgt ataggaacca acatgaacaa 3120
ttttaattga aaacaccagt cataaactat taccaccccc actctctttt gatcagaaat 3180
ggcaagccct tgtgaaggca tggagtttaa aattggaatg caaaaattag cagacaatcc 3240
attcctactg tatttctgta tgaatgtgtt tgtgaatgta tgtgtaaaag tctttctttt 3300
ccctaatttg ctttggtggg gtccttaaaa catttcccaa ctaaagaata gaattgtaaa 3360
ggaaaagtgg tactgttcca acctgaaatg tctgttataa ttaggttatt agtttcccag 3420
agcatggtgt tctcgtgtcg tgagcaatgt ggtttgctaa ctggatgggg ttttcttatt 3480
aataagatgg ctgcttcagc ttctctttta aaggaatgtg gatcatagtg atttttcctt 3540
ttaattttat tgctcagaaa tgaggcatat cctaaaaatc ctggagagct gtatttaatg 3600

```
catttttgca ctaattggtc cttagtttaa ttctattgta tctgtttatt taacaaaaaa   3660

ttcatcatac caaaaagtgt aagtgaaaac cccctttaaa acaaaacaaa aaaatgaaat   3720

aaaattaggc aaattgacag acagtgagag ttttacaaac atgataggta ttctgctcgg   3780

caatttgtaa gtttacatgt tatttaagga taaaggtaaa tcattcaagg cagttaccaa   3840

ccactaacta tttgttttca tttttgtctt gtagaaggtt tatatcttgt tttaccttgg   3900

ctcattagtg tttaaaaatg tactgatgat gtgcttagag aaattcctgg ggctttcttc   3960

gttgtagatc agaatttcac cagggagtaa aattacctga aaacgtaaga agttttaaac   4020

agcttttcac acaaattaga tgcaactgtt cccatgtctg agtacttatt taaaagaaag   4080

gtaaagattg gcctgttaga aaaagcataa tgtgagcttt ggattactgg attttttttt   4140

tttttaaaca cacctggaga ggacatttga aaacactgtt cttaccctcg aaccctgatg   4200

tggttccatt atgtaaatat ttcaaatatt aaaaatgtat atatttgatc ctggggactc   4260

atattctttc agaatcatgt aaataaatgg catcatgttg taa                     4303
```

<210> SEQ ID NO 2
<211> LENGTH: 3525
<212> TYPE: DNA
<213> ORGANISM: Artificial Sequence
<220> FEATURE:
<223> OTHER INFORMATION: cDNA Sequence for LUC7L3

<400> SEQUENCE: 2

```
acggcatgct gggaaggcgt ccgcgcggcg gccattttgt cttgtcggct cctgtgtgta     60

ggagggattt cggcctgaga gcgggccgag gagattggcg acggtgtcgc ccgtgttttc    120

gttggcgggt gcctgggctg gtgggaacag ccgcccgaag gaagcaccat gatttcggcc    180

gcgcagttgt tggatgagtt aatgggccgg gaccgaaacc tagccccgga cgagaagcgc    240

agcaacgtgc ggtgggacca cgagagcgtt tgtaaatatt atctctgtgg tttttgtcct    300

gcggaattgt tcacaaatac acgttctgat cttggtccgt gtgaaaaaat tcatgatgaa    360

aatctacgaa aacagtatga gaagagctct cgtttcatga aagttggcta tgagagagat    420

tttttgcgat acttacagag cttacttgca gaagtagaac gtaggatcag acgaggccat    480

gctcgtttgg cattatctca aaaccagcag tcttctgggg ccgctggccc aacaggcaaa    540

aatgaagaaa aaattcaggt tctaacagac aaaattgatg tacttctgca acagattgaa    600

gaattagggt ctgaaggaaa agtagaagaa gcccagggga tgatgaaatt agttgagcaa    660

ttaaaagaag agagagaact gctaaggtcc acaacgtcga caattgaaag ctttgctgca    720

caagaaaaac aaatggaagt ttgtgaagta tgtggagcct ttttaatagt aggagatgcc    780

cagtcccggg tagatgacca tttgatggga aaacaacaca tgggctatgc caaaattaaa    840

gctactgtag aagaattaaa agaaaagtta aggaaaagaa ccgaagaacc tgatcgtgat    900

gagcgtctaa aaaaggagaa gcaagaaaga gaagaaagag aaaaagaacg ggagagagaa    960

agggaagaaa gagaaaggaa aagacgaagg gaagaggaag aaagagaaaa agaaaagggct   1020

cgtgacagag aaagaagaaa gagaagtcgt tcacgaagta gacactcaag ccgaacatca   1080

gacagaagat gcagcaggtc tcgggaccac aaaaggtcac gaagtagaga aagaaggcgg   1140

agcagaagta gagatcgacg aagaagcaga agccatgatc gatcagaaag aaaacacaga   1200

tctcgaagtc gggatcgaag aagatcaaaa agccgggatc gaaagtcata taagcacagg   1260

agcaaaagtc gggacagaga acaagataga aaatccaagg agaaagaaaa gaggggatct   1320

gatgataaaa aaagtagtgt gaagtccggt agtcgagaaa agcagagtga agacacaaac   1380
```

```
actgaatcga aggaaagtga tactaagaat gaggtcaatg ggaccagtga agacattaaa   1440

tctgaaggtg acactcagtc caattaaaac tgatctgata agacctcaga tcagacagag   1500

gtaagtgtat tgtttctcac tttgattagg gctttttgtt actgtttgac agtgcagcgt   1560

aagtatgcac agatgaagat ggaactaagc cgagtaagaa gacatacaaa agcctcttct   1620

gaaggaaaag acagtgtagt cctgcaaaac attttgaggt acattgtttt gtctcagcta   1680

ttttgtagca gactcgtgcc cccattagtg tgcctctttg gaaattatcg cccacatttg   1740

taatatagtc gccattgaaa agttaattat cctttttta gggattttga tgtcatttct   1800

ttttttttt taataaaaag gttgaactgt ttttttttt ctttttggta ttaagtccat   1860

cttgtgttgg tacattggca gagacatatg ctttaaaaac ttaaatattt cggaggcaca   1920

tgttggacta ctttgtttta attaaactgc tagtatttct ttgtcaagga tgtttctagt   1980

tttttgcttt attgccttgc attctaatgc agtttgttct gtaactcgag agccagtagc   2040

attggattga tggaagtgta gggtttatga attattgcag ctgactacca tacctcacac   2100

agcgttggtg ttgtgagcgg cccatgaaaa gccaaattaa aaatcaagga ttcagtcaaa   2160

ctaagcaggt actcatgcca ggtactcctt tctctaccca catccatgtt tgaatgctat   2220

tgcctgtgat ctttacgctt aactgttgtg tatctttttt gttctttaca agaagtgcag   2280

aggggttttt tgtgtattgc gtgaaaactt ataaaacaaa tgttaacaga atggaatttt   2340

ttttcaactg tatgtagggc tgcagtggtg gccagaatta gatatcttta aagaatttta   2400

aatacaataa acacttcata ttattcgcct tgttacactc aatgcaattc tcaagtctat   2460

aagaggtatg tgcttaatat ttcctactgt gtaggagaat ttgcagtcag ccataggtat   2520

gtaggaatag tcactcactg gctgatacat ttaaagcagc agtgtgaata gcaaggacag   2580

acaccttcaa tttgtgaaat caaagaactg atgcactata tagaacgaat ttgggttttt   2640

aaagaaatat taaaagttag gtactgtaag tgttcttaaa acctgtaaac ttcattctgt   2700

gggctagtgg tgtgggacaa aatattccta atgaaaggaa gtaccaatta gttgatttgt   2760

tggtggcatt cccctttgg gaaagcaatg taaggttatg tctgtgtatg tcattcacac   2820

ttaggcaagc atacacaggc acatggcttt aagaaccaca ctgatgcctt gataattaaa   2880

aagaatacaa gcattccatg tacacatgtt aattagcagt tagtgactgg gccaacactt   2940

tctcataaaa attggccttt tacatgttgt ctaattatca tttttcccca aattttgcgt   3000

tgtaggacta ctgttcgaag atttttggaa gaatactgag aacggcataa agtgaagatc   3060

gacatttaaa aaatgaggtg aaagaaagct atagtggcat agaaaaagta taaagctcag   3120

ttagtttttt tattattatt attattaaaa gttaattcag gactgatgtg acctaccaga   3180

tttcagaaca tgtgttaata gtatatatgc cactgaaaac ttaggtcctg tatcatactt   3240

ttttctttaa gactttttaa gaaatattac ttaaacatgt ggcttgctca gtgtttaatt   3300

gcaagttttc aatcttggac tttgaaaaca ggattaaacg ttagtattcg tgtgaatcag   3360

actaagtggg atttcatttt tacaactctg ctctacttag cctttggatt tagaagtaaa   3420

aataaagtat ctctgacttt ctgttacaaa gttgattgtc tctgtcattg aaaagtttta   3480

gtattaatct ttttctaata aagttattga ctctgaaaaa aaaaa                   3525
```

<210> SEQ ID NO 3
<211> LENGTH: 321
<212> TYPE: DNA
<213> ORGANISM: Artificial Sequence
<220> FEATURE:

-continued

<223> OTHER INFORMATION: cDNA Sequence for Exon 28 of SCN5A splice
variant Exon 28 B (E28B)

<400> SEQUENCE: 3

```
ggagccctcc tagtgagtat gaagtgatat ctcactgagg ttttggtttg caaaagcaaa     60

tgactgatga ctaacgatgc aggacatctt tccatgtgca tgttggtcat ttatatatct    120

tccttggaga aatctctatt cagatcctta gctcattttt aattgggtta tttctcttct    180

tcttgttgag ttgtaagagt tctttacata ttctggatca cagtctctta tcagatatat    240

gatttaaaaa tattttctcc tagtctgtga gttttttcat ttcctagtgg tgtccattaa    300

agcacaaaag ttttacatgt t                                              321
```

<210> SEQ ID NO 4
<211> LENGTH: 164
<212> TYPE: DNA
<213> ORGANISM: Artificial Sequence
<220> FEATURE:
<223> OTHER INFORMATION: cDNA Sequence for Exon 28 of SCN5A splice
variant Exon 28 C (E28C)

<400> SEQUENCE: 4

```
gaactgcaca atgaccagca ggaggggaga agagagtagg aaaaaggagg gaaggacaga     60

catcaagtgc cagatgttgt ctgaactaat cgagcacttc tcaccaaact tcatgtataa    120

ataaaataca tatttttaaa acaaaccaat aaatggctta catg                     164
```

<210> SEQ ID NO 5
<211> LENGTH: 114
<212> TYPE: DNA
<213> ORGANISM: Artificial Sequence
<220> FEATURE:
<223> OTHER INFORMATION: cDNA Sequence for Exon 28 of SCN5A splice
variant Exon 28 D (E28D)

<400> SEQUENCE: 5

```
ggcactgtgc tctcggacat catccagaag tacttcttct ccccgacgct cttccgagtc     60

atccgcctgg cccgaatagg ccgcatcctc agactgatcc gaggggccaa gggg          114
```

<210> SEQ ID NO 6
<211> LENGTH: 5327
<212> TYPE: DNA
<213> ORGANISM: Artificial Sequence
<220> FEATURE:
<223> OTHER INFORMATION: E28B SCN5A Splice Variant Complete Nucleotide
Sequence

<400> SEQUENCE: 6

```
agacggcggc ggcgcccgta ggatgcaggg atcgctcccc cggggccgct gagcctgcgc     60

ccagtgcccc gagccccgcg ccgagccgag tccgcgccaa gcagcagccg cccaccccgg    120

ggcccggccg ggggaccagc agcttcccca caggcaacgt gaggagagcc tgtgcccaga    180

agcaggatga gaagatggca aacttcctat tacctcgggg caccagcagc ttccgcaggt    240

tcacacggga gtccctggca gccatcgaga agcgcatggc agagaagcaa gcccgcggct    300

caaccacctt gcaggagagc cgagaggggc tgcccgagga ggaggctccc cggccccagc    360

tggacctgca ggcctccaaa aagctgccag atctctatgg caatccaccc caagagctca    420

tcggagagcc cctggaggac ctggacccct tctatagcac ccaaaagact ttcatcgtac    480

tgaataaagg caagaccatc ttccggttca gtgccaccaa cgccttgtat gtcctcagtc    540

ccttccaccc catccggaga gcggctgtga agattctggt tcactcgctc ttcaacatgc    600
```

-continued

```
tcatcatgtg caccatcctc accaactgcg tgttcatggc ccagcacgac cctccaccct    660
ggaccaagta tgtcgagtac accttcaccg ccatttacac ctttgagtct ctggtcaaga    720
ttctggctcg aggcttctgc ctgcacgcgt tcactttcct tcgggaccca tggaactggc    780
tggactttag tgtgattatc atggcataca caactgaatt tgtggacctg ggcaatgtct    840
cagccttacg caccttccga gtcctccggg ccctgaaaac tatatcagtc atttcagggc    900
tgaagaccat cgtgggggcc ctgatccagt ctgtgaagaa gctggctgat gtgatggtcc    960
tcacagtctt ctgcctcagc gtctttgccc tcatcggcct gcagctcttc atgggcaacc   1020
taaggcacaa gtgcgtgcgc aacttcacag cgctcaacgg caccaacggc tccgtggagg   1080
ccgacggctt ggtctgggaa tccctggacc tttacctcag tgatccagaa aattacctgc   1140
tcaagaacgg cacctctgat gtgttactgt gtgggaacag ctctgacgct gggacatgtc   1200
cggagggcta ccggtgccta aaggcaggcg agaaccccga ccacggctac accagcttcg   1260
attcctttgc ctgggccttt cttgcactct tccgcctgat gacgcaggac tgctgggagc   1320
gcctctatca gcagaccctc aggtccgcag ggaagatcta catgatcttc ttcatgcttg   1380
tcatcttcct ggggtccttc tacctggtga acctgatcct ggccgtggtc gcaatggcct   1440
atgaggagca aaaccaagcc accatcgctg agaccgagga gaaggaaaag cgcttccagg   1500
aggccatgga aatgctcaag aaagaacacg aggccctcac catcaggggt gtggataccg   1560
tgtcccgtag ctccttggag atgtcccctt tggccccagt aaacagccat gagagaagaa   1620
gcaagaggag aaaacggatg tcttcaggaa ctgaggagtg tggggaggac aggctcccca   1680
agtctgactc agaagatggt cccagagcaa tgaatcatct cagcctcacc cgtggcctca   1740
gcaggacttc tatgaagcca cgttccagcc gcgggagcat tttcaccttt cgcaggcgag   1800
acctgggttc tgaagcagat tttgcagatg atgaaaacag cacagcgggg gagagcgaga   1860
gccaccacac atcactgctg gtgccctggc ccctgcgccg gaccagtgcc cagggacagc   1920
ccagtcccgg aacctcggct cctggccacg ccctccatgg caaaaagaac agcactgtgg   1980
actgcaatgg ggtggtctca ttactggggg caggcgaccc agaggccaca tccccaggaa   2040
gccacctcct ccgccctgtg atgctagagc acccgccaga cacgaccacg ccatcggagg   2100
agccaggcgg gccccagatg ctgacctccc aggctccgtg tgtagatggc ttcgaggagc   2160
caggagcacg gcagcgggcc ctcagcgcag tcagcgtcct caccagcgca ctggaagagt   2220
tagaggagtc tcgccacaag tgtccaccat gctggaaccg tctcgcccag cgctacctga   2280
tctgggagtg ctgcccgctg tggatgtcca tcaagcaggg agtgaagttg gtggtcatgg   2340
acccgtttac tgacctcacc atcactatgt gcatcgtact caacacactc ttcatggcgc   2400
tggagcacta caacatgaca agtgaattcg aggagatgct gcaggtcgga aacctggtct   2460
tcacagggat tttcacagca gagatgacct tcaagatcat tgccctcgac ccctactact   2520
acttccaaca gggctggaac atcttcgaca gcatcatcgt catccttagc ctcatggagc   2580
tgggcctgtc ccgcatgagc aacttgtcgg tgctgcgctc cttccgcctg ctgcgggtct   2640
tcaagctggc caaatcatgg cccaccctga acacactcat caagatcatc gggaactcag   2700
tgggggcact ggggaacctg acactggtgc tagccatcat cgtgttcatc tttgctgtgg   2760
tgggcatgca gctctttggc aagaactact cggagctgag ggacagcgac tcaggcctgc   2820
tgcctcgctg gcacatgatg gacttctttc atgccttcct catcatcttc cgcatcctct   2880
gtggagagtg gatcgagacc atgtgggact gcatggaggt gtcggggcag tcattatgcc   2940
```

-continued

```
tgctggtctt cttgcttgtt atggtcattg gcaaccttgt ggtcctgaat ctcttcctgg   3000
ccttgctgct cagctccttc agtgcagaca acctcacagc ccctgatgag gacagagaga   3060
tgaacaacct ccagctggcc ctggcccgca tccagagggg cctgcgcttt gtcaagcgga   3120
ccacctggga tttctgctgt ggtctcctgc ggcagcggcc tcagaagccc gcagcccttg   3180
ccgcccaggg ccagctgccc agctgcattg ccacccccta ctccccgcca cccccagaga   3240
cggagaaggt gcctcccacc cgcaaggaaa cacggtttga ggaaggcgag caaccaggcc   3300
agggcacccc cggggatcca gagcccgtgt gtgtgcccat cgctgtggcc gagtcagaca   3360
cagatgacca agaagaagat gaggagaaca gcctgggcac ggaggaggag tccagcaagc   3420
agcaggaatc ccagcctgtg tccggtggcc cagaggcccc tccggattcc aggacctgga   3480
gccaggtgtc agcgactgcc tcctctgagg ccgaggccag tgcatctcag gccgactggc   3540
ggcagcagtg gaaagcggaa ccccaggccc cagggtgcgg tgagacccca gaggacagtt   3600
gctccgaggg cagcacagca gacatgacca acaccgctga gctcctggag cagatccctg   3660
acctcggcca ggatgtcaag gacccagagg actgcttcac tgaaggctgt gtccggcgct   3720
gtccctgctg tgcggtggac accacacagg ccccagggaa ggtctggtgg cggttgcgca   3780
agacctgcta ccacatcgtg gagcacagct ggttcgagac attcatcatc ttcatgatcc   3840
tactcagcag tggagcgctg gccttcgagg acatctacct agaggagcgg aagaccatca   3900
aggttctgct tgagtatgcc gacaagatgt tcacatatgt cttcgtgctg gagatgctgc   3960
tcaagtgggt ggcctacggc ttcaagaagt acttcaccaa tgcctggtgc tggctcgact   4020
tcctcatcgt agacgtctct ctggtcagcc tggtggccaa caccctgggc tttgccgaga   4080
tgggccccat caagtcactg cggacgctgc gtgcactccg tcctctgaga gctctgtcac   4140
gatttgaggg catgagggtg gtggtcaatg ccctggtggg cgccatcccg tccatcatga   4200
acgtcctcct cgtctgcctc atcttctggc tcatcttcag catcatgggc gtgaacctct   4260
ttgcggggaa gtttgggagg tgcatcaacc agacagaggg agacttgcct ttgaactaca   4320
ccatcgtgaa caacaagagc cagtgtgagt ccttgaactt gaccggagaa ttgtactgga   4380
ccaaggtgaa agtcaacttt gacaacgtgg gggccgggta cctggccctt ctgcaggtgg   4440
caacatttaa aggctggatg gacattatgt atgcagctgt ggactccagg gggtatgaag   4500
agcagcctca gtgggaatac aacctctaca tgtacatcta ttttgtcatt ttcatcatct   4560
ttgggtcttt cttcaccctg aacctcttta ttggtgtcat cattgacaac ttcaaccaac   4620
agaagaaaaa gttagggggc caggacatct tcatgacaga ggagcagaag aagtactaca   4680
atgccatgaa gaagctgggc tccaagaagc cccagaagcc catcccacgg cccctgaaca   4740
agtaccaggg cttcatattc gacattgtga ccaagcaggc ctttgacgtc accatcatgt   4800
ttctgatctg cttgaatatg gtgaccatga tggtggagac agatgaccaa agtcctgaga   4860
aaatcaacat cttggccaag atcaacctgc tctttgtggc catcttcaca ggcgagtgta   4920
ttgtcaagct ggctgccctg cgccactact acttcaccaa cagctggaat atcttcgact   4980
tcgtggttgt catcctctcc atcgtgggag ccctcctagt gagtatgaag tgatatctca   5040
ctgaggtttt ggtttgcaaa agcaaatgac tgatgactaa cgatgcagga catctttcca   5100
tgtgcatgtt ggtcatttat atatcttcct tggagaaatc tctattcaga tccttagctc   5160
atttttaatt gggttatttc tcttcttctt gttgagttgt aagagttctt tacatattct   5220
ggatcacagt ctcttatcag atatatgatt taaaaatatt ttctcctagt ctgtgagttt   5280
tttcatttcc tagtggtgtc cattaaagca caaaagtttt acatgtt                 5327
```

<210> SEQ ID NO 7
<211> LENGTH: 1612
<212> TYPE: PRT
<213> ORGANISM: Homo sapiens

<400> SEQUENCE: 7

```
Met Ala Asn Phe Leu Leu Pro Arg Gly Thr Ser Ser Phe Arg Arg Phe
1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
    50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu
                85                  90                  95

Asn Lys Gly Lys Thr Ile Phe Arg Phe Ser Ala Thr Asn Ala Leu Tyr
            100                 105                 110

Val Leu Ser Pro Phe His Pro Ile Arg Arg Ala Ala Val Lys Ile Leu
        115                 120                 125

Val His Ser Leu Phe Asn Met Leu Ile Met Cys Thr Ile Leu Thr Asn
    130                 135                 140

Cys Val Phe Met Ala Gln His Asp Pro Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Gly Phe Cys Leu His Ala Phe Thr Phe Leu Arg Asp Pro
            180                 185                 190

Trp Asn Trp Leu Asp Phe Ser Val Ile Ile Met Ala Tyr Thr Thr Glu
        195                 200                 205

Phe Val Asp Leu Gly Asn Val Ser Ala Leu Arg Thr Phe Arg Val Leu
    210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
            260                 265                 270

Met Gly Asn Leu Arg His Lys Cys Val Arg Asn Phe Thr Ala Leu Asn
        275                 280                 285

Gly Thr Asn Gly Ser Val Glu Ala Asp Gly Leu Val Trp Glu Ser Leu
    290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                325                 330                 335

Glu Gly Tyr Arg Cys Leu Lys Ala Gly Glu Asn Pro Asp His Gly Tyr
            340                 345                 350

Thr Ser Phe Asp Ser Phe Ala Trp Ala Phe Leu Ala Leu Phe Arg Leu
        355                 360                 365

Met Thr Gln Asp Cys Trp Glu Arg Leu Tyr Gln Gln Thr Leu Arg Ser
```

-continued

```
    370                 375                 380

Ala Gly Lys Ile Tyr Met Ile Phe Phe Met Leu Val Ile Phe Leu Gly
385                 390                 395                 400

Ser Phe Tyr Leu Val Asn Leu Ile Leu Ala Val Val Ala Met Ala Tyr
                405                 410                 415

Glu Glu Gln Asn Gln Ala Thr Ile Ala Glu Thr Glu Glu Lys Glu Lys
            420                 425                 430

Arg Phe Gln Glu Ala Met Glu Met Leu Lys Lys Glu His Glu Ala Leu
        435                 440                 445

Thr Ile Arg Gly Val Asp Thr Val Ser Arg Ser Ser Leu Glu Met Ser
    450                 455                 460

Pro Leu Ala Pro Val Asn Ser His Glu Arg Arg Ser Lys Arg Arg Lys
465                 470                 475                 480

Arg Met Ser Ser Gly Thr Glu Glu Cys Gly Glu Asp Arg Leu Pro Lys
                485                 490                 495

Ser Asp Ser Glu Asp Gly Pro Arg Ala Met Asn His Leu Ser Leu Thr
            500                 505                 510

Arg Gly Leu Ser Arg Thr Ser Met Lys Pro Arg Ser Ser Arg Gly Ser
        515                 520                 525

Ile Phe Thr Phe Arg Arg Arg Asp Leu Gly Ser Glu Ala Asp Phe Ala
    530                 535                 540

Asp Asp Glu Asn Ser Thr Ala Gly Glu Ser Glu Ser His His Thr Ser
545                 550                 555                 560

Leu Leu Val Pro Trp Pro Leu Arg Arg Thr Ser Ala Gln Gly Gln Pro
                565                 570                 575

Ser Pro Gly Thr Ser Ala Pro Gly His Ala Leu His Gly Lys Lys Asn
            580                 585                 590

Ser Thr Val Asp Cys Asn Gly Val Val Ser Leu Leu Gly Ala Gly Asp
        595                 600                 605

Pro Glu Ala Thr Ser Pro Gly Ser His Leu Leu Arg Pro Val Met Leu
    610                 615                 620

Glu His Pro Pro Asp Thr Thr Thr Pro Ser Glu Glu Pro Gly Gly Pro
625                 630                 635                 640

Gln Met Leu Thr Ser Gln Ala Pro Cys Val Asp Gly Phe Glu Glu Pro
                645                 650                 655

Gly Ala Arg Gln Arg Ala Leu Ser Ala Val Ser Val Leu Thr Ser Ala
            660                 665                 670

Leu Glu Glu Leu Glu Glu Ser Arg His Lys Cys Pro Pro Cys Trp Asn
        675                 680                 685

Arg Leu Ala Gln Arg Tyr Leu Ile Trp Glu Cys Cys Pro Leu Trp Met
    690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
                725                 730                 735

Glu His Tyr Asn Met Thr Ser Glu Phe Glu Glu Met Leu Gln Val Gly
            740                 745                 750

Asn Leu Val Phe Thr Gly Ile Phe Thr Ala Glu Met Thr Phe Lys Ile
        755                 760                 765

Ile Ala Leu Asp Pro Tyr Tyr Tyr Phe Gln Gln Gly Trp Asn Ile Phe
    770                 775                 780

Asp Ser Ile Ile Val Ile Leu Ser Leu Met Glu Leu Gly Leu Ser Arg
785                 790                 795                 800
```

-continued

```
Met Ser Asn Leu Ser Val Leu Arg Ser Phe Arg Leu Leu Arg Val Phe
                805                 810                 815

Lys Leu Ala Lys Ser Trp Pro Thr Leu Asn Thr Leu Ile Lys Ile Ile
            820                 825                 830

Gly Asn Ser Val Gly Ala Leu Gly Asn Leu Thr Leu Val Leu Ala Ile
        835                 840                 845

Ile Val Phe Ile Phe Ala Val Val Gly Met Gln Leu Phe Gly Lys Asn
    850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
                885                 890                 895

Gly Glu Trp Ile Glu Thr Met Trp Asp Cys Met Glu Val Ser Gly Gln
            900                 905                 910

Ser Leu Cys Leu Leu Val Phe Leu Leu Val Met Val Ile Gly Asn Leu
        915                 920                 925

Val Val Leu Asn Leu Phe Leu Ala Leu Leu Leu Ser Ser Phe Ser Ala
    930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
                965                 970                 975

Thr Trp Asp Phe Cys Cys Gly Leu Leu Arg Gln Arg Pro Gln Lys Pro
            980                 985                 990

Ala Ala Leu Ala Ala Gln Gly Gln  Leu Pro Ser Cys Ile  Ala Thr Pro
        995                 1000                1005

Tyr Ser  Pro Pro Pro Pro Glu  Thr Glu Lys Val Pro  Pro Thr Arg
    1010                1015                1020

Lys Glu  Thr Arg Phe Glu Glu  Gly Glu Gln Pro Gly  Gln Gly Thr
    1025                1030                1035

Pro Gly  Asp Pro Glu Pro Val  Cys Val Pro Ile Ala  Val Ala Glu
    1040                1045                1050

Ser Asp  Thr Asp Asp Gln Glu  Glu Asp Glu Glu Asn  Ser Leu Gly
    1055                1060                1065

Thr Glu  Glu Glu Ser Ser Lys  Gln Gln Glu Ser Gln  Pro Val Ser
    1070                1075                1080

Gly Gly  Pro Glu Ala Pro Pro  Asp Ser Arg Thr Trp  Ser Gln Val
    1085                1090                1095

Ser Ala  Thr Ala Ser Ser Glu  Ala Glu Ala Ser Ala  Ser Gln Ala
    1100                1105                1110

Asp Trp  Arg Gln Gln Trp Lys  Ala Glu Pro Gln Ala  Pro Gly Cys
    1115                1120                1125

Gly Glu  Thr Pro Glu Asp Ser  Cys Ser Glu Gly Ser  Thr Ala Asp
    1130                1135                1140

Met Thr  Asn Thr Ala Glu Leu  Leu Glu Gln Ile Pro  Asp Leu Gly
    1145                1150                1155

Gln Asp  Val Lys Asp Pro Glu  Asp Cys Phe Thr Glu  Gly Cys Val
    1160                1165                1170

Arg Arg  Cys Pro Cys Cys Ala  Val Asp Thr Thr Gln  Ala Pro Gly
    1175                1180                1185

Lys Val  Trp Trp Arg Leu Arg  Lys Thr Cys Tyr His  Ile Val Glu
    1190                1195                1200
```

His Ser Trp Phe Glu Thr Phe Ile Ile Phe Met Ile Leu Leu Ser
1205 1210 1215

Ser Gly Ala Leu Ala Phe Glu Asp Ile Tyr Leu Glu Glu Arg Lys
1220 1225 1230

Thr Ile Lys Val Leu Leu Glu Tyr Ala Asp Lys Met Phe Thr Tyr
1235 1240 1245

Val Phe Val Leu Glu Met Leu Leu Lys Trp Val Ala Tyr Gly Phe
1250 1255 1260

Lys Lys Tyr Phe Thr Asn Ala Trp Cys Trp Leu Asp Phe Leu Ile
1265 1270 1275

Val Asp Val Ser Leu Val Ser Leu Val Ala Asn Thr Leu Gly Phe
1280 1285 1290

Ala Glu Met Gly Pro Ile Lys Ser Leu Arg Thr Leu Arg Ala Leu
1295 1300 1305

Arg Pro Leu Arg Ala Leu Ser Arg Phe Glu Gly Met Arg Val Val
1310 1315 1320

Val Asn Ala Leu Val Gly Ala Ile Pro Ser Ile Met Asn Val Leu
1325 1330 1335

Leu Val Cys Leu Ile Phe Trp Leu Ile Phe Ser Ile Met Gly Val
1340 1345 1350

Asn Leu Phe Ala Gly Lys Phe Gly Arg Cys Ile Asn Gln Thr Glu
1355 1360 1365

Gly Asp Leu Pro Leu Asn Tyr Thr Ile Val Asn Asn Lys Ser Gln
1370 1375 1380

Cys Glu Ser Leu Asn Leu Thr Gly Glu Leu Tyr Trp Thr Lys Val
1385 1390 1395

Lys Val Asn Phe Asp Asn Val Gly Ala Gly Tyr Leu Ala Leu Leu
1400 1405 1410

Gln Val Ala Thr Phe Lys Gly Trp Met Asp Ile Met Tyr Ala Ala
1415 1420 1425

Val Asp Ser Arg Gly Tyr Glu Glu Gln Pro Gln Trp Glu Tyr Asn
1430 1435 1440

Leu Tyr Met Tyr Ile Tyr Phe Val Ile Phe Ile Ile Phe Gly Ser
1445 1450 1455

Phe Phe Thr Leu Asn Leu Phe Ile Gly Val Ile Ile Asp Asn Phe
1460 1465 1470

Asn Gln Gln Lys Lys Lys Leu Gly Gly Gln Asp Ile Phe Met Thr
1475 1480 1485

Glu Glu Gln Lys Lys Tyr Tyr Asn Ala Met Lys Lys Leu Gly Ser
1490 1495 1500

Lys Lys Pro Gln Lys Pro Ile Pro Arg Pro Leu Asn Lys Tyr Gln
1505 1510 1515

Gly Phe Ile Phe Asp Ile Val Thr Lys Gln Ala Phe Asp Val Thr
1520 1525 1530

Ile Met Phe Leu Ile Cys Leu Asn Met Val Thr Met Met Val Glu
1535 1540 1545

Thr Asp Asp Gln Ser Pro Glu Lys Ile Asn Ile Leu Ala Lys Ile
1550 1555 1560

Asn Leu Leu Phe Val Ala Ile Phe Thr Gly Glu Cys Ile Val Lys
1565 1570 1575

Leu Ala Ala Leu Arg His Tyr Tyr Phe Thr Asn Ser Trp Asn Ile
1580 1585 1590

Phe Asp Phe Val Val Val Ile Leu Ser Ile Val Gly Ala Leu Leu

```
    1595                1600                1605

Val Ser  Met Lys
    1610


<210> SEQ ID NO 8
<211> LENGTH: 5170
<212> TYPE: DNA
<213> ORGANISM: Artificial Sequence
<220> FEATURE:
<223> OTHER INFORMATION: E28C SCN5A Splice Variant Complete Nucleotide
      Sequence

<400> SEQUENCE: 8

agacggcggc ggcgcccgta ggatgcaggg atcgctcccc cggggccgct gagcctgcgc     60

ccagtgcccc gagccccgcg ccgagccgag tccgcgccaa gcagcagccg cccaccccgg    120

ggcccggccg gggaccagc agcttcccca caggcaacgt gaggagagcc tgtgcccaga     180

agcaggatga gaagatggca aacttcctat tacctcgggg caccagcagc ttccgcaggt    240

tcacacggga gtccctggca gccatcgaga agcgcatggc agagaagcaa gcccgcggct    300

caaccacctt gcaggagagc cgagaggggc tgcccgagga ggaggctccc cggccccagc    360

tggacctgca ggcctccaaa aagctgccag atctctatgg caatccaccc caagagctca    420

tcggagagcc cctggaggac ctggacccct tctatagcac ccaaaagact ttcatcgtac    480

tgaataaagg caagaccatc ttccggttca gtgccaccaa cgccttgtat gtcctcagtc    540

ccttccaccc catccggaga gcggctgtga agattctggt tcactcgctc ttcaacatgc    600

tcatcatgtg caccatcctc accaactgcg tgttcatggc ccagcacgac cctccaccct    660

ggaccaagta tgtcgagtac accttcaccg ccatttacac ctttgagtct ctggtcaaga    720

ttctggctcg aggcttctgc ctgcacgcgt tcactttcct tcgggaccca tggaactggc    780

tggactttag tgtgattatc atggcataca caactgaatt tgtggacctg ggcaatgtct    840

cagccttacg caccttccga gtcctccggg ccctgaaaac tatatcagtc atttcagggc    900

tgaagaccat cgtgggggcc ctgatccagt ctgtgaagaa gctggctgat gtgatggtcc    960

tcacagtctt ctgcctcagc gtctttgccc tcatcggcct gcagctcttc atgggcaacc   1020

taaggcacaa gtgcgtgcgc aacttcacag cgctcaacgg caccaacggc tccgtggagg   1080

ccgacggctt ggtctgggaa tccctggacc tttacctcag tgatccagaa aattacctgc   1140

tcaagaacgg cacctctgat gtgttactgt gtgggaacag ctctgacgct gggacatgtc   1200

cggagggcta ccggtgccta aaggcaggcg agaaccccga ccacggctac accagcttcg   1260

attcctttgc ctgggccttt cttgcactct tccgcctgat gacgcaggac tgctgggagc   1320

gcctctatca gcagaccctc aggtccgcag ggaagatcta catgatcttc ttcatgcttg   1380

tcatcttcct ggggtccttc tacctggtga acctgatcct ggccgtggtc gcaatggcct   1440

atgaggagca aaaccaagcc accatcgctg agaccgagga gaaggaaaag cgcttccagg   1500

aggccatgga aatgctcaag aaagaacacg aggccctcac catcaggggt gtggataccg   1560

tgtcccgtag ctccttggag atgtcccctt tggccccagt aaacagccat gagagaagaa   1620

gcaagaggag aaaacggatg tcttcaggaa ctgaggagtg tggggaggac aggctcccca   1680

agtctgactc agaagatggt cccagagcaa tgaatcatct cagcctcacc cgtggcctca   1740

gcaggacttc tatgaagcca cgttccagcc gcgggagcat tttcaccttt cgcaggcgag   1800

acctgggttc tgaagcagat tttgcagatg atgaaaacag cacagcgggg gagagcgaga   1860

gccaccacac atcactgctg gtgccctggc ccctgcgccg gaccagtgcc cagggacagc   1920
```

```
ccagtcccgg aacctcggct cctggccacg ccctccatgg caaaaagaac agcactgtgg   1980
actgcaatgg ggtggtctca ttactggggg caggcgaccc agaggccaca tccccaggaa   2040
gccacctcct ccgccctgtg atgctagagc acccgccaga cacgaccacg ccatcggagg   2100
agccaggcgg gccccagatg ctgacctccc aggctccgtg tgtagatggc ttcgaggagc   2160
caggagcacg gcagcgggcc ctcagcgcag tcagcgtcct caccagcgca ctggaagagt   2220
tagaggagtc tcgccacaag tgtccaccat gctggaaccg tctcgcccag cgctacctga   2280
tctgggagtg ctgcccgctg tggatgtcca tcaagcaggg agtgaagttg gtggtcatgg   2340
acccgtttac tgacctcacc atcactatgt gcatcgtact caacacactc ttcatggcgc   2400
tggagcacta caacatgaca agtgaattcg aggagatgct gcaggtcgga aacctggtct   2460
tcacagggat tttcacagca gagatgacct tcaagatcat tgccctcgac ccctactact   2520
acttccaaca gggctggaac atcttcgaca gcatcatcgt catccttagc ctcatggagc   2580
tgggcctgtc ccgcatgagc aacttgtcgg tgctgcgctc cttccgcctg ctgcgggtct   2640
tcaagctggc caaatcatgg cccaccctga acacactcat caagatcatc gggaactcag   2700
tgggggcact ggggaacctg acactggtgc tagccatcat cgtgttcatc tttgctgtgg   2760
tgggcatgca gctctttggc aagaactact cggagctgag ggacagcgac tcaggcctgc   2820
tgcctcgctg gcacatgatg gacttctttc atgccttcct catcatcttc cgcatcctct   2880
gtggagagtg gatcgagacc atgtgggact gcatggaggt gtcggggcag tcattatgcc   2940
tgctggtctt cttgcttgtt atggtcattg gcaaccttgt ggtcctgaat ctcttcctgg   3000
ccttgctgct cagctccttc agtgcagaca acctcacagc ccctgatgag gacagagaga   3060
tgaacaacct ccagctggcc ctggcccgca tccagagggg cctgcgcttt gtcaagcgga   3120
ccacctggga tttctgctgt ggtctcctgc ggcagcggcc tcagaagccc gcagcccttg   3180
ccgcccaggg ccagctgccc agctgcattg ccacccccta ctccccgcca cccccagaga   3240
cggagaaggt gcctcccacc cgcaaggaaa cacggtttga ggaaggcgag caaccaggcc   3300
agggcacccc cggggatcca gagcccgtgt gtgtgcccat cgctgtggcc gagtcagaca   3360
cagatgacca agaagaagat gaggagaaca gcctgggcac ggaggaggag tccagcaagc   3420
agcaggaatc ccagcctgtg tccggtggcc cagaggcccc tccggattcc aggacctgga   3480
gccaggtgtc agcgactgcc tcctctgagg ccgaggccag tgcatctcag gccgactggc   3540
ggcagcagtg gaaagcggaa ccccaggccc cagggtgcgg tgagacccca gaggacagtt   3600
gctccgaggg cagcacagca gacatgacca acaccgctga gctcctggag cagatccctg   3660
acctcggcca ggatgtcaag gacccagagg actgcttcac tgaaggctgt gtccggcgct   3720
gtccctgctg tgcggtggac accacacagg ccccagggaa ggtctggtgg cggttgcgca   3780
agacctgcta ccacatcgtg gagcacagct ggttcgagac attcatcatc ttcatgatcc   3840
tactcagcag tggagcgctg gccttcgagg acatctacct agaggagcgg aagaccatca   3900
aggttctgct tgagtatgcc gacaagatgt tcacatatgt cttcgtgctg gagatgctgc   3960
tcaagtgggt ggcctacggc ttcaagaagt acttcaccaa tgcctggtgc tggctcgact   4020
tcctcatcgt agacgtctct ctggtcagcc tggtggccaa caccctgggc tttgccgaga   4080
tgggccccat caagtcactg cggacgctgc gtgcactccg tcctctgaga gctctgtcac   4140
gatttgaggg catgagggtg gtggtcaatg ccctggtggg cgccatcccg tccatcatga   4200
acgtcctcct cgtctgcctc atcttctggc tcatcttcag catcatgggc gtgaacctct   4260
```

-continued

```
ttgcggggaa gtttgggagg tgcatcaacc agacagaggg agacttgcct ttgaactaca   4320

ccatcgtgaa caacaagagc cagtgtgagt ccttgaactt gaccggagaa ttgtactgga   4380

ccaaggtgaa agtcaacttt gacaacgtgg gggccgggta cctggccctt ctgcaggtgg   4440

caacatttaa aggctggatg gacattatgt atgcagctgt ggactccagg gggtatgaag   4500

agcagcctca gtgggaatac aacctctaca tgtacatcta ttttgtcatt ttcatcatct   4560

ttgggtcttt cttcaccctg aacctcttta ttggtgtcat cattgacaac ttcaaccaac   4620

agaagaaaaa gttagggggc caggacatct tcatgacaga ggagcagaag aagtactaca   4680

atgccatgaa gaagctgggc tccaagaagc cccagaagcc catcccacgg cccctgaaca   4740

agtaccaggg cttcatattc gacattgtga ccaagcaggc ctttgacgtc accatcatgt   4800

ttctgatctg cttgaatatg gtgaccatga tggtggagac agatgaccaa agtcctgaga   4860

aaatcaacat cttggccaag atcaacctgc tctttgtggc catcttcaca ggcgagtgta   4920

ttgtcaagct ggctgccctg cgccactact acttcaccaa cagctggaat atcttcgact   4980

tcgtggttgt catcctctcc atcgtggaac tgcacaatga ccagcaggag gggagaagag   5040

agtaggaaaa aggagggaag gacagacatc aagtgccaga tgttgtctga actaatcgag   5100

cacttctcac caaacttcat gtataaataa aatacatatt tttaaaacaa accaataaat   5160

ggcttacatg                                                          5170


<210> SEQ ID NO 9
<211> LENGTH: 1616
<212> TYPE: PRT
<213> ORGANISM: Homo sapiens

<400> SEQUENCE: 9

Met Ala Asn Phe Leu Leu Pro Arg Gly Thr Ser Ser Phe Arg Arg Phe
1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
    50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu
                85                  90                  95

Asn Lys Gly Lys Thr Ile Phe Arg Phe Ser Ala Thr Asn Ala Leu Tyr
            100                 105                 110

Val Leu Ser Pro Phe His Pro Ile Arg Arg Ala Ala Val Lys Ile Leu
        115                 120                 125

Val His Ser Leu Phe Asn Met Leu Ile Met Cys Thr Ile Leu Thr Asn
    130                 135                 140

Cys Val Phe Met Ala Gln His Asp Pro Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Gly Phe Cys Leu His Ala Phe Thr Phe Leu Arg Asp Pro
            180                 185                 190

Trp Asn Trp Leu Asp Phe Ser Val Ile Ile Met Ala Tyr Thr Thr Glu
        195                 200                 205
```

-continued

```
Phe Val Asp Leu Gly Asn Val Ser Ala Leu Arg Thr Phe Arg Val Leu
    210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
            260                 265                 270

Met Gly Asn Leu Arg His Lys Cys Val Arg Asn Phe Thr Ala Leu Asn
        275                 280                 285

Gly Thr Asn Gly Ser Val Glu Ala Asp Gly Leu Val Trp Glu Ser Leu
    290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                325                 330                 335

Glu Gly Tyr Arg Cys Leu Lys Ala Gly Glu Asn Pro Asp His Gly Tyr
            340                 345                 350

Thr Ser Phe Asp Ser Phe Ala Trp Ala Phe Leu Ala Leu Phe Arg Leu
        355                 360                 365

Met Thr Gln Asp Cys Trp Glu Arg Leu Tyr Gln Gln Thr Leu Arg Ser
    370                 375                 380

Ala Gly Lys Ile Tyr Met Ile Phe Phe Met Leu Val Ile Phe Leu Gly
385                 390                 395                 400

Ser Phe Tyr Leu Val Asn Leu Ile Leu Ala Val Val Ala Met Ala Tyr
                405                 410                 415

Glu Glu Gln Asn Gln Ala Thr Ile Ala Glu Thr Glu Glu Lys Glu Lys
            420                 425                 430

Arg Phe Gln Glu Ala Met Glu Met Leu Lys Lys Glu His Glu Ala Leu
        435                 440                 445

Thr Ile Arg Gly Val Asp Thr Val Ser Arg Ser Ser Leu Glu Met Ser
    450                 455                 460

Pro Leu Ala Pro Val Asn Ser His Glu Arg Arg Ser Lys Arg Arg Lys
465                 470                 475                 480

Arg Met Ser Ser Gly Thr Glu Glu Cys Gly Glu Asp Arg Leu Pro Lys
                485                 490                 495

Ser Asp Ser Glu Asp Gly Pro Arg Ala Met Asn His Leu Ser Leu Thr
            500                 505                 510

Arg Gly Leu Ser Arg Thr Ser Met Lys Pro Arg Ser Ser Arg Gly Ser
        515                 520                 525

Ile Phe Thr Phe Arg Arg Arg Asp Leu Gly Ser Glu Ala Asp Phe Ala
    530                 535                 540

Asp Asp Glu Asn Ser Thr Ala Gly Glu Ser Glu Ser His His Thr Ser
545                 550                 555                 560

Leu Leu Val Pro Trp Pro Leu Arg Arg Thr Ser Ala Gln Gly Gln Pro
                565                 570                 575

Ser Pro Gly Thr Ser Ala Pro Gly His Ala Leu His Gly Lys Lys Asn
            580                 585                 590

Ser Thr Val Asp Cys Asn Gly Val Val Ser Leu Leu Gly Ala Gly Asp
        595                 600                 605

Pro Glu Ala Thr Ser Pro Gly Ser His Leu Leu Arg Pro Val Met Leu
    610                 615                 620

Glu His Pro Pro Asp Thr Thr Thr Pro Ser Glu Glu Pro Gly Gly Pro
```

-continued

```
625                 630                 635                 640

Gln Met Leu Thr Ser Gln Ala Pro Cys Val Asp Gly Phe Glu Glu Pro
                645                 650                 655

Gly Ala Arg Gln Arg Ala Leu Ser Ala Val Ser Val Leu Thr Ser Ala
            660                 665                 670

Leu Glu Glu Leu Glu Glu Ser Arg His Lys Cys Pro Pro Cys Trp Asn
        675                 680                 685

Arg Leu Ala Gln Arg Tyr Leu Ile Trp Glu Cys Cys Pro Leu Trp Met
    690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
                725                 730                 735

Glu His Tyr Asn Met Thr Ser Glu Phe Glu Glu Met Leu Gln Val Gly
            740                 745                 750

Asn Leu Val Phe Thr Gly Ile Phe Thr Ala Glu Met Thr Phe Lys Ile
        755                 760                 765

Ile Ala Leu Asp Pro Tyr Tyr Tyr Phe Gln Gln Gly Trp Asn Ile Phe
    770                 775                 780

Asp Ser Ile Ile Val Ile Leu Ser Leu Met Glu Leu Gly Leu Ser Arg
785                 790                 795                 800

Met Ser Asn Leu Ser Val Leu Arg Ser Phe Arg Leu Leu Arg Val Phe
                805                 810                 815

Lys Leu Ala Lys Ser Trp Pro Thr Leu Asn Thr Leu Ile Lys Ile Ile
            820                 825                 830

Gly Asn Ser Val Gly Ala Leu Gly Asn Leu Thr Leu Val Leu Ala Ile
        835                 840                 845

Ile Val Phe Ile Phe Ala Val Val Gly Met Gln Leu Phe Gly Lys Asn
    850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
                885                 890                 895

Gly Glu Trp Ile Glu Thr Met Trp Asp Cys Met Glu Val Ser Gly Gln
            900                 905                 910

Ser Leu Cys Leu Leu Val Phe Leu Leu Val Met Val Ile Gly Asn Leu
        915                 920                 925

Val Val Leu Asn Leu Phe Leu Ala Leu Leu Leu Ser Ser Phe Ser Ala
    930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
                965                 970                 975

Thr Trp Asp Phe Cys Cys Gly Leu Leu Arg Gln Arg Pro Gln Lys Pro
            980                 985                 990

Ala Ala Leu Ala Ala Gln Gly Gln  Leu Pro Ser Cys Ile  Ala Thr Pro
        995                 1000                1005

Tyr Ser  Pro Pro Pro Pro Glu  Thr Glu Lys Val Pro  Pro Thr Arg
    1010                1015                1020

Lys Glu  Thr Arg Phe Glu Glu  Gly Glu Gln Pro Gly  Gln Gly Thr
    1025                1030                1035

Pro Gly  Asp Pro Glu Pro Val  Cys Val Pro Ile Ala  Val Ala Glu
    1040                1045                1050
```

-continued

```
Ser Asp  Thr Asp Asp Gln Glu  Glu Asp Glu Glu Asn  Ser Leu Gly
    1055                 1060                 1065

Thr Glu  Glu Glu Ser Ser Lys  Gln Gln Glu Ser Gln  Pro Val Ser
    1070                 1075                 1080

Gly Gly  Pro Glu Ala Pro Pro  Asp Ser Arg Thr Trp  Ser Gln Val
    1085                 1090                 1095

Ser Ala  Thr Ala Ser Ser Glu  Ala Glu Ala Ser Ala  Ser Gln Ala
    1100                 1105                 1110

Asp Trp  Arg Gln Gln Trp Lys  Ala Glu Pro Gln Ala  Pro Gly Cys
    1115                 1120                 1125

Gly Glu  Thr Pro Glu Asp Ser  Cys Ser Glu Gly Ser  Thr Ala Asp
    1130                 1135                 1140

Met Thr  Asn Thr Ala Glu Leu  Leu Glu Gln Ile Pro  Asp Leu Gly
    1145                 1150                 1155

Gln Asp  Val Lys Asp Pro Glu  Asp Cys Phe Thr Glu  Gly Cys Val
    1160                 1165                 1170

Arg Arg  Cys Pro Cys Cys Ala  Val Asp Thr Thr Gln  Ala Pro Gly
    1175                 1180                 1185

Lys Val  Trp Trp Arg Leu Arg  Lys Thr Cys Tyr His  Ile Val Glu
    1190                 1195                 1200

His Ser  Trp Phe Glu Thr Phe  Ile Ile Phe Met Ile  Leu Leu Ser
    1205                 1210                 1215

Ser Gly  Ala Leu Ala Phe Glu  Asp Ile Tyr Leu Glu  Glu Arg Lys
    1220                 1225                 1230

Thr Ile  Lys Val Leu Leu Glu  Tyr Ala Asp Lys Met  Phe Thr Tyr
    1235                 1240                 1245

Val Phe  Val Leu Glu Met Leu  Leu Lys Trp Val Ala  Tyr Gly Phe
    1250                 1255                 1260

Lys Lys  Tyr Phe Thr Asn Ala  Trp Cys Trp Leu Asp  Phe Leu Ile
    1265                 1270                 1275

Val Asp  Val Ser Leu Val Ser  Leu Val Ala Asn Thr  Leu Gly Phe
    1280                 1285                 1290

Ala Glu  Met Gly Pro Ile Lys  Ser Leu Arg Thr Leu  Arg Ala Leu
    1295                 1300                 1305

Arg Pro  Leu Arg Ala Leu Ser  Arg Phe Glu Gly Met  Arg Val Val
    1310                 1315                 1320

Val Asn  Ala Leu Val Gly Ala  Ile Pro Ser Ile Met  Asn Val Leu
    1325                 1330                 1335

Leu Val  Cys Leu Ile Phe Trp  Leu Ile Phe Ser Ile  Met Gly Val
    1340                 1345                 1350

Asn Leu  Phe Ala Gly Lys Phe  Gly Arg Cys Ile Asn  Gln Thr Glu
    1355                 1360                 1365

Gly Asp  Leu Pro Leu Asn Tyr  Thr Ile Val Asn Asn  Lys Ser Gln
    1370                 1375                 1380

Cys Glu  Ser Leu Asn Leu Thr  Gly Glu Leu Tyr Trp  Thr Lys Val
    1385                 1390                 1395

Lys Val  Asn Phe Asp Asn Val  Gly Ala Gly Tyr Leu  Ala Leu Leu
    1400                 1405                 1410

Gln Val  Ala Thr Phe Lys Gly  Trp Met Asp Ile Met  Tyr Ala Ala
    1415                 1420                 1425

Val Asp  Ser Arg Gly Tyr Glu  Glu Gln Pro Gln Trp  Glu Tyr Asn
    1430                 1435                 1440
```

-continued

```
Leu Tyr  Met Tyr Ile Tyr Phe  Val Ile Phe Ile Ile  Phe Gly Ser
    1445                 1450                 1455

Phe Phe  Thr Leu Asn Leu Phe  Ile Gly Val Ile Ile  Asp Asn Phe
    1460                 1465                 1470

Asn Gln  Gln Lys Lys Lys Leu  Gly Gly Gln Asp Ile  Phe Met Thr
    1475                 1480                 1485

Glu Glu  Gln Lys Lys Tyr Tyr  Asn Ala Met Lys Lys  Leu Gly Ser
    1490                 1495                 1500

Lys Lys  Pro Gln Lys Pro Ile  Pro Arg Pro Leu Asn  Lys Tyr Gln
    1505                 1510                 1515

Gly Phe  Ile Phe Asp Ile Val  Thr Lys Gln Ala Phe  Asp Val Thr
    1520                 1525                 1530

Ile Met  Phe Leu Ile Cys Leu  Asn Met Val Thr Met  Met Val Glu
    1535                 1540                 1545

Thr Asp  Asp Gln Ser Pro Glu  Lys Ile Asn Ile Leu  Ala Lys Ile
    1550                 1555                 1560

Asn Leu  Leu Phe Val Ala Ile  Phe Thr Gly Glu Cys  Ile Val Lys
    1565                 1570                 1575

Leu Ala  Ala Leu Arg His Tyr  Tyr Phe Thr Asn Ser  Trp Asn Ile
    1580                 1585                 1590

Phe Asp  Phe Val Val Val Ile  Leu Ser Ile Val Glu  Leu His Asn
    1595                 1600                 1605

Asp Gln  Gln Glu Gly Arg Arg  Glu
    1610                 1615


<210> SEQ ID NO 10
<211> LENGTH: 5120
<212> TYPE: DNA
<213> ORGANISM: Artificial Sequence
<220> FEATURE:
<223> OTHER INFORMATION: E28D SCN5A Splice Variant Complete Nucleotide
      Sequence

<400> SEQUENCE: 10

agacggcggc ggcgcccgta ggatgcaggg atcgctcccc cggggccgct gagcctgcgc     60

ccagtgcccc gagccccgcg ccgagccgag tccgcgccaa gcagcagccg cccaccccgg    120

ggcccggccg gggaccagc agcttcccca caggcaacgt gaggagagcc tgtgcccaga    180

agcaggatga gaagatggca aacttcctat tacctcgggg caccagcagc ttccgcaggt    240

tcacacggga gtccctggca gccatcgaga agcgcatggc agagaagcaa gcccgcggct    300

caaccacctt gcaggagagc cgagaggggc tgcccgagga ggaggctccc cggccccagc    360

tggacctgca ggcctccaaa aagctgccag atctctatgg caatccaccc caagagctca    420

tcggagagcc cctggaggac ctggacccct tctatagcac ccaaaagact ttcatcgtac    480

tgaataaagg caagaccatc ttccggttca gtgccaccaa cgccttgtat gtcctcagtc    540

ccttccaccc catccggaga gcggctgtga agattctggt tcactcgctc ttcaacatgc    600

tcatcatgtg caccatcctc accaactgcg tgttcatggc ccagcacgac cctccaccct    660

ggaccaagta tgtcgagtac accttcaccg ccatttacac ctttgagtct ctggtcaaga    720

ttctggctcg aggcttctgc ctgcacgcgt tcactttcct tcgggaccca tggaactggc    780

tggactttag tgtgattatc atggcataca caactgaatt tgtggacctg ggcaatgtct    840

cagccttacg caccttccga gtcctccggg ccctgaaaac tatatcagtc atttcagggc    900

tgaagaccat cgtgggggcc ctgatccagt ctgtgaagaa gctggctgat gtgatggtcc    960
```

-continued

```
tcacagtctt ctgcctcagc gtctttgccc tcatcggcct gcagctcttc atgggcaacc   1020
taaggcacaa gtgcgtgcgc aacttcacag cgctcaacgg caccaacggc tccgtggagg   1080
ccgacggctt ggtctgggaa tccctggacc tttacctcag tgatccagaa aattacctgc   1140
tcaagaacgg cacctctgat gtgttactgt gtgggaacag ctctgacgct gggacatgtc   1200
cggagggcta ccggtgccta aggcaggcg agaaccccga ccacggctac accagcttcg    1260
attcctttgc ctgggccttt cttgcactct tccgcctgat gacgcaggac tgctgggagc   1320
gcctctatca gcagaccctc aggtccgcag ggaagatcta catgatcttc ttcatgcttg   1380
tcatcttcct ggggtccttc tacctggtga acctgatcct ggccgtggtc gcaatggcct   1440
atgaggagca aaaccaagcc accatcgctg agaccgagga gaaggaaaag cgcttccagg   1500
aggccatgga aatgctcaag aaagaacacg aggccctcac catcaggggt gtggataccg   1560
tgtcccgtag ctccttggag atgtcccctt tggccccagt aaacagccat gagagaagaa   1620
gcaagaggag aaaacggatg tcttcaggaa ctgaggagtg tggggaggac aggctcccca   1680
agtctgactc agaagatggt cccagagcaa tgaatcatct cagcctcacc cgtggcctca   1740
gcaggacttc tatgaagcca cgttccagcc gcgggagcat tttcaccttt cgcaggcgag   1800
acctgggttc tgaagcagat tttgcagatg atgaaaacag cacagcgggg gagagcgaga   1860
gccaccacac atcactgctg gtgccctggc ccctgcgccg gaccagtgcc cagggacagc   1920
ccagtcccgg aacctcggct cctggccacg ccctccatgg caaaaagaac agcactgtgg   1980
actgcaatgg ggtggtctca ttactggggg caggcgaccc agaggccaca tccccaggaa   2040
gccacctcct ccgccctgtg atgctagagc acccgccaga cacgaccacg ccatcggagg   2100
agccaggcgg gccccagatg ctgacctccc aggctccgtg tgtagatggc ttcgaggagc   2160
caggagcacg gcagcgggcc ctcagcgcag tcagcgtcct caccagcgca ctggaagagt   2220
tagaggagtc tcgccacaag tgtccaccat gctggaaccg tctcgcccag cgctacctga   2280
tctgggagtg ctgcccgctg tggatgtcca tcaagcaggg agtgaagttg gtggtcatgg   2340
acccgtttac tgacctcacc atcactatgt gcatcgtact caacacactc ttcatggcgc   2400
tggagcacta caacatgaca agtgaattcg aggagatgct gcaggtcgga aacctggtct   2460
tcacagggat tttcacagca gagatgacct tcaagatcat tgccctcgac ccctactact   2520
acttccaaca gggctggaac atcttcgaca gcatcatcgt catccttagc ctcatggagc   2580
tgggcctgtc ccgcatgagc aacttgtcgg tgctgcgctc cttccgcctg ctgcgggtct   2640
tcaagctggc caaatcatgg cccaccctga acacactcat caagatcatc gggaactcag   2700
tgggggcact ggggaacctg acactggtgc tagccatcat cgtgttcatc tttgctgtgg   2760
tgggcatgca gctctttggc aagaactact cggagctgag ggacagcgac tcaggcctgc   2820
tgcctcgctg gcacatgatg gacttctttc atgccttcct catcatcttc cgcatcctct   2880
gtggagagtg gatcgagacc atgtgggact gcatggaggt gtcggggcag tcattatgcc   2940
tgctggtctt cttgcttgtt atggtcattg gcaaccttgt ggtcctgaat ctcttcctgg   3000
ccttgctgct cagctccttc agtgcagaca acctcacagc ccctgatgag gacagagaga   3060
tgaacaacct ccagctggcc ctggcccgca tccagagggg cctgcgcttt gtcaagcgga   3120
ccacctggga tttctgctgt ggtctcctgc ggcagcggcc tcagaagccc gcagcccttg   3180
ccgcccaggg ccagctgccc agctgcattg ccacccccta ctccccgcca cccccagaga   3240
cggagaaggt gcctcccacc cgcaaggaaa cacggtttga ggaaggcgag caaccaggcc   3300
agggcacccc cggggatcca gagcccgtgt gtgtgcccat cgctgtggcc gagtcagaca   3360
```

-continued

```
cagatgacca agaagaagat gaggagaaca gcctgggcac ggaggaggag tccagcaagc   3420

agcaggaatc ccagcctgtg tccggtggcc cagaggcccc tccggattcc aggacctgga   3480

gccaggtgtc agcgactgcc tcctctgagg ccgaggccag tgcatctcag gccgactggc   3540

ggcagcagtg gaaagcggaa ccccaggccc cagggtgcgg tgagacccca gaggacagtt   3600

gctccgaggg cagcacagca gacatgacca acaccgctga gctcctggag cagatccctg   3660

acctcggcca ggatgtcaag gacccagagg actgcttcac tgaaggctgt gtccggcgct   3720

gtccctgctg tgcggtggac accacacagg ccccagggaa ggtctggtgg cggttgcgca   3780

agacctgcta ccacatcgtg gagcacagct ggttcgagac attcatcatc ttcatgatcc   3840

tactcagcag tggagcgctg gccttcgagg acatctacct agaggagcgg aagaccatca   3900

aggttctgct tgagtatgcc gacaagatgt tcacatatgt cttcgtgctg gagatgctgc   3960

tcaagtgggt ggcctacggc ttcaagaagt acttcaccaa tgcctggtgc tggctcgact   4020

tcctcatcgt agacgtctct ctggtcagcc tggtggccaa caccctgggc tttgccgaga   4080

tgggccccat caagtcactg cggacgctgc gtgcactccg tcctctgaga gctctgtcac   4140

gatttgaggg catgagggtg gtggtcaatg ccctggtggg cgccatcccg tccatcatga   4200

acgtcctcct cgtctgcctc atcttctggc tcatcttcag catcatgggc gtgaacctct   4260

ttgcggggaa gtttgggagg tgcatcaacc agacagaggg agacttgcct ttgaactaca   4320

ccatcgtgaa caacaagagc cagtgtgagt ccttgaactt gaccggagaa ttgtactgga   4380

ccaaggtgaa agtcaacttt gacaacgtgg gggccgggta cctggccctt ctgcaggtgg   4440

caacatttaa aggctggatg gacattatgt atgcagctgt ggactccagg gggtatgaag   4500

agcagcctca gtgggaatac aacctctaca tgtacatcta ttttgtcatt ttcatcatct   4560

ttgggtcttt cttcaccctg aacctcttta ttggtgtcat cattgacaac ttcaaccaac   4620

agaagaaaaa gttagggggc caggacatct tcatgacaga ggagcagaag aagtactaca   4680

atgccatgaa gaagctgggc tccaagaagc cccagaagcc catcccacgg cccctgaaca   4740

agtaccaggg cttcatattc gacattgtga ccaagcaggc ctttgacgtc accatcatgt   4800

ttctgatctg cttgaatatg gtgaccatga tggtggagac agatgaccaa agtcctgaga   4860

aaatcaacat cttggccaag atcaacctgc tctttgtggc catcttcaca ggcgagtgta   4920

ttgtcaagct ggctgccctg cgccactact acttcaccaa cagctggaat atcttcgact   4980

tcgtggttgt catcctctcc atcgtgggca ctgtgctctc ggacatcatc cagaagtact   5040

tcttctcccc gacgctcttc cgagtcatcc gcctggcccg aataggccgc atcctcagac   5100

tgatccgagg ggccaagggg                                                5120
```

<210> SEQ ID NO 11
<211> LENGTH: 1642
<212> TYPE: PRT
<213> ORGANISM: Homo sapiens

<400> SEQUENCE: 11

```
Met Ala Asn Phe Leu Leu Pro Arg Gly Thr Ser Ser Phe Arg Arg Phe
1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
```

-continued

```
    50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu
                85                  90                  95

Asn Lys Gly Lys Thr Ile Phe Arg Phe Ser Ala Thr Asn Ala Leu Tyr
            100                 105                 110

Val Leu Ser Pro Phe His Pro Ile Arg Arg Ala Ala Val Lys Ile Leu
        115                 120                 125

Val His Ser Leu Phe Asn Met Leu Ile Met Cys Thr Ile Leu Thr Asn
    130                 135                 140

Cys Val Phe Met Ala Gln His Asp Pro Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Gly Phe Cys Leu His Ala Phe Thr Phe Leu Arg Asp Pro
            180                 185                 190

Trp Asn Trp Leu Asp Phe Ser Val Ile Ile Met Ala Tyr Thr Thr Glu
        195                 200                 205

Phe Val Asp Leu Gly Asn Val Ser Ala Leu Arg Thr Phe Arg Val Leu
    210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
            260                 265                 270

Met Gly Asn Leu Arg His Lys Cys Val Arg Asn Phe Thr Ala Leu Asn
        275                 280                 285

Gly Thr Asn Gly Ser Val Glu Ala Asp Gly Leu Val Trp Glu Ser Leu
    290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                325                 330                 335

Glu Gly Tyr Arg Cys Leu Lys Ala Gly Glu Asn Pro Asp His Gly Tyr
            340                 345                 350

Thr Ser Phe Asp Ser Phe Ala Trp Ala Phe Leu Ala Leu Phe Arg Leu
        355                 360                 365

Met Thr Gln Asp Cys Trp Glu Arg Leu Tyr Gln Gln Thr Leu Arg Ser
    370                 375                 380

Ala Gly Lys Ile Tyr Met Ile Phe Phe Met Leu Val Ile Phe Leu Gly
385                 390                 395                 400

Ser Phe Tyr Leu Val Asn Leu Ile Leu Ala Val Val Ala Met Ala Tyr
                405                 410                 415

Glu Glu Gln Asn Gln Ala Thr Ile Ala Glu Thr Glu Glu Lys Glu Lys
            420                 425                 430

Arg Phe Gln Glu Ala Met Glu Met Leu Lys Lys Glu His Glu Ala Leu
        435                 440                 445

Thr Ile Arg Gly Val Asp Thr Val Ser Arg Ser Ser Leu Glu Met Ser
    450                 455                 460

Pro Leu Ala Pro Val Asn Ser His Glu Arg Arg Ser Lys Arg Arg Lys
465                 470                 475                 480
```

```
Arg Met Ser Ser Gly Thr Glu Glu Cys Gly Glu Asp Arg Leu Pro Lys
                485                 490                 495

Ser Asp Ser Glu Asp Gly Pro Arg Ala Met Asn His Leu Ser Leu Thr
            500                 505                 510

Arg Gly Leu Ser Arg Thr Ser Met Lys Pro Arg Ser Ser Arg Gly Ser
        515                 520                 525

Ile Phe Thr Phe Arg Arg Arg Asp Leu Gly Ser Glu Ala Asp Phe Ala
    530                 535                 540

Asp Asp Glu Asn Ser Thr Ala Gly Glu Ser Glu Ser His His Thr Ser
545                 550                 555                 560

Leu Leu Val Pro Trp Pro Leu Arg Arg Thr Ser Ala Gln Gly Gln Pro
                565                 570                 575

Ser Pro Gly Thr Ser Ala Pro Gly His Ala Leu His Gly Lys Lys Asn
            580                 585                 590

Ser Thr Val Asp Cys Asn Gly Val Val Ser Leu Leu Gly Ala Gly Asp
        595                 600                 605

Pro Glu Ala Thr Ser Pro Gly Ser His Leu Leu Arg Pro Val Met Leu
    610                 615                 620

Glu His Pro Pro Asp Thr Thr Thr Pro Ser Glu Glu Pro Gly Gly Pro
625                 630                 635                 640

Gln Met Leu Thr Ser Gln Ala Pro Cys Val Asp Gly Phe Glu Glu Pro
                645                 650                 655

Gly Ala Arg Gln Arg Ala Leu Ser Ala Val Ser Val Leu Thr Ser Ala
            660                 665                 670

Leu Glu Glu Leu Glu Glu Ser Arg His Lys Cys Pro Pro Cys Trp Asn
        675                 680                 685

Arg Leu Ala Gln Arg Tyr Leu Ile Trp Glu Cys Cys Pro Leu Trp Met
    690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
                725                 730                 735

Glu His Tyr Asn Met Thr Ser Glu Phe Glu Glu Met Leu Gln Val Gly
            740                 745                 750

Asn Leu Val Phe Thr Gly Ile Phe Thr Ala Glu Met Thr Phe Lys Ile
        755                 760                 765

Ile Ala Leu Asp Pro Tyr Tyr Tyr Phe Gln Gln Gly Trp Asn Ile Phe
    770                 775                 780

Asp Ser Ile Ile Val Ile Leu Ser Leu Met Glu Leu Gly Leu Ser Arg
785                 790                 795                 800

Met Ser Asn Leu Ser Val Leu Arg Ser Phe Arg Leu Leu Arg Val Phe
                805                 810                 815

Lys Leu Ala Lys Ser Trp Pro Thr Leu Asn Thr Leu Ile Lys Ile Ile
            820                 825                 830

Gly Asn Ser Val Gly Ala Leu Gly Asn Leu Thr Leu Val Leu Ala Ile
        835                 840                 845

Ile Val Phe Ile Phe Ala Val Val Gly Met Gln Leu Phe Gly Lys Asn
    850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
                885                 890                 895
```

```
Gly Glu Trp Ile Glu Thr Met Trp Asp Cys Met Glu Val Ser Gly Gln
            900                 905                 910

Ser Leu Cys Leu Leu Val Phe Leu Leu Val Met Val Ile Gly Asn Leu
        915                 920                 925

Val Val Leu Asn Leu Phe Leu Ala Leu Leu Leu Ser Ser Phe Ser Ala
    930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
                965                 970                 975

Thr Trp Asp Phe Cys Cys Gly Leu Leu Arg Gln Arg Pro Gln Lys Pro
            980                 985                 990

Ala Ala Leu Ala Ala Gln Gly Gln  Leu Pro Ser Cys Ile  Ala Thr Pro
        995                 1000                 1005

Tyr Ser  Pro Pro Pro Pro Glu  Thr Glu Lys Val Pro  Pro Thr Arg
    1010                 1015                 1020

Lys Glu  Thr Arg Phe Glu Glu  Gly Glu Gln Pro Gly  Gln Gly Thr
    1025                 1030                 1035

Pro Gly  Asp Pro Glu Pro Val  Cys Val Pro Ile Ala  Val Ala Glu
    1040                 1045                 1050

Ser Asp  Thr Asp Asp Gln Glu  Glu Asp Glu Glu Asn  Ser Leu Gly
    1055                 1060                 1065

Thr Glu  Glu Glu Ser Ser Lys  Gln Gln Glu Ser Gln  Pro Val Ser
    1070                 1075                 1080

Gly Gly  Pro Glu Ala Pro Pro  Asp Ser Arg Thr Trp  Ser Gln Val
    1085                 1090                 1095

Ser Ala  Thr Ala Ser Ser Glu  Ala Glu Ala Ser Ala  Ser Gln Ala
    1100                 1105                 1110

Asp Trp  Arg Gln Gln Trp Lys  Ala Glu Pro Gln Ala  Pro Gly Cys
    1115                 1120                 1125

Gly Glu  Thr Pro Glu Asp Ser  Cys Ser Glu Gly Ser  Thr Ala Asp
    1130                 1135                 1140

Met Thr  Asn Thr Ala Glu Leu  Leu Glu Gln Ile Pro  Asp Leu Gly
    1145                 1150                 1155

Gln Asp  Val Lys Asp Pro Glu  Asp Cys Phe Thr Glu  Gly Cys Val
    1160                 1165                 1170

Arg Arg  Cys Pro Cys Cys Ala  Val Asp Thr Thr Gln  Ala Pro Gly
    1175                 1180                 1185

Lys Val  Trp Trp Arg Leu Arg  Lys Thr Cys Tyr His  Ile Val Glu
    1190                 1195                 1200

His Ser  Trp Phe Glu Thr Phe  Ile Ile Phe Met Ile  Leu Leu Ser
    1205                 1210                 1215

Ser Gly  Ala Leu Ala Phe Glu  Asp Ile Tyr Leu Glu  Glu Arg Lys
    1220                 1225                 1230

Thr Ile  Lys Val Leu Leu Glu  Tyr Ala Asp Lys Met  Phe Thr Tyr
    1235                 1240                 1245

Val Phe  Val Leu Glu Met Leu  Leu Lys Trp Val Ala  Tyr Gly Phe
    1250                 1255                 1260

Lys Lys  Tyr Phe Thr Asn Ala  Trp Cys Trp Leu Asp  Phe Leu Ile
    1265                 1270                 1275

Val Asp  Val Ser Leu Val Ser  Leu Val Ala Asn Thr  Leu Gly Phe
    1280                 1285                 1290

Ala Glu  Met Gly Pro Ile Lys  Ser Leu Arg Thr Leu  Arg Ala Leu
```

```
    1295                1300                1305

Arg Pro  Leu Arg Ala Leu Ser  Arg Phe Glu Gly Met  Arg Val Val
    1310                1315                1320

Val Asn  Ala Leu Val Gly Ala  Ile Pro Ser Ile Met  Asn Val Leu
    1325                1330                1335

Leu Val  Cys Leu Ile Phe Trp  Leu Ile Phe Ser Ile  Met Gly Val
    1340                1345                1350

Asn Leu  Phe Ala Gly Lys Phe  Gly Arg Cys Ile Asn  Gln Thr Glu
    1355                1360                1365

Gly Asp  Leu Pro Leu Asn Tyr  Thr Ile Val Asn Asn  Lys Ser Gln
    1370                1375                1380

Cys Glu  Ser Leu Asn Leu Thr  Gly Glu Leu Tyr Trp  Thr Lys Val
    1385                1390                1395

Lys Val  Asn Phe Asp Asn Val  Gly Ala Gly Tyr Leu  Ala Leu Leu
    1400                1405                1410

Gln Val  Ala Thr Phe Lys Gly  Trp Met Asp Ile Met  Tyr Ala Ala
    1415                1420                1425

Val Asp  Ser Arg Gly Tyr Glu  Glu Gln Pro Gln Trp  Glu Tyr Asn
    1430                1435                1440

Leu Tyr  Met Tyr Ile Tyr Phe  Val Ile Phe Ile Ile  Phe Gly Ser
    1445                1450                1455

Phe Phe  Thr Leu Asn Leu Phe  Ile Gly Val Ile Ile  Asp Asn Phe
    1460                1465                1470

Asn Gln  Gln Lys Lys Lys Leu  Gly Gly Gln Asp Ile  Phe Met Thr
    1475                1480                1485

Glu Glu  Gln Lys Lys Tyr Tyr  Asn Ala Met Lys Lys  Leu Gly Ser
    1490                1495                1500

Lys Lys  Pro Gln Lys Pro Ile  Pro Arg Pro Leu Asn  Lys Tyr Gln
    1505                1510                1515

Gly Phe  Ile Phe Asp Ile Val  Thr Lys Gln Ala Phe  Asp Val Thr
    1520                1525                1530

Ile Met  Phe Leu Ile Cys Leu  Asn Met Val Thr Met  Met Val Glu
    1535                1540                1545

Thr Asp  Asp Gln Ser Pro Glu  Lys Ile Asn Ile Leu  Ala Lys Ile
    1550                1555                1560

Asn Leu  Leu Phe Val Ala Ile  Phe Thr Gly Glu Cys  Ile Val Lys
    1565                1570                1575

Leu Ala  Ala Leu Arg His Tyr  Tyr Phe Thr Asn Ser  Trp Asn Ile
    1580                1585                1590

Phe Asp  Phe Val Val Val Ile  Leu Ser Ile Val Gly  Thr Val Leu
    1595                1600                1605

Ser Asp  Ile Ile Gln Lys Tyr  Phe Phe Ser Pro Thr  Leu Phe Arg
    1610                1615                1620

Val Ile  Arg Leu Ala Arg Ile  Gly Arg Ile Leu Arg  Leu Ile Arg
    1625                1630                1635

Gly Ala  Lys Gly
    1640
```

<210> SEQ ID NO 12
<211> LENGTH: 2016
<212> TYPE: PRT
<213> ORGANISM: Homo sapiens

<400> SEQUENCE: 12

-continued

```
Met Ala Asn Phe Leu Leu Pro Arg Gly Thr Ser Ser Phe Arg Arg Phe
1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
    50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu
                85                  90                  95

Asn Lys Gly Lys Thr Ile Phe Arg Phe Ser Ala Thr Asn Ala Leu Tyr
            100                 105                 110

Val Leu Ser Pro Phe His Pro Ile Arg Arg Ala Ala Val Lys Ile Leu
        115                 120                 125

Val His Ser Leu Phe Asn Met Leu Ile Met Cys Thr Ile Leu Thr Asn
    130                 135                 140

Cys Val Phe Met Ala Gln His Asp Pro Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Gly Phe Cys Leu His Ala Phe Thr Phe Leu Arg Asp Pro
            180                 185                 190

Trp Asn Trp Leu Asp Phe Ser Val Ile Ile Met Ala Tyr Thr Thr Glu
        195                 200                 205

Phe Val Asp Leu Gly Asn Val Ser Ala Leu Arg Thr Phe Arg Val Leu
    210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
            260                 265                 270

Met Gly Asn Leu Arg His Lys Cys Val Arg Asn Phe Thr Ala Leu Asn
        275                 280                 285

Gly Thr Asn Gly Ser Val Glu Ala Asp Gly Leu Val Trp Glu Ser Leu
    290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                325                 330                 335

Glu Gly Tyr Arg Cys Leu Lys Ala Gly Glu Asn Pro Asp His Gly Tyr
            340                 345                 350

Thr Ser Phe Asp Ser Phe Ala Trp Ala Phe Leu Ala Leu Phe Arg Leu
        355                 360                 365

Met Thr Gln Asp Cys Trp Glu Arg Leu Tyr Gln Gln Thr Leu Arg Ser
    370                 375                 380

Ala Gly Lys Ile Tyr Met Ile Phe Phe Met Leu Val Ile Phe Leu Gly
385                 390                 395                 400

Ser Phe Tyr Leu Val Asn Leu Ile Leu Ala Val Val Ala Met Ala Tyr
                405                 410                 415

Glu Glu Gln Asn Gln Ala Thr Ile Ala Glu Thr Glu Glu Lys Glu Lys
```

-continued

```
            420                 425                 430

Arg Phe Gln Glu Ala Met Glu Met Leu Lys Lys Glu His Glu Ala Leu
        435                 440                 445

Thr Ile Arg Gly Val Asp Thr Val Ser Arg Ser Ser Leu Glu Met Ser
    450                 455                 460

Pro Leu Ala Pro Val Asn Ser His Glu Arg Arg Ser Lys Arg Arg Lys
465                 470                 475                 480

Arg Met Ser Ser Gly Thr Glu Glu Cys Gly Glu Asp Arg Leu Pro Lys
                485                 490                 495

Ser Asp Ser Glu Asp Gly Pro Arg Ala Met Asn His Leu Ser Leu Thr
            500                 505                 510

Arg Gly Leu Ser Arg Thr Ser Met Lys Pro Arg Ser Ser Arg Gly Ser
        515                 520                 525

Ile Phe Thr Phe Arg Arg Arg Asp Leu Gly Ser Glu Ala Asp Phe Ala
    530                 535                 540

Asp Asp Glu Asn Ser Thr Ala Gly Glu Ser Glu Ser His His Thr Ser
545                 550                 555                 560

Leu Leu Val Pro Trp Pro Leu Arg Arg Thr Ser Ala Gln Gly Gln Pro
                565                 570                 575

Ser Pro Gly Thr Ser Ala Pro Gly His Ala Leu His Gly Lys Lys Asn
            580                 585                 590

Ser Thr Val Asp Cys Asn Gly Val Val Ser Leu Leu Gly Ala Gly Asp
        595                 600                 605

Pro Glu Ala Thr Ser Pro Gly Ser His Leu Leu Arg Pro Val Met Leu
    610                 615                 620

Glu His Pro Pro Asp Thr Thr Thr Pro Ser Glu Glu Pro Gly Gly Pro
625                 630                 635                 640

Gln Met Leu Thr Ser Gln Ala Pro Cys Val Asp Gly Phe Glu Glu Pro
                645                 650                 655

Gly Ala Arg Gln Arg Ala Leu Ser Ala Val Ser Val Leu Thr Ser Ala
            660                 665                 670

Leu Glu Glu Leu Glu Glu Ser Arg His Lys Cys Pro Pro Cys Trp Asn
        675                 680                 685

Arg Leu Ala Gln Arg Tyr Leu Ile Trp Glu Cys Cys Pro Leu Trp Met
    690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
                725                 730                 735

Glu His Tyr Asn Met Thr Ser Glu Phe Glu Glu Met Leu Gln Val Gly
            740                 745                 750

Asn Leu Val Phe Thr Gly Ile Phe Thr Ala Glu Met Thr Phe Lys Ile
        755                 760                 765

Ile Ala Leu Asp Pro Tyr Tyr Tyr Phe Gln Gln Gly Trp Asn Ile Phe
    770                 775                 780

Asp Ser Ile Ile Val Ile Leu Ser Leu Met Glu Leu Gly Leu Ser Arg
785                 790                 795                 800

Met Ser Asn Leu Ser Val Leu Arg Ser Phe Arg Leu Leu Arg Val Phe
                805                 810                 815

Lys Leu Ala Lys Ser Trp Pro Thr Leu Asn Thr Leu Ile Lys Ile Ile
            820                 825                 830

Gly Asn Ser Val Gly Ala Leu Gly Asn Leu Thr Leu Val Leu Ala Ile
        835                 840                 845
```

-continued

```
Ile Val Phe Ile Phe Ala Val Val Gly Met Gln Leu Phe Gly Lys Asn
    850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
                885                 890                 895

Gly Glu Trp Ile Glu Thr Met Trp Asp Cys Met Glu Val Ser Gly Gln
            900                 905                 910

Ser Leu Cys Leu Leu Val Phe Leu Leu Val Met Val Ile Gly Asn Leu
        915                 920                 925

Val Val Leu Asn Leu Phe Leu Ala Leu Leu Leu Ser Ser Phe Ser Ala
    930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
                965                 970                 975

Thr Trp Asp Phe Cys Cys Gly Leu Leu Arg Gln Arg Pro Gln Lys Pro
            980                 985                 990

Ala Ala Leu Ala Ala Gln Gly Gln  Leu Pro Ser Cys Ile  Ala Thr Pro
        995                 1000                1005

Tyr Ser  Pro Pro Pro Pro Glu  Thr Glu Lys Val Pro  Pro Thr Arg
    1010                1015                1020

Lys Glu  Thr Arg Phe Glu Glu  Gly Glu Gln Pro Gly  Gln Gly Thr
    1025                1030                1035

Pro Gly  Asp Pro Glu Pro Val  Cys Val Pro Ile Ala  Val Ala Glu
    1040                1045                1050

Ser Asp  Thr Asp Asp Gln Glu  Glu Asp Glu Glu Asn  Ser Leu Gly
    1055                1060                1065

Thr Glu  Glu Glu Ser Ser Lys  Gln Gln Glu Ser Gln  Pro Val Ser
    1070                1075                1080

Gly Gly  Pro Glu Ala Pro Pro  Asp Ser Arg Thr Trp  Ser Gln Val
    1085                1090                1095

Ser Ala  Thr Ala Ser Ser Glu  Ala Glu Ala Ser Ala  Ser Gln Ala
    1100                1105                1110

Asp Trp  Arg Gln Gln Trp Lys  Ala Glu Pro Gln Ala  Pro Gly Cys
    1115                1120                1125

Gly Glu  Thr Pro Glu Asp Ser  Cys Ser Glu Gly Ser  Thr Ala Asp
    1130                1135                1140

Met Thr  Asn Thr Ala Glu Leu  Leu Glu Gln Ile Pro  Asp Leu Gly
    1145                1150                1155

Gln Asp  Val Lys Asp Pro Glu  Asp Cys Phe Thr Glu  Gly Cys Val
    1160                1165                1170

Arg Arg  Cys Pro Cys Cys Ala  Val Asp Thr Thr Gln  Ala Pro Gly
    1175                1180                1185

Lys Val  Trp Trp Arg Leu Arg  Lys Thr Cys Tyr His  Ile Val Glu
    1190                1195                1200

His Ser  Trp Phe Glu Thr Phe  Ile Ile Phe Met Ile  Leu Leu Ser
    1205                1210                1215

Ser Gly  Ala Leu Ala Phe Glu  Asp Ile Tyr Leu Glu  Glu Arg Lys
    1220                1225                1230

Thr Ile  Lys Val Leu Leu Glu  Tyr Ala Asp Lys Met  Phe Thr Tyr
    1235                1240                1245
```

-continued

```
Val Phe  Val Leu Glu Met Leu  Leu Lys Trp Val Ala  Tyr Gly Phe
    1250                 1255                 1260

Lys Lys  Tyr Phe Thr Asn Ala  Trp Cys Trp Leu Asp  Phe Leu Ile
    1265                 1270                 1275

Val Asp  Val Ser Leu Val Ser  Leu Val Ala Asn Thr  Leu Gly Phe
    1280                 1285                 1290

Ala Glu  Met Gly Pro Ile Lys  Ser Leu Arg Thr Leu  Arg Ala Leu
    1295                 1300                 1305

Arg Pro  Leu Arg Ala Leu Ser  Arg Phe Glu Gly Met  Arg Val Val
    1310                 1315                 1320

Val Asn  Ala Leu Val Gly Ala  Ile Pro Ser Ile Met  Asn Val Leu
    1325                 1330                 1335

Leu Val  Cys Leu Ile Phe Trp  Leu Ile Phe Ser Ile  Met Gly Val
    1340                 1345                 1350

Asn Leu  Phe Ala Gly Lys Phe  Gly Arg Cys Ile Asn  Gln Thr Glu
    1355                 1360                 1365

Gly Asp  Leu Pro Leu Asn Tyr  Thr Ile Val Asn Asn  Lys Ser Gln
    1370                 1375                 1380

Cys Glu  Ser Leu Asn Leu Thr  Gly Glu Leu Tyr Trp  Thr Lys Val
    1385                 1390                 1395

Lys Val  Asn Phe Asp Asn Val  Gly Ala Gly Tyr Leu  Ala Leu Leu
    1400                 1405                 1410

Gln Val  Ala Thr Phe Lys Gly  Trp Met Asp Ile Met  Tyr Ala Ala
    1415                 1420                 1425

Val Asp  Ser Arg Gly Tyr Glu  Glu Gln Pro Gln Trp  Glu Tyr Asn
    1430                 1435                 1440

Leu Tyr  Met Tyr Ile Tyr Phe  Val Ile Phe Ile Ile  Phe Gly Ser
    1445                 1450                 1455

Phe Phe  Thr Leu Asn Leu Phe  Ile Gly Val Ile Ile  Asp Asn Phe
    1460                 1465                 1470

Asn Gln  Gln Lys Lys Lys Leu  Gly Gly Gln Asp Ile  Phe Met Thr
    1475                 1480                 1485

Glu Glu  Gln Lys Lys Tyr Tyr  Asn Ala Met Lys Lys  Leu Gly Ser
    1490                 1495                 1500

Lys Lys  Pro Gln Lys Pro Ile  Pro Arg Pro Leu Asn  Lys Tyr Gln
    1505                 1510                 1515

Gly Phe  Ile Phe Asp Ile Val  Thr Lys Gln Ala Phe  Asp Val Thr
    1520                 1525                 1530

Ile Met  Phe Leu Ile Cys Leu  Asn Met Val Thr Met  Met Val Glu
    1535                 1540                 1545

Thr Asp  Asp Gln Ser Pro Glu  Lys Ile Asn Ile Leu  Ala Lys Ile
    1550                 1555                 1560

Asn Leu  Leu Phe Val Ala Ile  Phe Thr Gly Glu Cys  Ile Val Lys
    1565                 1570                 1575

Leu Ala  Ala Leu Arg His Tyr  Tyr Phe Thr Asn Ser  Trp Asn Ile
    1580                 1585                 1590

Phe Asp  Phe Val Val Val Ile  Leu Ser Ile Val Gly  Thr Val Leu
    1595                 1600                 1605

Ser Asp  Ile Ile Gln Lys Tyr  Phe Phe Ser Pro Thr  Leu Phe Arg
    1610                 1615                 1620

Val Ile  Arg Leu Ala Arg Ile  Gly Arg Ile Leu Arg  Leu Ile Arg
    1625                 1630                 1635

Gly Ala  Lys Gly Ile Arg Thr  Leu Leu Phe Ala Leu  Met Met Ser
```

```
    1640                1645                1650

Leu Pro  Ala Leu Phe Asn Ile  Gly Leu Leu Leu Phe  Leu Val Met
    1655                1660                1665

Phe Ile  Tyr Ser Ile Phe Gly  Met Ala Asn Phe Ala  Tyr Val Lys
    1670                1675                1680

Trp Glu  Ala Gly Ile Asp Asp  Met Phe Asn Phe Gln  Thr Phe Ala
    1685                1690                1695

Asn Ser  Met Leu Cys Leu Phe  Gln Ile Thr Thr Ser  Ala Gly Trp
    1700                1705                1710

Asp Gly  Leu Leu Ser Pro Ile  Leu Asn Thr Gly Pro  Pro Tyr Cys
    1715                1720                1725

Asp Pro  Thr Leu Pro Asn Ser  Asn Gly Ser Arg Gly  Asp Cys Gly
    1730                1735                1740

Ser Pro  Ala Val Gly Ile Leu  Phe Phe Thr Thr Tyr  Ile Ile Ile
    1745                1750                1755

Ser Phe  Leu Ile Val Val Asn  Met Tyr Ile Ala Ile  Ile Leu Glu
    1760                1765                1770

Asn Phe  Ser Val Ala Thr Glu  Glu Ser Thr Glu Pro  Leu Ser Glu
    1775                1780                1785

Asp Asp  Phe Asp Met Phe Tyr  Glu Ile Trp Glu Lys  Phe Asp Pro
    1790                1795                1800

Glu Ala  Thr Gln Phe Ile Glu  Tyr Ser Val Leu Ser  Asp Phe Ala
    1805                1810                1815

Asp Ala  Leu Ser Glu Pro Leu  Arg Ile Ala Lys Pro  Asn Gln Ile
    1820                1825                1830

Ser Leu  Ile Asn Met Asp Leu  Pro Met Val Ser Gly  Asp Arg Ile
    1835                1840                1845

His Cys  Met Asp Ile Leu Phe  Ala Phe Thr Lys Arg  Val Leu Gly
    1850                1855                1860

Glu Ser  Gly Glu Met Asp Ala  Leu Lys Ile Gln Met  Glu Glu Lys
    1865                1870                1875

Phe Met  Ala Ala Asn Pro Ser  Lys Ile Ser Tyr Glu  Pro Ile Thr
    1880                1885                1890

Thr Thr  Leu Arg Arg Lys His  Glu Glu Val Ser Ala  Met Val Ile
    1895                1900                1905

Gln Arg  Ala Phe Arg Arg His  Leu Leu Gln Arg Ser  Leu Lys His
    1910                1915                1920

Ala Ser  Phe Leu Phe Arg Gln  Gln Ala Gly Ser Gly  Leu Ser Glu
    1925                1930                1935

Glu Asp  Ala Pro Glu Arg Glu  Gly Leu Ile Ala Tyr  Val Met Ser
    1940                1945                1950

Glu Asn  Phe Ser Arg Pro Leu  Gly Pro Pro Ser Ser  Ser Ser Ile
    1955                1960                1965

Ser Ser  Thr Ser Phe Pro Pro  Ser Tyr Asp Ser Val  Thr Arg Ala
    1970                1975                1980

Thr Ser  Asp Asn Leu Gln Val  Arg Gly Ser Asp Tyr  Ser His Ser
    1985                1990                1995

Glu Asp  Leu Ala Asp Phe Pro  Pro Ser Pro Asp Arg  Asp Arg Glu
    2000                2005                2010

Ser Ile  Val
    2015
```

<210> SEQ ID NO 13

<211> LENGTH: 8504
<212> TYPE: DNA
<213> ORGANISM: Artificial Sequence
<220> FEATURE:
<223> OTHER INFORMATION: cDNA Sequence for full-length SCN5A

<400> SEQUENCE: 13
agacggcggc ggcgcccgta ggatgcaggg atcgctcccc cggggccgct gagcctgcgc 60
ccagtgcccc gagccccgcg ccgagccgag tccgcgccaa gcagcagccg cccacccccgg 120 ggcccggccg ggggaccagc agcttcccca caggcaacgt gaggagagcc tgtgcccaga 180
agcaggatga gaagatggca aacttcctat tacctcgggg caccagcagc ttccgcaggt 240
tcacacggga gtccctggca gccatcgaga agcgcatggc agagaagcaa gcccgcggct 300
caaccacctt gcaggagagc cgagaggggc tgcccgagga ggaggctccc cggccccagc 360
tggacctgca ggcctccaaa aagctgccag atctctatgg caatccaccc caagagctca 420
tcggagagcc cctggaggac ctggacccct tctatagcac ccaaaagact ttcatcgtac 480
tgaataaagg caagaccatc ttccggttca gtgccaccaa cgccttgtat gtcctcagtc 540
ccttccaccc catccggaga gcggctgtga agattctggt tcactcgctc ttcaacatgc 600
tcatcatgtg caccatcctc accaactgcg tgttcatggc ccagcacgac cctccaccct 660
ggaccaagta tgtcgagtac accttcaccg ccatttacac ctttgagtct ctggtcaaga 720
ttctggctcg aggcttctgc ctgcacgcgt tcactttcct tcgggaccca tggaactggc 780
tggactttag tgtgattatc atggcataca caactgaatt tgtggacctg ggcaatgtct 840
cagccttacg caccttccga gtcctccggg ccctgaaaac tatatcagtc atttcagggc 900
tgaagaccat cgtgggggcc ctgatccagt ctgtgaagaa gctggctgat gtgatggtcc 960
tcacagtctt ctgcctcagc gtctttgccc tcatcggcct gcagctcttc atgggcaacc 1020
taaggcacaa gtgcgtgcgc aacttcacag cgctcaacgg caccaacggc tccgtggagg 1080
ccgacggctt ggtctgggaa tccctggacc tttacctcag tgatccagaa aattacctgc 1140
tcaagaacgg cacctctgat gtgttactgt gtgggaacag ctctgacgct gggacatgtc 1200
cggagggcta ccggtgccta aaggcaggcg agaaccccga ccacggctac accagcttcg 1260
attcctttgc ctgggccttt cttgcactct tccgcctgat gacgcaggac tgctgggagc 1320
gcctctatca gcagaccctc aggtccgcag ggaagatcta catgatcttc ttcatgcttg 1380
tcatcttcct ggggtccttc tacctggtga acctgatcct ggccgtggtc gcaatggcct 1440
atgaggagca aaaccaagcc accatcgctg agaccgagga gaaggaaaag cgcttccagg 1500
aggccatgga aatgctcaag aaagaacacg aggccctcac catcaggggt gtggataccg 1560
tgtcccgtag ctccttggag atgtcccctt tggccccagt aaacagccat gagagaagaa 1620
gcaagaggag aaaacggatg tcttcaggaa ctgaggagtg tggggaggac aggctcccca 1680
agtctgactc agaagatggt cccagagcaa tgaatcatct cagcctcacc cgtggcctca 1740
gcaggacttc tatgaagcca cgttccagcc gcgggagcat tttcaccttt cgcaggcgag 1800
acctgggttc tgaagcagat tttgcagatg atgaaaacag cacagcgggg gagagcgaga 1860
gccaccacac atcactgctg gtgccctggc ccctgcgccg gaccagtgcc cagggacagc 1920
ccagtcccgg aacctcggct cctggccacg ccctccatgg caaaaagaac agcactgtgg 1980
actgcaatgg ggtggtctca ttactggggg caggcgaccc agaggccaca tccccaggaa 2040
gccacctcct ccgccctgtg atgctagagc acccgccaga cacgaccacg ccatcggagg 2100
agccaggcgg gccccagatg ctgacctccc aggctccgtg tgtagatggc ttcgaggagc 2160

-continued

```
caggagcacg gcagcgggcc ctcagcgcag tcagcgtcct caccagcgca ctggaagagt   2220
tagaggagtc tcgccacaag tgtccaccat gctggaaccg tctcgcccag cgctacctga   2280
tctgggagtg ctgcccgctg tggatgtcca tcaagcaggg agtgaagttg gtggtcatgg   2340
acccgtttac tgacctcacc atcactatgt gcatcgtact caacacactc ttcatggcgc   2400
tggagcacta caacatgaca agtgaattcg aggagatgct gcaggtcgga aacctggtct   2460
tcacagggat tttcacagca gagatgacct tcaagatcat tgccctcgac ccctactact   2520
acttccaaca gggctggaac atcttcgaca gcatcatcgt catccttagc ctcatggagc   2580
tgggcctgtc ccgcatgagc aacttgtcgg tgctgcgctc cttccgcctg ctgcgggtct   2640
tcaagctggc caaatcatgg cccaccctga acacactcat caagatcatc gggaactcag   2700
tgggggcact ggggaacctg acactggtgc tagccatcat cgtgttcatc tttgctgtgg   2760
tgggcatgca gctctttggc aagaactact cggagctgag ggacagcgac tcaggcctgc   2820
tgcctcgctg gcacatgatg gacttctttc atgccttcct catcatcttc cgcatcctct   2880
gtggagagtg gatcgagacc atgtgggact gcatggaggt gtcggggcag tcattatgcc   2940
tgctggtctt cttgcttgtt atggtcattg gcaaccttgt ggtcctgaat ctcttcctgg   3000
ccttgctgct cagctccttc agtgcagaca acctcacagc ccctgatgag gacagagaga   3060
tgaacaacct ccagctggcc ctggcccgca tccagagggg cctgcgcttt gtcaagcgga   3120
ccacctggga tttctgctgt ggtctcctgc ggcagcggcc tcagaagccc gcagcccttg   3180
ccgcccaggg ccagctgccc agctgcattg ccacccccta ctccccgcca cccccagaga   3240
cggagaaggt gcctcccacc cgcaaggaaa cacggtttga ggaaggcgag caaccaggcc   3300
agggcacccc cggggatcca gagcccgtgt gtgtgcccat cgctgtggcc gagtcagaca   3360
cagatgacca agaagaagat gaggagaaca gcctgggcac ggaggaggag tccagcaagc   3420
agcaggaatc ccagcctgtg tccggtggcc cagaggcccc tccggattcc aggacctgga   3480
gccaggtgtc agcgactgcc tcctctgagg ccgaggccag tgcatctcag gccgactggc   3540
ggcagcagtg gaaagcggaa ccccaggccc cagggtgcgg tgagacccca gaggacagtt   3600
gctccgaggg cagcacagca gacatgacca acaccgctga gctcctggag cagatccctg   3660
acctcggcca ggatgtcaag gacccagagg actgcttcac tgaaggctgt gtccggcgct   3720
gtccctgctg tgcggtggac accacacagg ccccagggaa ggtctggtgg cggttgcgca   3780
agacctgcta ccacatcgtg gagcacagct ggttcgagac attcatcatc ttcatgatcc   3840
tactcagcag tggagcgctg gccttcgagg acatctacct agaggagcgg aagaccatca   3900
aggttctgct tgagtatgcc gacaagatgt tcacatatgt cttcgtgctg gagatgctgc   3960
tcaagtgggt ggcctacggc ttcaagaagt acttcaccaa tgcctggtgc tggctcgact   4020
tcctcatcgt agacgtctct ctggtcagcc tggtggccaa caccctgggc tttgccgaga   4080
tgggccccat caagtcactg cggacgctgc gtgcactccg tcctctgaga gctctgtcac   4140
gatttgaggg catgagggtg gtggtcaatg ccctggtggg cgccatcccg tccatcatga   4200
acgtcctcct cgtctgcctc atcttctggc tcatcttcag catcatgggc gtgaacctct   4260
ttgcggggaa gtttgggagg tgcatcaacc agacagaggg agacttgcct ttgaactaca   4320
ccatcgtgaa caacaagagc cagtgtgagt ccttgaactt gaccggagaa ttgtactgga   4380
ccaaggtgaa agtcaacttt gacaacgtgg gggccgggta cctggccctt ctgcaggtgg   4440
caacatttaa aggctggatg gacattatgt atgcagctgt ggactccagg gggtatgaag   4500
```

-continued

```
agcagcctca gtgggaatac aacctctaca tgtacatcta ttttgtcatt ttcatcatct   4560
ttgggtcttt cttcaccctg aacctcttta ttggtgtcat cattgacaac ttcaaccaac   4620
agaagaaaaa gttagggggc caggacatct tcatgacaga ggagcagaag aagtactaca   4680
atgccatgaa gaagctgggc tccaagaagc cccagaagcc catcccacgg cccctgaaca   4740
agtaccaggg cttcatattc gacattgtga ccaagcaggc ctttgacgtc accatcatgt   4800
ttctgatctg cttgaatatg gtgaccatga tggtggagac agatgaccaa agtcctgaga   4860
aaatcaacat cttggccaag atcaacctgc tctttgtggc catcttcaca ggcgagtgta   4920
ttgtcaagct ggctgccctg cgccactact acttcaccaa cagctggaat atcttcgact   4980
tcgtggttgt catcctctcc atcgtgggca ctgtgctctc ggacatcatc cagaagtact   5040
tcttctcccc gacgctcttc cgagtcatcc gcctggcccg aataggccgc atcctcagac   5100
tgatccgagg ggccaagggg atccgcacgc tgctctttgc cctcatgatg tccctgcctg   5160
ccctcttcaa catcgggctg ctgctcttcc tcgtcatgtt catctactcc atctttggca   5220
tggccaactt cgcttatgtc aagtgggagg ctggcatcga cgacatgttc aacttccaga   5280
ccttcgccaa cagcatgctg tgcctcttcc agatcaccac gtcggccggc tgggatggcc   5340
tcctcagccc catcctcaac actgggccgc cctactgcga ccccactctg cccaacagca   5400
atggctctcg gggggactgc gggagcccag ccgtgggcat cctcttcttc accacctaca   5460
tcatcatctc cttcctcatc gtggtcaaca tgtacattgc catcatcctg gagaacttca   5520
gcgtggccac ggaggagagc accgagcccc tgagtgagga cgacttcgat atgttctatg   5580
agatctggga gaaatttgac ccagaggcca ctcagtttat tgagtattcg gtcctgtctg   5640
actttgccga tgccctgtct gagccactcc gtatcgccaa gcccaaccag ataagcctca   5700
tcaacatgga cctgcccatg gtgagtgggg accgcatcca ttgcatggac attctctttg   5760
ccttcaccaa aagggtcctg gggggagtctg gggagatgga cgccctgaag atccagatgg   5820
aggagaagtt catggcagcc aacccatcca agatctccta cgagcccatc accaccacac   5880
tccggcgcaa gcacgaagag gtgtcggcca tggttatcca gagagccttc cgcaggcacc   5940
tgctgcaacg ctctttgaag catgcctcct tcctcttccg tcagcaggcg ggcagcggcc   6000
tctccgaaga ggatgcccct gagcgagagg gcctcatcgc ctacgtgatg agtgagaact   6060
tctcccgacc ccttggccca ccctccagct cctccatctc ctccacttcc ttcccaccct   6120
cctatgacag tgtcactaga gccaccagcg ataacctcca ggtgcggggg tctgactaca   6180
gccacagtga agatctcgcc gacttccccc cttctccgga cagggaccgt gagtccatcg   6240
tgtgagcctc ggcctggctg gccaggacac actgaaaagc agcctttttc accatggcaa   6300
acctaaatgc agtcagtcac aaaccagcct ggggccttcc tggctttggg agtaagaaat   6360
gggcctcagc cccgcggatc aaccaggcag agttctgtgg cgccgcgtgg acagccggag   6420
cagttggcct gtgcttggag gcctcagata gacctgtgac ctggtctggt caggcaatgc   6480
cctgcggctc tggaaagcaa cttcatccca gctgctgagg cgaaatataa aactgagact   6540
gtatatgttg tgaatgggct ttcataaatt tattatattt gatatttttt tacttgagca   6600
aagaactaag gatttttcca tggacatggg cagcaattca cgctgtctct tcttaaccct   6660
gaacaagagt gtctatggag cagccggaag tctgttctca aagcagaagt ggaatccagt   6720
gtggctccca caggtcttca ctgcccaggg gtcgaatggg gtccccctcc cacttgacct   6780
gagatgctgg gagggctgaa cccccactca cacaagcaca cacacacagt cctcacacac   6840
ggaggccaga cacaggccgt gggacccagg ctcccagcct aagggagaca ggcctttccc   6900
```

```
tgccggcccc ccaaggatgg ggttcttgtc cacggggctc actctggccc cctattgtct   6960
ccaaggtccc attttccccc tgtgttttca cgcaggtcat attgtcagtc ctacaaaaat   7020
aaaaggcttc cagaggagag tggcctgggt cccagggctg gccctaggca ctgatagttg   7080
ccttttcttc ccctcctgta agagtattaa caaaaccaaa ggacacaagg gtgcaagccc   7140
cattcacggc ctggcatgca gcttgtcctt gctcctggaa cctggcaggc cctgcccagc   7200
cagccatcgg aagagagggc tgagccatgg gggtttgggg ctaagaagtt caccagccct   7260
gagccatggc ggcccctcag cctgcctgaa gagaggaaac tggcgatctc ccagggctct   7320
ctggaccata cgcggaggag ttttctgtgt ggtctccagc tcctctccag acacagagac   7380
atgggagtgg ggagcggagc ttggccctgc gccctgtgca gggaaaggga tggtcaggcc   7440
cagttctcgt gcccttagag gggaatgaac catggcacct ttgagagagg gggcactgtg   7500
gtcaggccca gcctctctgg ctcagcccgg gatcctgatg gcacccacac agaggacctc   7560
tttggggcaa gatccaggtg gtcccatagg tcttgtgaaa aggctttttc agggaaaaat   7620
attttactag tccaatcacc cccaggacct cttcagctgc tgacaatcct atttagcata   7680
tgcaaatctt ttaacataga gaactgtcac cctgaggtaa cagggtcaac tggcgaagcc   7740
tgagcaggca ggggcttggc tgccccattc cagctctccc atggagcccc tccaccgggc   7800
gcatgcctcc caggccacct cagtctcacc tgccggctct gggctggctg ctcctaacct   7860
acctcgccga gctgtcggag ggctggacat ttgtggcagt gctgaagggg gcattgccgg   7920
cgagtaaagt attatgtttc ttcttgtcac cccagttccc ttggtggcaa ccccagaccc   7980
aacccatgcc cctgacagat ctagttctct tctcctgtgt tccctttgag tccagtgtgg   8040
gacacggttt aactgtccca gcgacatttc tccaagtgga aatcctattt ttgtagatct   8100
ccatgctttg ctctcaaggc ttggagaggt atgtgcccct cctgggtgct caccgcctgc   8160
tacacaggca ggaatgcggt tgggaggcag gtcgggctgc cagcccagct ggccggaagg   8220
agactgtggt ttttgtgtgt gtggacagcc cgggagcttt gagacaggtg cctggggctg   8280
gctgcagacg gtgtggttgg gggtgggagg tgagctagac ccaaccctta gcttttagcc   8340
tggctgtcac ctttttaatt tccagaactg cacaatgacc agcaggaggg aaggacagac   8400
atcaagtgcc agatgttgtc tgaactaatc gagcacttct caccaaactt catgtataaa   8460
taaaatacat atttttaaaa caaaccaata aatggcttac atga                    8504
```

<210> SEQ ID NO 14
<211> LENGTH: 145
<212> TYPE: PRT
<213> ORGANISM: Artificial Sequence
<220> FEATURE:
<223> OTHER INFORMATION: hhSCN5A-E28 Splice Variant

<400> SEQUENCE: 14

```
Leu Ser Ile Val Gly Thr Val Leu Ser Asp Ile Ile Gln Lys Tyr Phe
1               5                   10                  15

Phe Ser Pro Thr Leu Phe Arg Val Ile Arg Leu Ala Arg Ile Gly Arg
            20                  25                  30

Ile Leu Arg Leu Ile Arg Gly Ala Lys Gly Ile Arg Thr Leu Leu Phe
        35                  40                  45

Ala Leu Met Met Ser Leu Pro Ala Leu Phe Asn Ile Gly Leu Leu Leu
    50                  55                  60

Phe Leu Val Met Phe Ile Ser Ser Ile Phe Gly Met Ala Asn Phe Ala
65                  70                  75                  80
```

```
Ser Val Lys Trp Glu Ala Gly Ile Asp Asp Met Phe Asn Phe Gln Thr
                85                  90                  95

Phe Ala Asn Ser Met Leu Cys Ile Phe Gln Ile Thr Thr Ser Ala Gly
            100                 105                 110

Trp Asp Gly Leu Leu Ser Pro Ile Leu Asn Thr Gly Pro Pro Tyr Cys
        115                 120                 125

Asp Pro Thr Leu Pro Asn Pro Ser Pro Asp Arg Asp Arg Glu Ser Ile
    130                 135                 140

Val
145
```

<210> SEQ ID NO 15
<211> LENGTH: 748
<212> TYPE: DNA
<213> ORGANISM: Artificial Sequence
<220> FEATURE:
<223> OTHER INFORMATION: hhSCN5A-E28A transcriptional variant

<400> SEQUENCE: 15

```
ctctccatcg tgggcactgt gctctcggac atcatccaga agtacttctt ctccccgacg      60

ctcttccgag tcatccgcct ggcccgaata ggccgcatcc tcagactgat ccgaggggcc     120

aaggggatcc gcacgctgct ctttgccctc atgatgtccc tgcctgccct cttcaacatc     180

gggctgctgc tcttcctcgt catgttcatc tactccatct ttggcatggc caacttcgct     240

tatgtcaagt gggaggctgg catcgacgac atgttcaact tccagacctt cgccaacagc     300

atgctgtgcc tcttccagat caccacgtcg gccggctggg atggcctcct cagccccatc     360

ctcaacactg ggccgcccta ctgcgacccc actctgcgct ctcgccgact tccccccttc     420

tccggacagg gaccgtgagt ccatcgtgtg agcctcggcc tggctggcca ggacacactg     480

aaaagcagcc tttttcacca gctgcagacg gtgtggttgg gggtgggagg tgagctagac     540

ccaaccctta gcttttagcc tggctgtcac ctttttaatt tccagaactg cacaatgacc     600

agcaggaggg gagaagagag taggaaaaag gagggaagga cagacatcaa gtgccagatg     660

ttgtctgaac taatcgagca cttctcacca aacttcatgt ataaataaaa tacatatttt     720

taaaacaaac caataaatgg cttacatg                                        748
```

<210> SEQ ID NO 16
<211> LENGTH: 12
<212> TYPE: PRT
<213> ORGANISM: Artificial Sequence
<220> FEATURE:
<223> OTHER INFORMATION: hhSCN5A-E28B transcriptional variant amino acid sequence

<400> SEQUENCE: 16

```
Leu Ser Ile Val Gly Ala Leu Leu Val Ser Met Lys
1               5                   10
```

<210> SEQ ID NO 17
<211> LENGTH: 100
<212> TYPE: DNA
<213> ORGANISM: Artificial Sequence
<220> FEATURE:
<223> OTHER INFORMATION: hhSCN5A-E28B transcriptional variant nucleotide sequence

<400> SEQUENCE: 17
ctctccatcg tgggagccct cctagtgagt atgaagtgat atctcactga ggttttggtt 60
tgcaaaagca aatgactgat gactaacgat gcaggacatc 100

<210> SEQ ID NO 18
<211> LENGTH: 16
<212> TYPE: PRT
<213> ORGANISM: Artificial Sequence
<220> FEATURE:
<223> OTHER INFORMATION: hhSCN5A-E28C transcriptional variant amino acid sequence

<400> SEQUENCE: 18

Leu Ser Ile Val Glu Leu His Asn Asp Gln Gln Glu Gly Arg Arg Glu
1 5 10 15

<210> SEQ ID NO 19
<211> LENGTH: 176
<212> TYPE: DNA
<213> ORGANISM: Artificial Sequence
<220> FEATURE:
<223> OTHER INFORMATION: hhSCN5A-E28C transcriptional variant nucleotide sequence

<400> SEQUENCE: 19
ctctccatcg tggaactgca caatgaccag caggagggga gaagagagta ggaaaaagga 60
gggaaggaca gacatcaagt gccagatgtt gtctgaacta atcgagcact tctcaccaaa 120
cttcatgtat aaataaaata catattttta aaacaaacca ataaatggct tacatg 176

<210> SEQ ID NO 20
<211> LENGTH: 42
<212> TYPE: PRT
<213> ORGANISM: Artificial Sequence
<220> FEATURE:
<223> OTHER INFORMATION: hhSCN5A-E28D transcriptional variant amino acid sequence

<400> SEQUENCE: 20

Leu Ser Ile Val Gly Thr Val Leu Ser Asp Ile Ile Gln Lys Tyr Phe
1 5 10 15

Phe Ser Pro Thr Leu Phe Arg Val Ile Arg Leu Ala Arg Ile Gly Arg
20 25 30

Ile Leu Arg Leu Ile Arg Gly Ala Lys Gly
35 40

<210> SEQ ID NO 21
<211> LENGTH: 174
<212> TYPE: DNA
<213> ORGANISM: Artificial Sequence
<220> FEATURE:
<223> OTHER INFORMATION: hhSCN5A-E28D transcriptional variant nucleotide sequence

<400> SEQUENCE: 21
ctctccatcg tgggcactgt gctctcggac atcatccaga agtacttctt ctccccgacg 60
ctcttccgag tcatccgcct ggcccgaata ggccgcatcc tcagactgat ccgaggggcc 120
aaggggataa ataaaataca tatttttaaa acaaaccaat aaatggctta catg 174